United States Patent
Zeng et al.

(10) Patent No.: US 7,329,536 B2
(45) Date of Patent: Feb. 12, 2008

(54) PIEZOIMMUNOSENSOR

(75) Inventors: Xiangqun Zeng, Rochester, MI (US);
Gabrielle Stryker, Rochester Hills, MI (US); Raymond L. Mernaugh, Franklin, TN (US)

(73) Assignees: Oakland University, Rochester, MI (US); Vanderbilt University, Nashville, TN (US)

( * ) Notice: Subject to any disclaimer, the term of this patent is extended or adjusted under 35 U.S.C. 154(b) by 431 days.

(21) Appl. No.: 10/861,617

(22) Filed: Jun. 4, 2004

(65) Prior Publication Data

US 2005/0003560 A1    Jan. 6, 2005

Related U.S. Application Data

(60) Provisional application No. 60/476,123, filed on Jun. 5, 2003.

(51) Int. Cl.
*C12M 1/34* (2006.01)

(52) U.S. Cl. ............... 435/287.2; 310/311; 310/313 R; 310/340; 422/57; 435/287.1; 435/287.9; 435/810; 435/969; 435/975; 435/7.5; 436/512; 436/513; 436/518; 436/524; 436/527; 436/808

(58) Field of Classification Search ...................... None
See application file for complete search history.

(56) References Cited

U.S. PATENT DOCUMENTS

| | | | | | |
|---|---|---|---|---|---|
| 4,236,893 | A | * | 12/1980 | Rice | 436/513 |
| 4,242,096 | A | * | 12/1980 | Oliveira et al. | 436/500 |
| 4,314,821 | A | * | 2/1982 | Rice | 436/540 |
| 4,735,906 | A | * | 4/1988 | Bastiaans | 436/527 |
| 4,789,804 | A | * | 12/1988 | Karube et al. | 310/311 |
| 4,999,284 | A | * | 3/1991 | Ward et al. | 435/4 |

* cited by examiner

*Primary Examiner*—Christopher L. Chin
(74) *Attorney, Agent, or Firm*—Ian C. McLeod

(57) ABSTRACT

An apparatus comprising one or more piezoelectric mass sensors for use in diagnostic and analytic processes, in particular for immunochemical detection of diagnostically relevant analytes in real time, is described. Each piezoelectric mass sensor comprises a piezoelectric crystal with a receptor surface which has immobilized thereon a lawn of recombinant antibodies comprising single $V_H$ chain or single-chain Fv (scFv) polypeptides specific for a particular antigen. Binding of antigen to the recombinant antibodies results in a change in mass on the receptor surface which is detected as a change in resonant frequency. In a preferred embodiment, the receptor layer is a precious metal such as gold which facilitates self-assembly of the recombinant antibodies into a lawn on the receptor surface via a cysteine residue at the carboxy terminus of the attachment polypeptide.

33 Claims, 48 Drawing Sheets

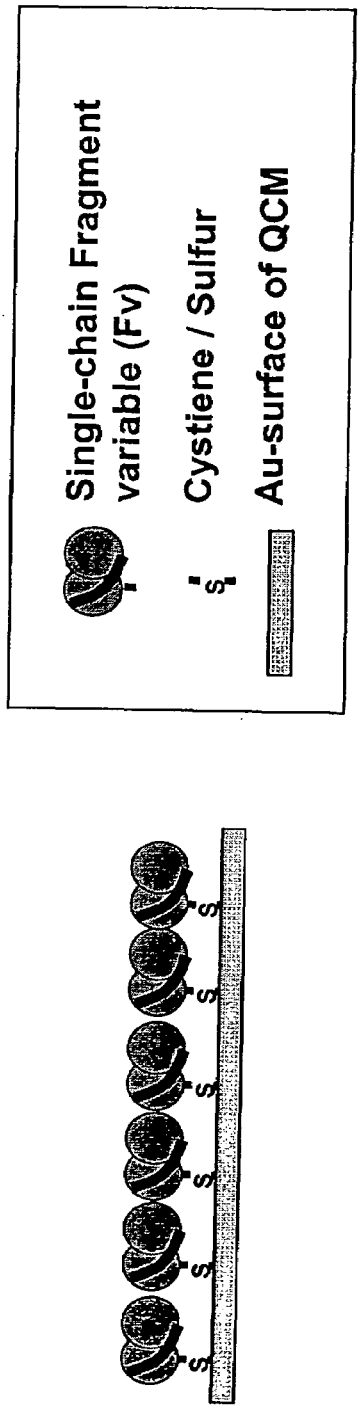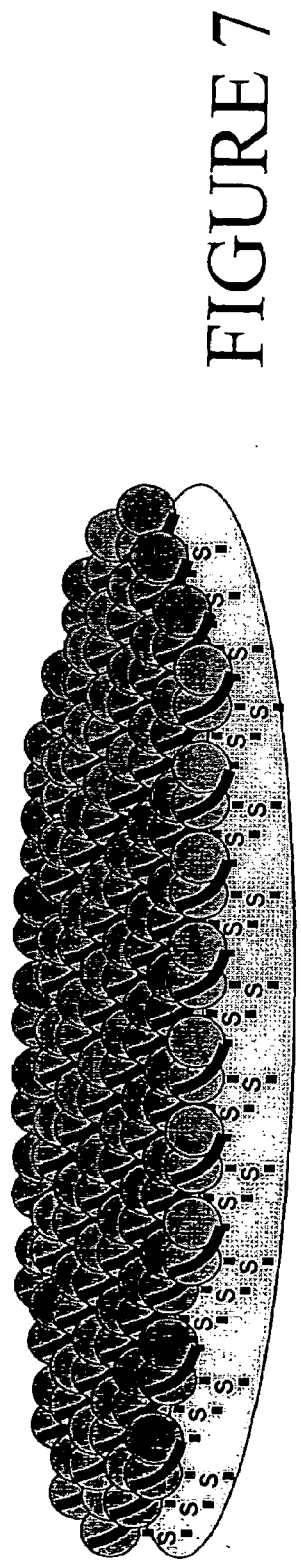
Incorporate a binding residue to form a correctly oriented, thin, tightly packed monolayer on the surface of the QCM.
FIGURE 7

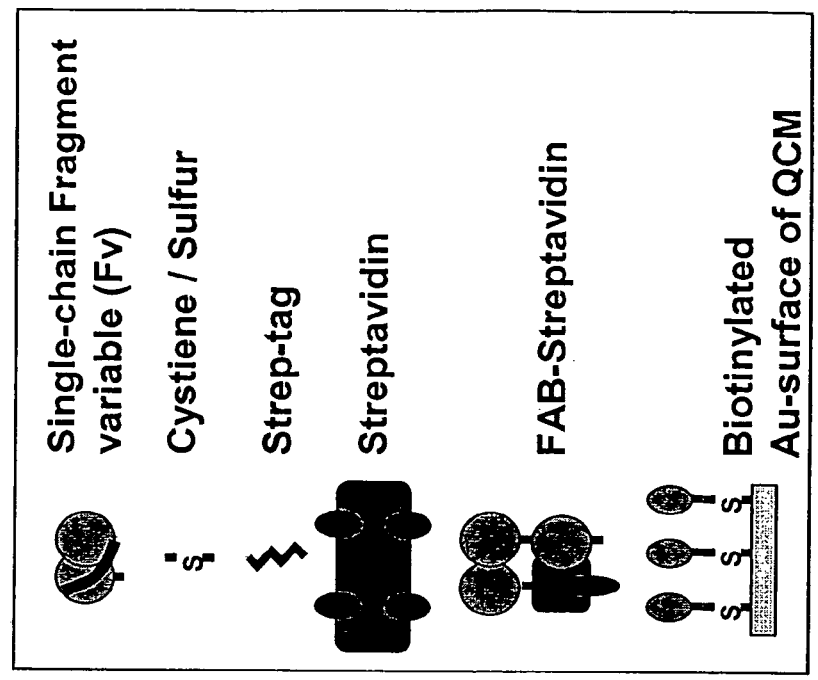
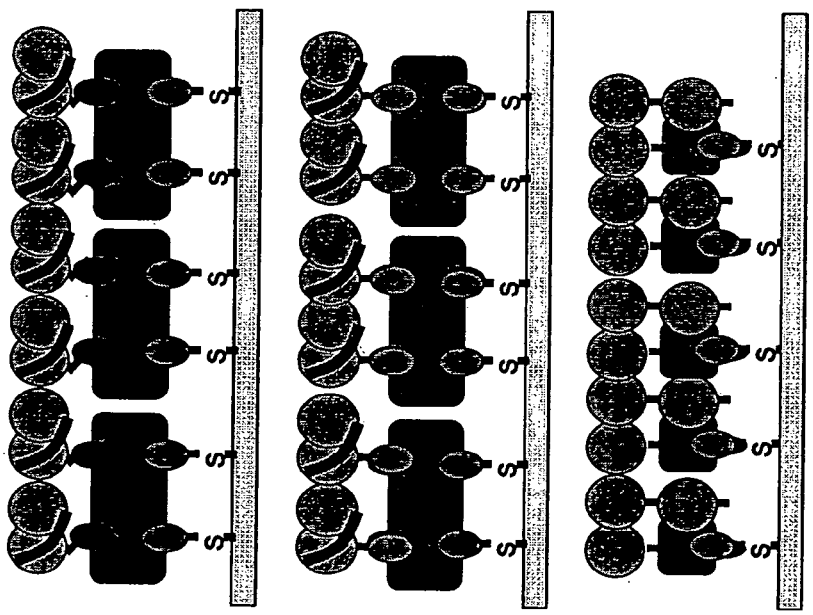
a. Carboxy-terminal strep-tag (Strep-tag vector)
b. Biotinylated carboxy-terminus (pin-point vector)
c. FAB-streptavidin fusion protein
FIGURE 9A-9C

US 7,329,536 B2

PIEZOIMMUNOSENSOR

CROSS-REFERENCE TO RELATED APPLICATIONS

This application claims priority to U.S. Provisional Application Ser. No. 60/476,123, filed Jun. 5, 2003.

STATEMENT REGARDING FEDERALLY SPONSORED RESEARCH OR DEVELOPMENT

This invention was supported by NIBIB Grant Number 1R21 EB000672-01. The U.S. Government has certain rights in this invention.

BACKGROUND OF THE INVENTION (1) Field of the Invention

The present invention relates to an apparatus comprising one or more piezoelectric mass sensors for use in diagnostic and analytic processes, in particular for immunochemical detection of diagnostically relevant analytes. Each piezoelectric mass sensor comprises a piezoelectric crystal with a receptor surface which has immobilized thereon a lawn of recombinant antibodies comprising single $V_H$ chain or single-chain Fv (scFv) polypeptides specific for a particular antigen. Binding of antigen to the recombinant antibodies results in a change in mass on the receptor surface which is detected as a change in resonant frequency. In a preferred embodiment, the receptor layer is a precious metal such as gold which facilitates self-assembly of the recombinant antibodies into a lawn on the receptor surface via a cysteine residue at the carboxy terminus of the attachment polypeptide.

(2) Description of Related Art

In 1880, Pierre and Jacques Curie observed that pressure exerted on a small piece of quartz causes an electrical potential difference between the deformed surfaces, and found that application of a voltage to a quartz crystal caused physical distortion (Lu C, Czanderna A W. edt, Methods and Phenomena, Volume 7, Elsevier, New York, 1984, 198-280). They named their discovery the piezoelectric or "pressure electric" effect.

The piezoelectric property characteristic of quartz is only possible in ionic crystalline solids lacking a center of inversion. Of the 32 three-dimensional point groups, only twenty can possibly exhibit the piezoelectric effect; however in some it may be too small to detect. It was found that α-quartz exhibited the piezoelectric effect and, because of its mechanical and thermal stability, is used to construct highly stable oscillator circuits with pg/cm² mass sensitivity.

Depending on the cut-angle, a large number of different resonator types can be obtained from α-quartz. The mode of vibration that is most sensitive to the addition or removal of mass from a quartz crystal is the thickness shear mode. To make a quartz crystal oscillate in the thickness shear mode, the crystal must be cut at a specific angle with respect to the principal optical axes of the quartz. AT-cut quartz crystals cut at an angle of 35.25° to the z-axis exhibit a high frequency stability ($\Delta f/f=10^{-8}$) and almost zero temperature coefficient between 0-50°, and are most frequently used for mass-sensing devices.

Interfacial mass changes can be related to changes in the QCM oscillation frequency by applying Sauerbrey's equation (G. Sauerbrey., Z. Phys. 1959; 155:206-222), $\Delta f = -2\Delta m n f_0^2/(A(\mu_q \rho_q)^{1/2})$, where n is the overtone number, $\mu_q$ is the shear modulus of the quartz ($2.947 \times 10^{11}$ g/(cm sec²), and $\rho_q$ is the density of the quartz (2.648 g/cm³), and which assumes the foreign mass is strongly coupled to the resonator.

Mass detection by using Sauerbrey's equation is usually straightforward if the device is operating in the gas or the vacuum phase, the added mass binds tightly to the surface, and the films of added mass are stiff and thin, such as in electroplating. Because of their small size, high sensitivity, and stability, piezoelectric crystals have been used as microbalances in the determination of thin-layer thickness and in general gas-sorption studies (Grate J W, Martin S J, White R M., Anal Chem 1993; 65:940A-948A and Lu C, Czanderna A W. edt, Methods and Phenomena, Volume 7, Elsevier, New York, 1984, 198-280).

The use of QCM in analytical applications was delayed due to lack of suitable oscillator circuits that enable the shear-wave resonator to be operated in fluids. In 1982, Nomura and Okuhara were the first to report on a circuitry capable of oscillating in liquid (Nomura T, Okuhara M. Anal Chim Acta. 1982; 142;281-284). This gave the starting point for development of a new class of analytical tools. The incorporation of various chemically sensitive layers has resulted in the explosive growth of piezoelectric sensors (Janshoff A, Galla H, Steinem C. Angew Chem. Int. Ed. 2000; 39:4004-4032). The major advantages of piezoelectric mass sensors are simplicity of construction and operation, weight, cost, availability, and low power requirements. Unlike electrochemical sensors, the measurement is conducted in a monopolar mode, i.e., only a single physical probe is necessary. Mass sensors have high sensitivity and can be used for a broad range of compounds.

In recent years, methods based on the use of piezoelectric crystal devices have been developed for immunoassay applications (Guilbault G G, Hock B, Schmid R., Biosensors Bioelectronics. 1990; 5:13-26; Schmitt N, Tessier L, Watier H, Patat F, Sensors and Actuators B. 1997; 43:217-223 and Su X, Chew F T, Li S F Y., E. Anal Biochem. 1999; 273:66-72). However, researchers are still skeptical about the potential of piezoelectric mass sensing devices as biosensors. Rodahl et. al (Rodahl M, Hook F, Fredriksson C, Keller C A, Krozer A, Brzezinski P, Voinova M, Kasemo B. Faraday Discussions. 1997; 107:229-246) studied protein adsorption, lipid vesicle adsorption, and cell adhesion on QCM electrode. Their results demonstrated that even thin biofilms dissipate a significant amount of energy owing to QCM oscillation. They attribute the measured increase in energy dissipation to (1) a viscoelastic porous structure that is strained during oscillation, (2) trapped liquid that moves between or in and out of pores due to the deformation of the film, (3) the load from the bulk liquid which increases the strain of film.

The physics of biofilms in liquid is complex, which makes it difficult to obtain a generally explicit relationship between the added mass and the change in the frequency output. QCM may give a direct response signal that characterizes the binding event between a sensitive layer, immobilized on the surface of transducer, and the analytes to be detected. However, the mass estimated with the QCM response through the Sauerbrey equation and the mass measured can be quite different. Several papers demonstrated that the deposited mass is generally overestimated (Babacan S, Pivarnik P, Letcher S, Rand A G. Biosensors & Bioelectronics. 2000; 15:615-621 and Bizet K, Gabrielli C, Perrot H, Therasse J, Biosenors & Bioelectronics. 1998; 13:259-269). Another limitation of QCM biosensors arises from the large size of biomolecules such as immunoglobulins. Consequently, low densities of the binding molecule are usually immobilized on the surface. A signal will only be obtained if the interaction results in a net change of mass of the selective protein layer attached to the crystal. If the interaction is a displacement of one species with another, i.e., the exchange or catalytic reaction, the sensor surface is only a temporary host to the interacting species and the net changes of mass can be very small. For small biomolecules, such as some antigens, it is quite difficult to obtain an observable signal due to the small amount of sensitized molecule immobilized and limited sensitivity of commonly used 5 MHz and 10 MHz quartz crystal.

The above concerns did not stop researchers' enthusiasm for piezoelectric sensors. In the past decade, numerous studies have shown that adsorption of biomolecules on functionalized surface is one of the paramount applications of piezoelectric transducers. Examples include the study of the interaction of DNA and RNA with complementary strands (Okahata Y, Kawase M, Niikura K, Ohtake F, Furusawa H, Ebara Y. Anal Chem. 1998; 70:1288-1296), specific recognition of protein ligands by immobilized receptors, and the detection of virus capsids, bacteria, and mammalian cells (Fredriksson C, Kihlman S, Rodahl M, Kasemo B. Langmuir. 1998; 14:248-251). However, whether QCM will assert itself against established label-free sensors such as surface plasma resonance spectroscopy and interferometry rests on development of a functionalized film on quartz which is thin, rigid, and contains a high density of the sensing molecules.

The most sensitive analytic apparatus yet developed is the piezoelectric immunosensor which has the potential capability of detecting antigens in the picogram range. In addition, the piezoelectric immunosensor is believed to have the potential to detect antigens in or from the gas phase as well as in the liquid phase. The state of the art related to piezoelectric immunosensors are exemplified by the following U.S. patents.

U.S. Pat. No. 4,236,893 to Rice discloses an apparatus and method for performing immunoassays for detecting particular classes of antibodies in a liquid sample using a piezoelectric oscillator. The oscillator comprises a quartz crystal coated with an antigen recognized only by a particular class of antibody. The coated oscillator is incubated in the liquid sample for a time sufficient for the antibody to bind the antigen. Afterwards, the oscillator is removed from the sample, washed and dried, and the resonant frequency measured. A change in resonant frequency indicates the sample contained the particular class of antibody specific for the antigen.

U.S. Pat. No. 4,242,096 to Oliveira et al. discloses an indirect immunoassay for detecting an antigen in a liquid sample using a piezoelectric oscillator. The oscillator comprises a quartz crystal coated with an antigen to be detected. The coated oscillator is incubated in the liquid sample to which a predetermined amount of antibody specific for the antigen has been added for a time sufficient for the antibody to bind either the antigen in the sample or the antigen on the quartz crystal. Afterwards, the oscillator is removed from the sample and the resonant frequency measured. The amount of change in resonant frequency indirectly indicates the amount of antigen present in the liquid sample.

U.S. Pat. No. 4,246,344 to Silver III discloses a method for detecting adherent cells using a piezoelectric oscillator. The resonant frequency of a piezoelectric oscillator is determined and then incubated in a liquid sample for a time sufficient for adherent cells to adhere the oscillator. Afterwards, the oscillator is removed from the sample, washed and dried, and the resonant frequency determined. A change in resonant frequency indicates that the sample contains adherent cells.

U.S. Pat. No. 4,314,821 to Rice discloses an apparatus and method for performing immunoassays for detecting an antibody in a liquid sample using a piezoelectric oscillator. The oscillator comprises a quartz crystal coated with an antigen recognized by the antibody. The coated oscillator is incubated in the liquid sample for a time sufficient for the antibody to bind the antigen. Afterwards, the oscillator is removed from the sample, washed and dried, and the resonant frequency measured. A change in resonant frequency indicates the sample contained an antibody specific for the antigen.

U.S. Pat. No. 4,735,906 to Bastiaans discloses an apparatus and method for performing immunoassays for detecting an analyte using a piezoelectric sensor. The sensor comprises a piezoelectric crystal coated with a monomer layer of a silane derivative to which a member of a specific binding pair for the analyte is chemically bonded. When the sensor is incubated with a liquid sample containing the analyte, the analyte binds to the specific binding pair which then causes a change in the resonant frequency of the sensor.

U.S. Pat. No. 5,314,830 to Anderson et al. discloses a method for immobilizing an antibody on a surface such as the surface of the crystal comprising a piezoelectric oscillator. An antibody modified with a hydrophobic moiety attached to the antibody by a spacer comprising a water soluble polymer is directly absorbed to the surface of the surface.

U.S. Pat. No. 5,932,953 to Drees et al. discloses a method and system for detecting a material bound on a surface of a piezoelectric resonator. The method uses a sensing resonator that measures a change in insertion phase shift of the resonator caused by binding of the material being detected on the surface of the resonator instead of measuring the change in the oscillation frequency of the sensing resonator caused by the binding of the material being detected on the surface of the resonator.

U.S. Pat. No. 6,087,187 to Wiegland et al. discloses a method for using a piezoelectric sensor for the immunochemical detection of an analyte in a liquid sample. The piezoelectric sensor comprises a precious metal coating on the surface to which a specific binding partner is bound. Preferably, the specific binding partner is an antibody, antibody fragment, a lectin, or an antigen. The sensor is incubated with the sample for a time sufficient for the specific binding partner to bind the analyte which causes a shift in the resonant frequency of the sensor. Afterwards, the specific binding partner and bound analyte are removed from the surface.

Published U.S. Patent Application Nos. 20030077222, 20030073133, 20030072710, 20030068273, 20030053950, and 20030049204, all to Leyland-Jones, discloses immunosensors which in particular embodiments have antibodies, Fab fragments, or scFv polypeptides immobilized on the surface thereof.

Currently available biosensors as exemplified by the above U.S. patents provide accurate detection but have significant disadvantages in terms of cost, time needed for detection, lack of portability, ability to function in a "dirty" environment, and the need for highly trained technicians to operate the systems. Piezoimmunosensor (PZ) technology, which places antibodies on a quartz crystal microbalance (QCM) to detect minute changes in mass as the antibodies bind with antigens may address these drawbacks. However, use of piezoelectric technology in biosensors is problematic due to the complex nature of whole antibodies. For example, the large size and branching arms of whole antibodies increase their susceptibility to proteases and non-specific binding and trapping of antigen, which reduces sensitivity and accuracy. In addition, polyclonal antibodies are difficult to use because of their heterogeneous nature and monoclonal antibodies, while affording homogeneous binding characteristics, are labor intensive and expensive to produce.

Therefore, there is a need for a biosensor which provides sensitive and accurate detection but which does not have the drawbacks inherent in biosensors which use whole antibodies.

SUMMARY OF THE INVENTION

The present invention provides an apparatus comprising one or more piezoelectric mass sensors for use in diagnostic and analytic processes, in particular for immunochemical detection of diagnostically relevant analytes in real time which does not have the drawbacks inherent in prior art biosensors. Each piezoelectric mass sensor comprises a piezoelectric crystal with a receptor surface which has immobilized thereon a lawn of recombinant antibodies comprising single $V_H$ chain or single-chain Fv (scFv) polypeptides specific for a particular antigen. Binding of antigen to the recombinant antibodies results in a change in mass on the receptor surface which is detected as a change in resonant frequency of the crystal. In a preferred embodiment, the receptor layer is a precious metal such as gold which facilitates self-assembly of the recombinant scFv polypeptides into a lawn on the receptor surface via a cysteine residue at the carboxy terminus of the attachment polypeptide.

In one embodiment of the present invention, an apparatus for immunochemical detection of an analyte is provided which comprises a piezoelectric mass sensor with at least one receptor layer which provides a receptor surface and which has immobilized on the receptor surface a layer of recombinantly derived polypeptide molecules which bind the analyte, wherein each of the molecules comprises a single antibody variable heavy chain ($V_H$) or single-chain Fv (scFv) polypeptide specific for the analyte and an attachment polypeptide having a sequence which provides assembly of the molecules into the layer so as to be immmobilized on the receptor surface.

In a further embodiment, the recombinant polypeptide molecules bind a first epitope of the analyte and the apparatus comprises a second piezoelectric mass sensor with at least one second receptor layer which provides a second receptor surface and which has immobilized on the receptor surface a second layer of recombinantly derived polypeptide molecules which bind a second epitope of the analyte, wherein each of the molecules comprises a single antibody variable heavy chain ($V_H$) or single-chain Fv (scFv) polypeptide specific for the second epitope and an attachment polypeptide having a sequence which provides assembly of the molecules into the layer so as to be immobilized on the second receptor surface.

In a further embodiment, the apparatus comprises a control piezoelectric mass sensor with at least one receptor layer which provides a receptor surface and which has immobilized on the receptor surface a layer of recombinantly derived polypeptide molecules which bind the analyte, wherein each of the molecules comprises a single antibody variable heavy chain ($V_H$) or single-chain Fv (scFv) polypeptide specific for the analyte and an attachment polypeptide having a sequence which provides assembly of the molecules into the layer so as to be immmobilized on the receptor surface wherein binding of the analyte is blocked by a blocking agent.

In a further embodiment of the apparatus, the single antibody $V_H$ polypeptide specific for the analyte is derived from a library of single domain camel or llama antibodies and the amino terminus of the attachment polypeptide is linked to the carboxy terminus of the $V_H$ polypeptide.

In a further embodiment of the apparatus, the scFv polypeptide specific for the analyte comprises an antibody variable light chain ($V_L$) polypeptide specific for the analyte and an antibody variable heavy chain ($V_H$) polypeptide specific for the analyte which are covalently linked through a polypeptide linker such that the variable light and heavy polypeptide chains are linked together while still maintaining a conformation which allows the binding of the analyte and the amino terminus of the attachment polypeptide is covalently linked to the carboxy terminus of the $V_L$ polypeptide. Preferably, the polypeptide linker is covalently linked to an amino terminus of the $V_L$ polypeptide and a carboxy terminus of the $V_H$ polypeptide such that the $V_L$ and $V_H$ polypeptide chains are linked together.

In a further embodiment of the apparatus, the sequence of the attachment polypeptide comprises (1) at least one cysteine amino acid which provides a sulfhydryl moiety which allows the recombinantly derived polypeptide molecule to bind the receptor surface of the sensor to provide the layer on the receptor surface of the sensor, (2) a strep-tag sequence, which allows the recombinantly derived polypeptide molecule to bind streptavidin, and the receptor surface of the sensor comprises a biotin layer immobilized on the receptor surface by a sulfhydryl linkage which binds the streptavidin bound to the recombinantly derived polypeptide molecule to provide the layer on the receptor surface of the sensor, or (3) a polypeptide sequence for binding biotin, which allows the recombinantly derived polypeptide molecule to bind streptavidin, and the receptor layer comprises a biotin layer immobilized on the receptor surface by a sulfhydryl linkage which binds the streptavidin bound to the recombinantly derived polypeptide molecule to provide the layer on the receptor surface of the sensor.

In a further embodiment, the receptor layer comprises an electrode for the piezoelectric mass sensor and in a further still embodiment, the piezoelectric mass sensor is a quartz crystal microbalance.

In another embodiment of the present invention, an apparatus for immunochemical detection of a plurality of analytes is provided which comprises a plurality of piezoelectric mass sensors, each sensor with at least one receptor layer which provides a receptor surface and each sensor comprising a layer of recombinantly derived polypeptide molecules which bind one of the plurality of analytes immobilized on the receptor surface of the sensor wherein each of the molecules comprises a single antibody variable heavy chain ($V_H$) or single-chain Fv (scFv) polypeptide specific for the analyte and an attachment polypeptide having a sequence which provides assembly of the molecules into the layer so as to be immmobilized on the receptor surface, and wherein each piezoelectric mass sensor has a particular resonant frequency.

In a further embodiment, the apparatus comprises a control piezoelectric mass sensor with at least one receptor layer which provides a receptor surface and which has immobilized on the receptor surface a layer of recombinantly derived polypeptide molecules which bind the analyte, wherein each of the molecules comprises a single antibody variable heavy chain ($V_H$) or single-chain Fv (scFv)

polypeptide specific for the analyte and an attachment polypeptide having a sequence which provides assembly of the molecules into the layer so as to be immmobilized on the receptor surface wherein binding of the analyte is blocked by a blocking agent.

In a further embodiment of the apparatus, the single antibody $V_H$ polypeptide specific for the analyte is derived from a library of single domain camel or llama antibodies and the amino terminus of the attachment polypeptide is linked to the carboxy terminus of the $V_H$ polypeptide.

In a further embodiment of the apparatus, the scFv polypeptide specific for the analyte comprises an antibody variable light chain ($V_L$) polypeptide specific for the analyte and an antibody variable heavy chain ($V_H$) polypeptide specific for the analyte which are covalently linked through a polypeptide linker such that the variable light and heavy polypeptide chains are linked together while still maintaining a conformation which allows the binding of the analyte and the amino terminus of the attachment polypeptide is covalently linked to the carboxy terminus of the $V_L$ polypeptide. Preferably, the polypeptide linker is covalently linked to an amino terminus of the $V_L$ polypeptide and a carboxy terminus of the $V_H$ polypeptide such that the $V_L$ and $V_H$ polypeptide chains are linked together.

In a further embodiment of the apparatus, the sequence of the attachment polypeptide comprises (1) at least one cysteine amino acid which provides a sulfhydryl moiety which allows the recombinantly derived polypeptide molecule to bind the receptor surface of the sensor to provide the layer on the receptor surface of the sensor, (2) a strep-tag sequence, which allows the recombinantly derived polypeptide molecule to bind streptavidin, and the receptor surface of the sensor comprises a biotin layer immobilized on the receptor surface by a sulfhydryl linkage which binds the streptavidin bound to the recombinantly derived polypeptide molecule to provide the layer on the receptor surface of the sensor, or (3) a polypeptide sequence for binding biotin, which allows the recombinantly derived polypeptide molecule to bind streptavidin, and the receptor layer comprises a biotin layer immobilized on the receptor surface by a sulfhydryl linkage which binds the streptavidin bound to the recombinantly derived polypeptide molecule to provide the layer on the receptor surface of the sensor.

In a further embodiment, the receptor layer comprises an electrode for the piezoelectric mass sensor and in a further still embodiment, the piezoelectric mass sensor is a quartz crystal microbalance.

The present invention further provides a method for immunological detection of an analyte in a liquid sample, which comprises (a) providing an apparatus which comprises a piezoelectric mass sensor with at least one receptor layer which provides a receptor surface and which has immobilized on the receptor surface a layer of recombinantly derived polypeptide molecules which bind the analyte, wherein each of the molecules comprises a single antibody variable heavy chain ($V_H$) or single-chain Fv (scFv) polypeptide specific for the analyte and an attachment polypeptide having a sequence which provides assembly of the molecules into the layer so as to be immmobilized on the receptor surface; (b) measuring in a blank solution the resonant frequency of the piezoelectric mass sensor of the apparatus in step (a); (c) contacting the piezoelectric mass sensor of the apparatus in step (b) with the liquid sample for a time sufficient to allow the analyte to bind to the recombinantly derived polypeptide molecules; and (d) measuring the resonant frequency of the piezoelectric mass sensor of the apparatus in step (c) wherein a change in the resonant frequency indicates presence of the analyte in the sample.

In a further embodiment of the method, the recombinant polypeptide molecules bind a first epitope of the analyte and the apparatus comprises a second piezoelectric mass sensor with at least one second receptor layer which provides a second receptor surface and which has immobilized on the receptor surface a second layer of recombinantly derived polypeptide molecules which bind a second epitope of the analyte, wherein each of the molecules comprises a single antibody variable heavy chain ($V_H$) or single-chain Fv (scFv) polypeptide specific for the analyte and an attachment polypeptide having a sequence which provides assembly of the molecules into the layer so as to be immmobilized on the receptor surface.

In a further embodiment of the method, the apparatus comprises a control piezoelectric mass sensor with at least one receptor layer which provides a receptor surface and which has immobilized on the receptor surface a layer of recombinantly derived polypeptide molecules which bind the analyte, wherein each of the molecules comprises a single antibody variable heavy chain ($V_H$) or single-chain Fv (scFv) polypeptide specific for the analyte and an attachment polypeptide having a sequence which provides assembly of the molecules into the layer so as to be immmobilized on the receptor surface, wherein binding of the analyte is blocked by a blocking agent, and wherein the resonance frequency of the control sensor detects mass changes due to changes in temperature of the liquid sample during the measuring.

In a further embodiment of the method, the single antibody $V_H$ polypeptide specific for the analyte is derived from a library of single domain camel or llama antibodies and the amino terminus of the attachment polypeptide is linked to the carboxy terminus of the $V_H$ polypeptide.

In a further embodiment of the method, the scFv polypeptide specific for the analyte comprises an antibody variable light chain ($V_L$) polypeptide specific for the analyte and an antibody variable heavy chain ($V_H$) polypeptide specific for the analyte which are covalently linked through a polypeptide linker such that the variable light and heavy polypeptide chains are linked together while still maintaining a conformation which allows the binding of the analyte and the amino terminus of the attachment polypeptide is covalently linked to the carboxy terminus of the $V_L$ polypeptide. Preferably, the polypeptide linker is covalently linked to an amino terminus of the $V_L$ polypeptide and a carboxy terminus of the $V_H$ polypeptide such that the $V_L$ and $V_H$ polypeptide chains are linked together.

In a further embodiment of the method, the sequence of the attachment polypeptide comprises (1) at least one cysteine amino acid which provides a sulfhydryl moiety which allows the recombinantly derived polypeptide molecule to bind the receptor surface of the sensor to provide the layer on the receptor surface of the sensor, (2) a strep-tag sequence, which allows the recombinantly derived polypeptide molecule to bind streptavidin, and the receptor surface of the sensor comprises a biotin layer immobilized on the receptor surface by a sulfhydryl linkage which binds the streptavidin bound to the recombinantly derived polypeptide molecule to provide the layer on the receptor surface of the sensor, or (3) a polypeptide sequence for binding biotin, which allows the recombinantly derived polypeptide molecule to bind streptavidin, and the receptor layer comprises a biotin layer immobilized on the receptor surface by a sulfhydryl linkage which binds the streptavidin bound to the recombinantly derived polypeptide molecule to provide the layer on the receptor surface of the sensor.

In a further embodiment of the method, the receptor layer comprises an electrode for the piezoelectric mass sensor and in a further still embodiment, the piezoelectric mass sensor is a quartz crystal microbalance.

The present invention further provides a method for immunological detection of a plurality of analytes in a liquid sample to determine which analytes are present in the liquid sample, which comprises (a) providing an apparatus which comprises a plurality of piezoelectric mass sensors, each sensor with at least one receptor layer which provides a receptor surface and each sensor comprising a layer of recombinantly derived polypeptide molecules which bind one of the plurality of analytes immobilized on the receptor surface of the sensor wherein each of the molecules comprises a single antibody variable heavy chain ($V_H$) or single-chain Fv (scFv) polypeptide specific for the analyte and an attachment polypeptide having a sequence which provides assembly of the molecules into the layer so as to be immmobilized on the receptor surface, and wherein each piezoelectric mass sensor has a particular resonant frequency; (b) measuring in a blank solution the resonant frequency of each of the piezoelectric mass sensors of the apparatus in step (a); (c) contacting the piezoelectric mass sensors of the apparatus in step (b) with the liquid sample for a time sufficient to allow the analyte to bind to the recombinantly derived polypeptide molecules; and (d) measuring the resonant frequency of each of the piezoelectric mass sensors of the apparatus in step (c) wherein a change in the resonant frequency of a particular piezoelectric mass sensor indicates presence of a particular analyte in the sample which determines which analytes are present in the liquid sample.

In a further embodiment of the method, the apparatus comprises a control piezoelectric mass sensor with at least one receptor layer which provides a receptor surface and which has immobilized on the receptor surface a layer of recombinantly derived polypeptide molecules which bind the analyte, wherein each of the molecules comprises a single antibody variable heavy chain ($V_H$) or single-chain Fv (scFv) polypeptide specific for the analyte and an attachment polypeptide having a sequence which provides assembly of the molecules into the layer so as to be immmobilized on the receptor surface, wherein binding of the analyte is blocked by a blocking agent, and wherein the resonance frequency of the control sensor detects mass changes due to changes in temperature of the liquid sample during the measuring.

In a further embodiment of the method, the single antibody $V_H$ polypeptide specific for the analyte is derived from a library of single domain camel or llama antibodies and the amino terminus of the attachment polypeptide is linked to the carboxy terminus of the $V_H$ polypeptide.

In a further embodiment of the method, the scFv polypeptide specific for the analyte comprises an antibody variable light chain ($V_L$) polypeptide specific for the analyte and an antibody variable heavy chain ($V_H$) polypeptide specific for the analyte which are covalently linked through a polypeptide linker such that the variable light and heavy polypeptide chains are linked together while still maintaining a conformation which allows the binding of the analyte and the amino terminus of the attachment polypeptide is covalently linked to the carboxy terminus of the $V_L$ polypeptide. Preferably, polypeptide linker is covalently linked to an amino terminus of the $V_L$ polypeptide and a carboxy terminus of the $V_H$ polypeptide such that the $V_L$ and $V_H$ polypeptide chains are linked together.

The present invention further provides a kit for immunological detection of an analyte, which comprises an apparatus which comprises a piezoelectric mass sensor with at least one receptor layer which provides a receptor surface and which has immobilized on the receptor surface a layer of recombinantly derived polypeptide molecules which bind the analyte, wherein each of the molecules comprises a single antibody variable heavy chain ($V_H$) or single-chain Fv (scFv) polypeptide specific for the analyte and an attachment polypeptide having a sequence which provides assembly of the molecules into the layer so as to be immmobilized on the receptor surface.

In a further embodiment of the kit, the recombinant polypeptide molecules bind a first epitope of the analyte and the apparatus comprises a second piezoelectric mass sensor with at least one second receptor layer which provides a second receptor surface and which has immobilized on the receptor surface a second layer of recombinantly derived polypeptide molecules which bind a second epitope of the analyte, wherein each of the molecules comprises a single antibody variable heavy chain ($V_H$) or single-chain Fv (scFv) polypeptide specific for the second epitope and an attachment polypeptide having a sequence which provides assembly of the molecules into the layer so as to be immmobilized on the second receptor surface.

In a further embodiment of the kit, the apparatus comprises a control piezoelectric mass sensor with at least one receptor layer which provides a receptor surface and which has immobilized on the receptor surface a layer of recombinantly derived polypeptide molecules which bind the analyte, wherein each of the molecules comprises a single antibody variable heavy chain ($V_H$) or single-chain Fv (scFv) polypeptide specific for the analyte and an attachment polypeptide having a sequence which provides assembly of the molecules into the layer so as to be immmobilized on the receptor surface, wherein binding of the analyte is blocked by a blocking agent, and wherein the resonance frequency of the control sensor detects mass changes due to changes in temperature of the liquid sample during the measuring.

In a further embodiment of the kit, the single antibody $V_H$ polypeptide specific for the analyte is derived from a library of single domain camel or llama antibodies and the amino terminus of the attachment polypeptide is linked to the carboxy terminus of the $V_H$ polypeptide.

In a further embodiment of the kit, the scFv polypeptide specific for the analyte comprises an antibody variable light chain ($V_L$) polypeptide specific for the analyte and an antibody variable heavy chain ($V_H$) polypeptide specific for the analyte which are covalently linked through a polypeptide linker such that the variable light and heavy polypeptide chains are linked together while still maintaining a conformation which allows the binding of the analyte and the amino terminus of the attachment polypeptide is covalently linked to the carboxy terminus of the $V_L$ polypeptide. Preferably, the polypeptide linker is covalently linked to an amino terminus of the $V_L$ polypeptide and a carboxy terminus of the $V_H$ polypeptide such that the $V_L$ and $V_H$ polypeptide chains are linked together.

In a further embodiment of the kit, the sequence of the attachment polypeptide comprises (1) at least one cysteine amino acid which provides a sulfhydryl moiety which allows the recombinantly derived polypeptide molecule to bind the receptor surface of the sensor to provide the layer on the receptor surface of the sensor, (2) a strep-tag sequence, which allows the recombinantly derived polypeptide molecule to bind streptavidin, and the receptor surface of the sensor comprises a biotin layer immobilized on the receptor surface by a sulfhydryl linkage which binds the streptavidin bound to the recombinantly derived polypeptide molecule to provide the layer on the receptor surface of the sensor, or (3) a polypeptide sequence for binding biotin, which allows the recombinantly derived polypeptide molecule to bind streptavidin, and the receptor layer comprises a biotin layer immobilized on the receptor surface by a sulfhydryl linkage which binds the streptavidin bound to the recombinantly derived polypeptide molecule to provide the layer on the receptor surface of the sensor.

In a further embodiment of the kit, the receptor layer comprises an electrode for the piezoelectric mass sensor and in a further still embodiment, the piezoelectric mass sensor is a quartz crystal microbalance.

The present invention further provides a kit for immunological detection of a plurality of analytes, which comprises an apparatus which comprises a plurality of piezoelectric mass sensors, each sensor with at least one receptor layer which provides a receptor surface and each sensor comprising a layer of recombinantly derived polypeptide molecules which bind one of the plurality of analytes immobilized on the receptor surface of the sensor wherein each of the molecules comprises a single antibody variable heavy chain ($V_H$) or single-chain Fv (scFv) polypeptide specific for the analyte and an attachment polypeptide having a sequence which provides assembly of the molecules into the layer so as to be immmobilized on the receptor surface.

In a further embodiment of the kit, the apparatus comprises a control piezoelectric mass sensor with at least one receptor layer which provides a receptor surface and which has immobilized on the receptor surface a layer of recombinantly derived polypeptide molecules which bind the analyte, wherein each of the molecules comprises a single antibody variable heavy chain ($V_H$) or single-chain Fv (scFv) polypeptide specific for the analyte and an attachment polypeptide having a sequence which provides assembly of the molecules into the layer so as to be immmobilized on the receptor surface, wherein binding of the analyte is blocked by a blocking agent, and wherein the resonance frequency of the control sensor detects mass changes due to changes in temperature of the liquid sample during the measuring.

In a further embodiment of the kit, the single antibody $V_H$ polypeptide specific for the analyte is derived from a library of single domain camel or llama antibodies and the amino terminus of the attachment polypeptide is linked to the carboxy terminus of the $V_H$ polypeptide.

In a further embodiment of the kit, the scFv polypeptide specific for the analyte comprises an antibody variable light chain ($V_L$) polypeptide specific for the analyte and an antibody variable heavy chain ($V_H$) polypeptide specific for the analyte which are covalently linked through a polypeptide linker such that the variable light and heavy polypeptide chains are linked together while still maintaining a conformation which allows the binding of the analyte and the amino terminus of the attachment polypeptide is covalently linked to the carboxy terminus of the $V_L$ polypeptide. Preferably, the polypeptide linker is covalently linked to an amino terminus of the $V_L$ polypeptide and a carboxy terminus of the $V_H$ polypeptide such that the $V_L$ and $V_H$ polypeptide chains are linked together.

In a further embodiment of the kit, the sequence of the attachment polypeptide comprises (1) at least one cysteine amino acid which provides a sulfhydryl moiety which allows the recombinantly derived polypeptide molecule to bind the receptor surface of the sensor to provide the layer on the receptor surface of the sensor, (2) a strep-tag sequence, which allows the recombinantly derived polypeptide molecule to bind streptavidin, and the receptor surface of the sensor comprises a biotin layer immobilized on the receptor surface by a sulfhydryl linkage which binds the streptavidin bound to the recombinantly derived polypeptide molecule to provide the layer on the receptor surface of the sensor, or (3) a polypeptide sequence for binding biotin, which allows the recombinantly derived polypeptide molecule to bind streptavidin, and the receptor layer comprises a biotin layer immobilized on the receptor surface by a sulfhydryl linkage which binds the streptavidin bound to the recombinantly derived polypeptide molecule to provide the layer on the receptor surface of the sensor.

In a further embodiment of the kit, the receptor layer comprises an electrode for the piezoelectric mass sensor and in a further still embodiment, the piezoelectric mass sensor is a quartz crystal microbalance.

In a further still embodiment of the present invention, an apparatus for immunochemical detection of an analyte is provided which comprises a piezoelectric mass sensor with at least one receptor layer which provides a receptor surface and which has immobilized on the receptor surface a layer of first and second recombinantly derived polypeptide molecules which form a complex which binds the analyte, wherein the first polypeptide molecule comprises light chain variable and constant domains of an antibody specific for the analyte and the second polypeptide molecule comprises a heavy chain variable domain of the antibody in which the carboxy terminus of the second polypeptide is covalently linked to the amino terminus of a streptavidin polypeptide, wherein in the complex the streptavidin covalently linked to the heavy chain variable domain binds the light chain constant domain such that the variable light chain and the variable heavy chain domains are in a conformation which allows the binding of the analyte, and wherein the receptor surface of the sensor comprises a biotin layer immobilized on the receptor surface by a sulfhydryl linkage which binds the streptavidin covalently linked to the heavy chain variable domain and bound to the light chain constant domain to provide the layer.

In a further embodiment of the apparatus, the receptor layer comprises an electrode for the piezoelectric mass sensor and in a further still embodiment, the piezoelectric mass sensor is a quartz crystal microbalance.

In a further still embodiment of the present invention, a method for immunological detection of an analyte in a liquid sample is provided which comprises (a) providing an apparatus which comprises a piezoelectric mass sensor with at least one receptor layer which provides a receptor surface and which has immobilized on the receptor surface a layer of first and second recombinantly derived polypeptide molecules which form a complex which binds the analyte, wherein the first polypeptide molecule comprises light chain variable and constant domains of an antibody specific for the analyte and the second polypeptide molecule comprises a heavy chain variable domain of the antibody in which the carboxy terminus of the second polypeptide is covalently linked to the amino terminus of a streptavidin polypeptide, wherein in the complex the streptavidin covalently linked to the heavy chain variable domain binds the light chain constant domain such that the variable light chain and the variable heavy chain domains are in a conformation which allows the binding of the analyte, and wherein the receptor surface of the sensor comprises a biotin layer immobilized on the receptor surface by a sulfhydryl linkage which binds the streptavidin covalently linked to the heavy chain variable domain and bound to the light chain constant domain to provide the layer; (b) measuring in a blank solution the resonant frequency of the piezoelectric mass sensor of the apparatus in step (a); (c) contacting the piezoelectric mass sensor of the apparatus in step (b) with the liquid sample for a time sufficient to allow the analyte to bind to the complex of the recombinantly derived polypeptide molecules; and (d) measuring the resonant frequency of the piezoelectric mass sensor of the apparatus in step (c) wherein a change in the resonant frequency indicates presence of the analyte in the sample.

In a further embodiment of the method, the receptor layer comprises an electrode for the piezoelectric mass sensor and in a further still embodiment, the piezoelectric mass sensor is a quartz crystal microbalance.

In a further still embodiment of the present invention, a recombinant polypeptide molecule is provided which comprises an antibody variable light chain polypeptide specific for an analyte and an antibody variable heavy chain polypeptide specific for the analyte which are covalently linked through a polypeptide linker and an attachment polypeptide having a cysteine at the carboxy terminus, wherein the polypeptide linker is covalently linked to the amino terminus of the variable light chain polypeptide and the carboxy terminus of the variable heavy chain polypeptide such that the variable light and heavy polypeptide chains are linked together while still maintaining a conformation which allows the binding of the analyte, and the amino terminus of the attachment polypeptide is covalently linked to the carboxy terminus of the variable light chain polypeptide.

In a further still embodiment of the present invention, a recombinant polypeptide molecule is provided which comprises a first recombinant polypeptide molecule which comprises light chain variable and constant domains of an antibody specific for an analyte and a second recombinant polypeptide molecule which comprises a heavy chain variable domain of the antibody in which the carboxy terminus of the second recombinant polypeptide is covalently linked to the amino terminus of a streptavidin polypeptide, wherein in the complex the streptavidin covalently linked to the heavy chain variable domain binds the light chain constant domain such that the variable light chain and the variable heavy chain domains are in a conformation which allows the binding of the analyte.

The present invention further provides a recombinant single chain antibody (ScFv) molecule comprising a first variable chain polypeptide having a first amino acid sequence with an amino terminus and a carboxy terminus, which is an antibody variable light chain ($V_L$) or an antibody variable heavy chain ($V_H$) polypeptide specific for an analyte, a second variable chain polypeptide having a second amino acid sequence with an amino terminus and a carboxy terminus, which is an antibody variable light chain ($V_L$) or an antibody variable heavy chain ($V_H$) polypeptide specific for the analyte, and a polypeptide linker having a third amino acid sequence which covalently links the carboxy terminus of the first variable chain polypeptide to the amino terminus of the second variable chain polypeptide, and wherein the recombinant single chain antibody (ScFv) molecule has been modified to have one or more cysteines or histidines in one or more of the amino acid sequences.

In a further still embodiment of the recombinant single chain antibody (ScFv) molecule the one or more cysteines or histidines are covalently linked to the amino terminus of the first variable chain polypeptide. In a further still embodiment of the recombinant single chain antibody (ScFv) molecule the one or more cysteines or histidines are covalently linked to the carboxy terminus of the second variable chain polypeptide.

OBJECTS

It is an object of the present invention to provide a piezoelectric mass sensor for immunochemical detection of diagnostically relevant analytes.

It is a further object of the present invention to provide a piezoelectric mass sensor wherein detection of the analyte is via recombinant antibodies comprising single $V_H$ chain or single-chain Fv (scFv) polypeptides specific for a particular antigen.

These and other objects of the present invention will become increasingly apparent with reference to the following drawings and preferred embodiments.

DESCRIPTION OF THE DRAWINGS

FIG. 7 shows an embodiment of a piezoelectric sensor comprising the present invention wherein the surface of the sensor is coated with a layer of gold and the recombinant scFv polypeptide further includes an attachment polypeptide with a terminal cysteine which enables self-assembly of the recombinant scFv polypeptides into a lawn of recombinant scFv polypeptides on the surface of the sensor.

FIG. 9A shows a strategy for binding the recombinant scFv polypeptide to the surface of a piezoelectric material. The recombinant scFv polypeptide has a carboxy terminal strep-tag and the surface of the piezoelectric material is coated with gold to which biotin molecules have been immobilized via a terminal cysteine on the biotin molecules.

FIG. 9B shows a strategy for binding the recombinant scFv polypeptide to the surface of a piezoelectric material. The carboxy terminus of the recombinant scFv polypeptide has a biotin tag which binds to streptavidin which is bound to biotin immobilized via a terminal cysteine to the gold-coated surface of the piezoelectric material.

FIG. 9C shows a strategy for binding the recombinant scFv polypeptide to the surface of a piezoelectric material. A streptavidin-Fab complex is bound to biotin immobilized to the gold-coated surface of the piezoelectric material.

FIG. 41A shows frequency change vs. time; FIG. 41B shows frequency change vs. [rabbit IgG]$_0$ when various concentrations of rabbit IgG were added in 20 μl aliquots to the A10B-scFv-cys immobilized Au QCM electrodes in 1 ml PBS buffer; FIG. 41C shows frequency change vs. time curve when polyclonal goat α-rabbit IgG was added to A10B-scFv-cys immobilized Au QCM electrode after previously binding rabbit IgG in 1 ml PBS buffer (Curve A). Control: Frequency change vs. time curve when polyclonal goat α-rabbit IgG was added to A10B-scFv-cys immobilized Au QCM electrode in the absence of rabbit IgG (Curve B). Electrode was washed with biograded water and PBS buffer then dried before the secondary binding with the α-rabbit IgG.

DETAILED DESCRIPTION OF THE INVENTION

Figure 1A:
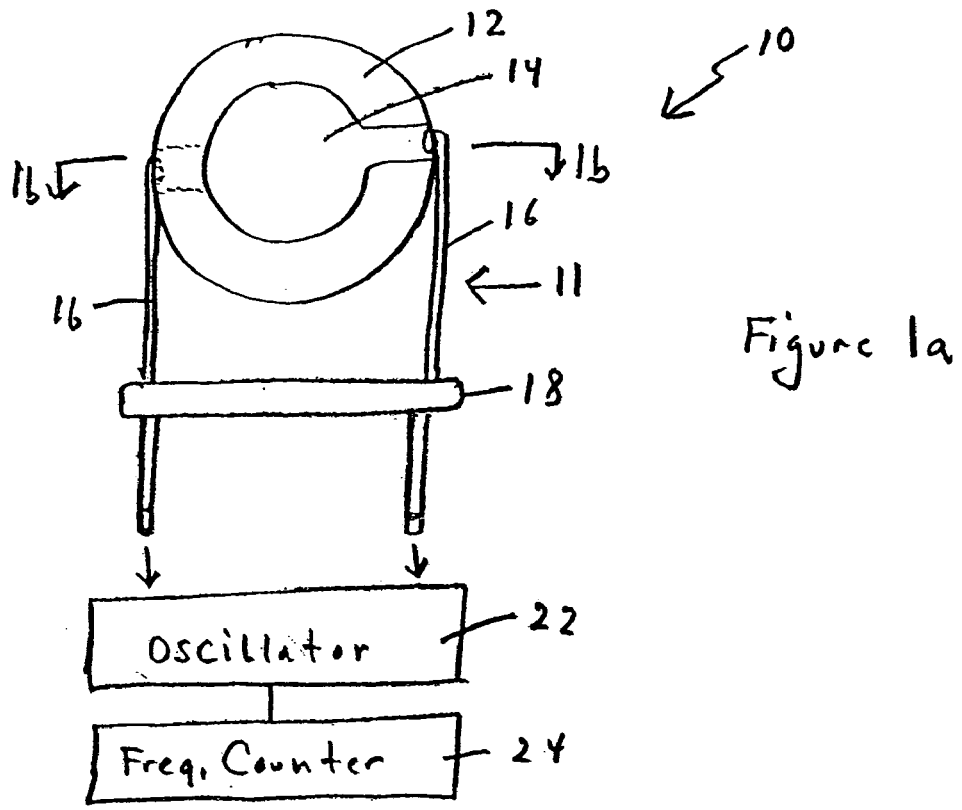
FIG. 1A shows a plan view of an apparatus 10 comprising a piezoelectric sensor device 11.

All patents, patent applications, government publications, government regulations, and literature references cited in this specification are hereby incorporated herein by reference in their entirety. In case of conflict, the present description, including definitions, will control.

The present invention provides an apparatus comprising one or more novel piezoelectric sensors to detect biological or chemical agents. The novel piezoelectric sensors comprising the present invention are based on principles similar to those of prior art piezoimmunosensor. In general, prior art piezoimmunosensors comprise a piezoelectric crystal integrated into a suitable electronic circuit to which whole antibodies specific for a particular analyte are immobilized on the surface of the piezoelectric crystal. In a preferred piezoimmunosensor such as that disclosed in U.S. Pat. No. 6,087,187 to Wiegand et al. provides that the crystal surface is coated with a thin layer of a precious metal such as gold. The gold coating simplifies the process for coating the piezoimmunosensor with antibody and regenerating after the antibody-antigen reaction has taken place.

The prior art piezoimmunosensors determine the presence of an analyte in a sample by measuring the change in weight on the surface of the sensor due to binding of analyte to the antibodies immobilized on the surface. The change in weight is measurable as a change in resonant frequency of the piezoelectric crystal (Sauerbrey, Phys. 155: 206 (1959)). However, as shown in FIGS. 2A to 2E, whole antibodies bound to the surface are randomly oriented which reduces the number of antibody molecules with analyte binding sites in the proper orientation to bind the analyte. In addition, the large size and branching arms of whole antibodies increase their susceptibility to proteases and non-specific binding and trapping of analyte. The random orientation and large size reduces the sensitivity and accuracy of prior art piezoimmunosensor. In general, the prior art piezoimmunosensors are used ex situ, that is the user adds the sample to the sensor, dries, and then measures the resonant frequency. Ex situ measurements are not real-time measurements.

In contrast to the prior art piezoimmunosensor, the piezoelectric sensor (piezoimmunosensor or device) of the apparatus of the present invention comprises a piezoelectric crystal wafer between one or more pairs of electrodes, each with a receptor layer thereon which provides a receptor surface to which a multiplicity of recombinant antibodies are immobilized thereon to form a lawn or monolayer, integrated into an oscillator circuit. In most applications, the receptor layer comprises the metal electrodes. Preferably, the receptor layer comprises a precious metal, preferably a noble metal such as copper, gold, palladium, platinum, silver, or titanium. In a preferred embodiment, the receptor layer comprises gold. The noble metal enables the recombinant antibodies to be bound via a particular group on the recombinant antibody. For example, when the surface is coated with gold, the recombinant antibodies can be bound via the thio group of a cysteine residue at the carboxyl termini of the recombinant antibodies. While the apparatus of the present invention can be used to take ex situ measurements, the apparatus can also be used to make real-time measurements.

Camelidae (camels, dromedaries and llamas) have a unique class of functional antibodies comprising only heavy chains. The heavy-chain antibody (HCAb) does not have a $C_H1$ domain, since the $C_H1$ is spliced out during mRNA processing. The antigen binding region of these antibodies are comprised of a single variable domain, designated $V_{HH}$, which is similar to $V_H$ domains in antibodies from other species as described by Nguyen et al., EMBO J. 19(5): 921-930, (2000). Technologies have been developed which take advantage of the functional $V_{HH}$ binding domains of these heavy-chain antibodies. The $V_{HH}$ domain can be cloned and isolated and still have functional binding capacity. These $V_{HH}$ are the smallest available intact antigen-binding fragments having a molecular weight of approximately 15 kiloDaltons (approximately 118 to 136 amino acid residues). For this reason they are sometimes referred to as "nanobodies". Functional $V_{HH}$ can be made by proteolysed HCAb of an immunized camelid, cloned $V_{HH}$ genes from immunized camelid B-cells, or from libraries. Phage display techniques can be used to select the $V_{HH}$ having the desired specificity. Other $V_H$ can be made more soluble and non-specific binding can be minimized by replacing amino acid residues therein with $V_{HH}$ residues or residues with similar chemical properties. This process is known in the art as "camelization."

In one embodiment of the present invention, the recombinant antibodies comprise in a single polypeptide chain a single $V_H$ chain, preferably derived from a library of camel or llama antibodies or camelized antibodies (Nuttall et al., Curr. Pharm. Biotechnol. 1: 253-263 (2000); J. Biotechnol. 74: 277-302 (2001)). In the case of the single $V_H$ chain polypeptides, the polypeptides can comprise the polypeptide sequence of a whole heavy chain antibody or only the amino terminal variable domain of the heavy chain antibody. In another embodiment, the recombinant antibodies comprise in a single polypeptide chain the variable light chain domain ($V_L$) linked to the variable heavy chain domain ($V_H$) to provide a single recombinant polypeptide comprising the Fv region of the antibody molecule (scFv). In a preferred embodiment, the recombinant scFv polypeptides include modifications such as an attachment polypeptide having particular amino acid residues or ligands which facilitate binding of the recombinant scFv polypeptide to the receptor surface of the piezoelectric material. Other embodiments of the recombinant antibodies include Fab fragments and those polypeptides illustrated in FIGS. 9C, 10, and 15. When various embodiments of the present invention are disclosed below, it is to be understood that when the term "recombinant scFv polypeptides" is used, the term not only includes scFv polypeptides but also includes the single $V_H$ chain polypeptides, Fab fragments, and those polypeptides shown in FIGS. 9C, 10, and 15.

Figure 1B:
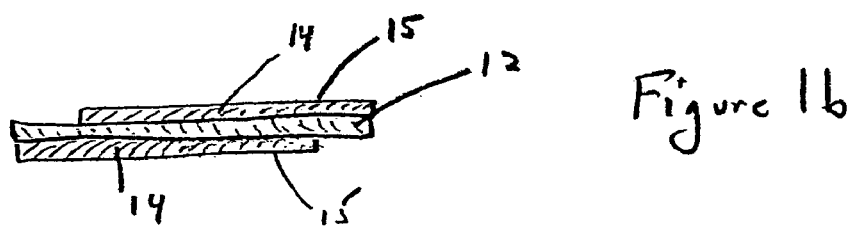
FIG. 1B is a side view of an apparatus 10 the piezoelectric sensor device 11 along line 1b in FIG. 1A.

FIGS. 1A and 1B schematically illustrates an embodiment of the apparatus comprising the present invention. As shown, the apparatus 10 comprises a device 11 which comprises a piezoelectric crystal wafer 12 between a pair of precious metal electrode coating or receptor layers 14 which provide receptor surfaces 15 for binding the recombinant single $V_H$ chain or scFv polypeptides. The most frequently used piezoelectric material is alpha quartz. These crystals are most suitable for piezoelectric application because they are insoluble in water and resistant to high temperatures. The resonant frequency of a quartz crystal wafer depends on the physical dimensions of the quartz wafer and the thickness of the electrode coating deposited thereon. AT and BT-cut crystals are most useful as piezoelectric detectors. These cuts refer to the orientation of the plate with respect to the crystal structure. The AT-cut crystal is the most stable. The crystals usually take the form of discs, squares, and rectangles.

A suitable crystal wafer 12 is a 5 to 10 MHz AT-cut quartz crystal with an electrode coating 14 deposited on each side of the crystal 12 using a suitable method such as the sputtering method. The piezoelectric crystal wafer 12 with the electrode coating 14 thereon is mounted to a base 18 using rigid metal leads 16 which support the crystal wafer on base plug 18. Preferably, the metal leads 16 are stainless steel and a silver composite is used to connect the electrode coating 14 to the metal lead 16. In a preferred configuration, the diameter of the crystal wafer 12 is greater than the diameter of the electrode coating 14. For example, the crystal wafer 12 can have a diameter of about 14 mm and the electrode coatings 14 on both sides of the crystal wafer 12 can have a diameter of about 8 mm. When the above device 11 is placed in an oscillator circuit provided by an oscillator 22, the portion of crystal wafer 12 between the electrodes 14 vibrates with its precise natural frequency. A mass mechanically attached to one or both of the electrodes 14 causes a downward shift in the fundamental or resonant frequency. The frequency of the crystal wafer 12 is monitored by a frequency counter 24 which is operably connected to the oscillator 22. In further embodiments, the apparatus 10 can include a plurality of devices 11, each operably connected to the oscillator 22. In further embodiments, crystal wafers having a plurality of electrode pairs deposited thereon can be used. In this embodiment, the portion of crystal wafer between each electrode pair has a characteristic frequency and one or both receptor surfaces of each electrode pair is bound to a particular recombinant scFv polypeptide.

Figure 1C:
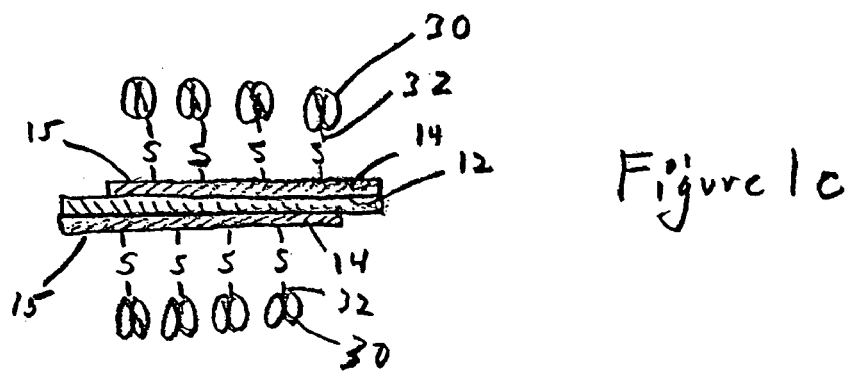
FIG. 1C is a side view of recombinant Fv polypeptides 30 bound to the receptor surface 15 of a gold receptor layer (electrode) 14 of the apparatus 10 of the present invention. In this Figure both electrodes 14 are bound to recombinant Fv polypeptides.
Figure 2A:
FIG. 2A shows monoclonal anti-TNT antibodies immobilized in a random orientation on silica fiber-optic probes via their primary amine groups.
Figure 2B:
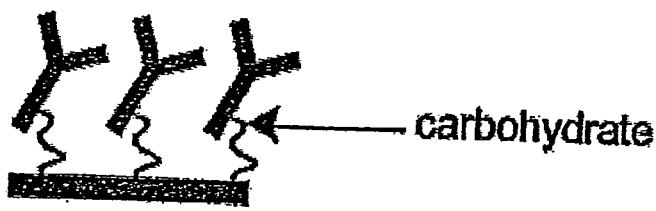
FIG. 2B shows monoclonal anti-TNT antibodies immobilized in a random orientation on silica fiber-optic probes via a carbohydrate moiety on the antibody's Fc domain.
Figure 2C:
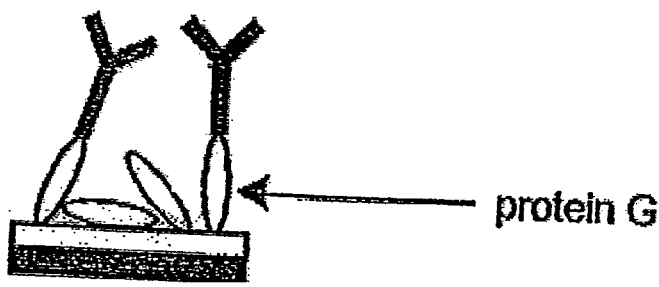
FIG. 2C shows monoclonal anti-TNT antibodies immobilized in a random orientation on silica fiber-optic probes via an intervening protein layer consisting of an unoriented protein G film.
Figure 2D:
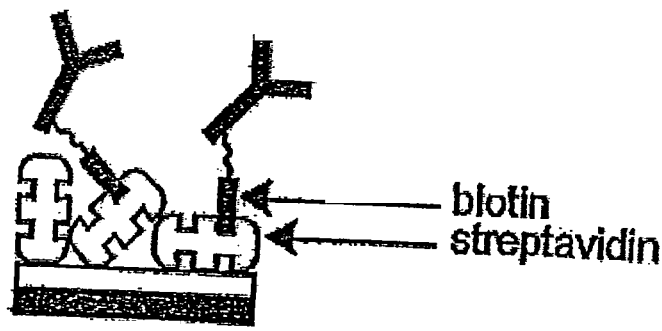
FIG. 2D shows monoclonal anti-TNT antibodies immobilized in a random orientation on silica fiber-optic probes via an intervening protein layer consisting of randomly oriented streptavidin layers.
Figure 2E:
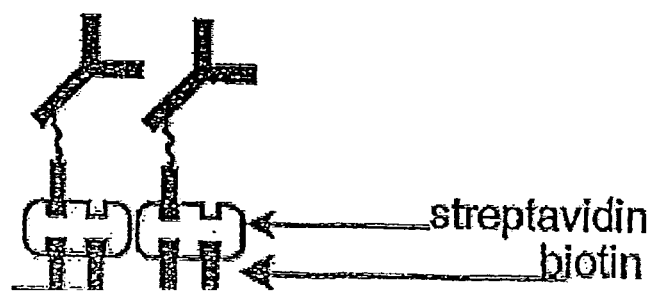
FIG. 2E shows monoclonal anti-TNT antibodies immobilized in a random orientation on silica fiber-optic probes via an intervening protein layer consisting of uniformly oriented streptavidin layers.

As shown in FIG. 1C, the recombinant scFv polypeptide 30 is bound to the receptor surface 15 by the sulfur group S at the carboxy terminus 32 of the recombinant scFv polypeptide 30.

Thus, in the present invention, the piezoelectric crystal of the sensor with the recombinant single $V_H$ chain or scFv polypeptides immobilized on the receptor layer has a particular resonant frequency which changes when one or more of the recombinant single $V_H$ chain or scFv polypeptides immobilized thereon are bound by analyte. This change in resonant frequency is a result of the increase in mass on the surface of the piezoelectric material caused by the binding of the analyte to the recombinant single $V_H$ chain or scFv polypeptide according to Sauerbrey's equation: $\Delta f = -Cf^2 \Delta m$ wherein $\Delta f$ is the change in resonant frequency in the oscillating crystal in Hz, f is the resonant frequency of the piezoelectric material in MHz, $\Delta m$ is the change in mass per unit area (g/cm$^2$), and C is a constant which is dependent on the composition of the piezoelectric material. For example, C is $2.3 \times 10^6$ for AT-cut quartz crystals vibrating in the thickness shear mode.

Digital frequency counters to measure the oscillator signal are equally suitable for fabrication as lightweight components of field instruments. The frequency measurements are also beneficial because frequency is one of the most precisely measurable quantities with precision of about $1:10^{10}$. The apparatus can be easily automated or combined with flow injection systems extending their capability for continuous and repeated assays. This enables the ability of using crystal arrays to assay different analytes in complex samples with on-line display of the results. The piezoelectric sensors comprising the present invention open up new avenues in ultra-sensitive analysis of trace substances in complex biological systems and are expected to replace current immunoassay technologies. The present invention is useful for a wide variety of immunoassays including bioterrorism defense, environmental pollutant monitoring, forensic analysis, biological research, and routine clinical tests in laboratory medicine.

Piezoelectric sensors which can be adapted for use in the apparatus of the present invention can be found in U.S. Pat. No. 4,236,893 to Rice, U.S. Pat. No. 4,242,096 to Oliveira et al., U.S. Pat. No. 4,246,344 to Silver III, U.S. Pat. No. 4,314,821 to Rice, U.S. Pat. No. 4,735,906 to Bastiaans, U.S. Pat. No. 5,314,830 to Anderson et al., U.S. Pat. No. 5,932,953 to Drees et al., and U.S. Pat. No. 6,087,187 to Wiegland et al.

Because of the sensitivity of the piezoelectric sensor, the sensor immediately detects the presence of an antigen as it binds to the specific recombinant scFv polypeptide and displays that information as a change in resonant frequency. The advantages of the piezoelectric sensors comprising the apparatus of the present invention include that they are small, portable, and inexpensive; they provide real time output and high sensitivity; they provide simultaneous and continuous analysis of multiple analytes; no sample preparation by the user is required; and, and no secondary label is needed to establish identification. Thus, the present invention provides a reliable piezoelectric sensor with significant advantages over current biosensor technology.

Measurement of frequency shifts is one of the most accurate types of physical measurement. Since the recombinant single $V_H$ chain or scFv polypeptide-antigen binding is highly specific, a frequency shift reveals exactly what analyte is present. As taught herein, the recombinant single $V_H$ chain or scFv polypeptide enables a functionalized film to be formed which is thin, rigid, has high density of biorecognizing elements, and is highly sensitive and selective. Site-directed mutagenesis can also be used to manipulate the DNA encoding a recombinant single $V_H$ chain or scFv polypeptide to produce immunoreactive polypeptides which do not occur naturally. Recombinant single $V_H$ chain or scFv polypeptide cross-reactivity can be minimized by designing two separate sensors for each antigen, each with a recombinant single $V_H$ chain or scFv polypeptide specific for a different surface epitope on the same antigen. Thus, detection of the analyte is confirmed when both sensors indicate binding of the analyte.

The piezoelectric sensor comprising the apparatus of the present invention takes advantage of several developing fields: (1) single $V_H$ chain polypeptides such as those derived from heavy chain antibodies which occur in camel, llama, or camelized antibody libraries, (2) the field of single-chain recombinant Fv polypeptides (recombinant scFv polypeptides), and (3) the field of self-assembled monolayers (SAM).

Figure 3:
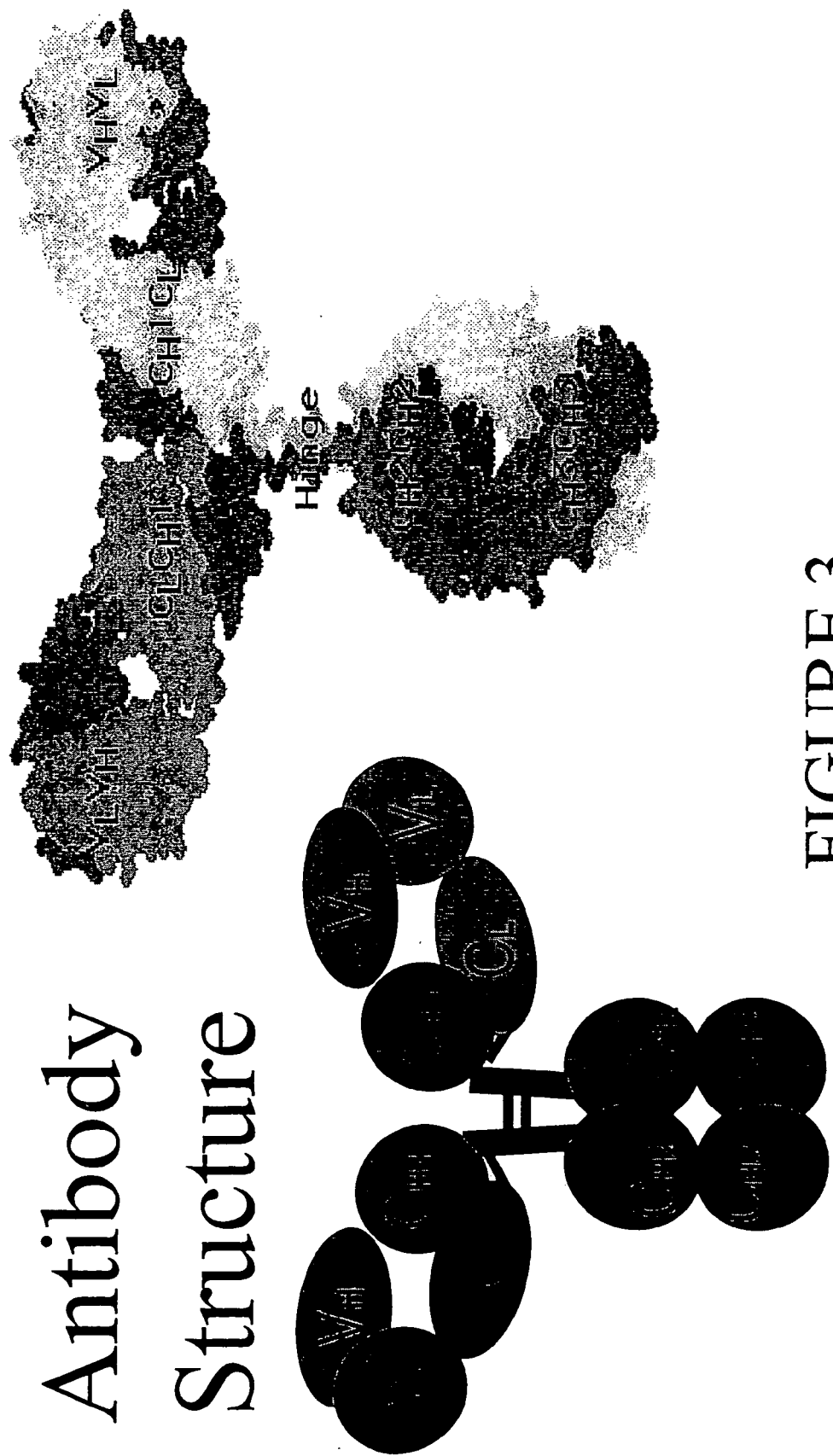
FIG. 3 shows the structure of an antibody molecule showing the variable region ($V_L$) and constant region($C_L$) of the light chain and the variable region ($V_H$) and constant regions ($C_{H1}$, $C_{H2}$, and $C_{H3}$) of the heavy chain.
Figure 4:
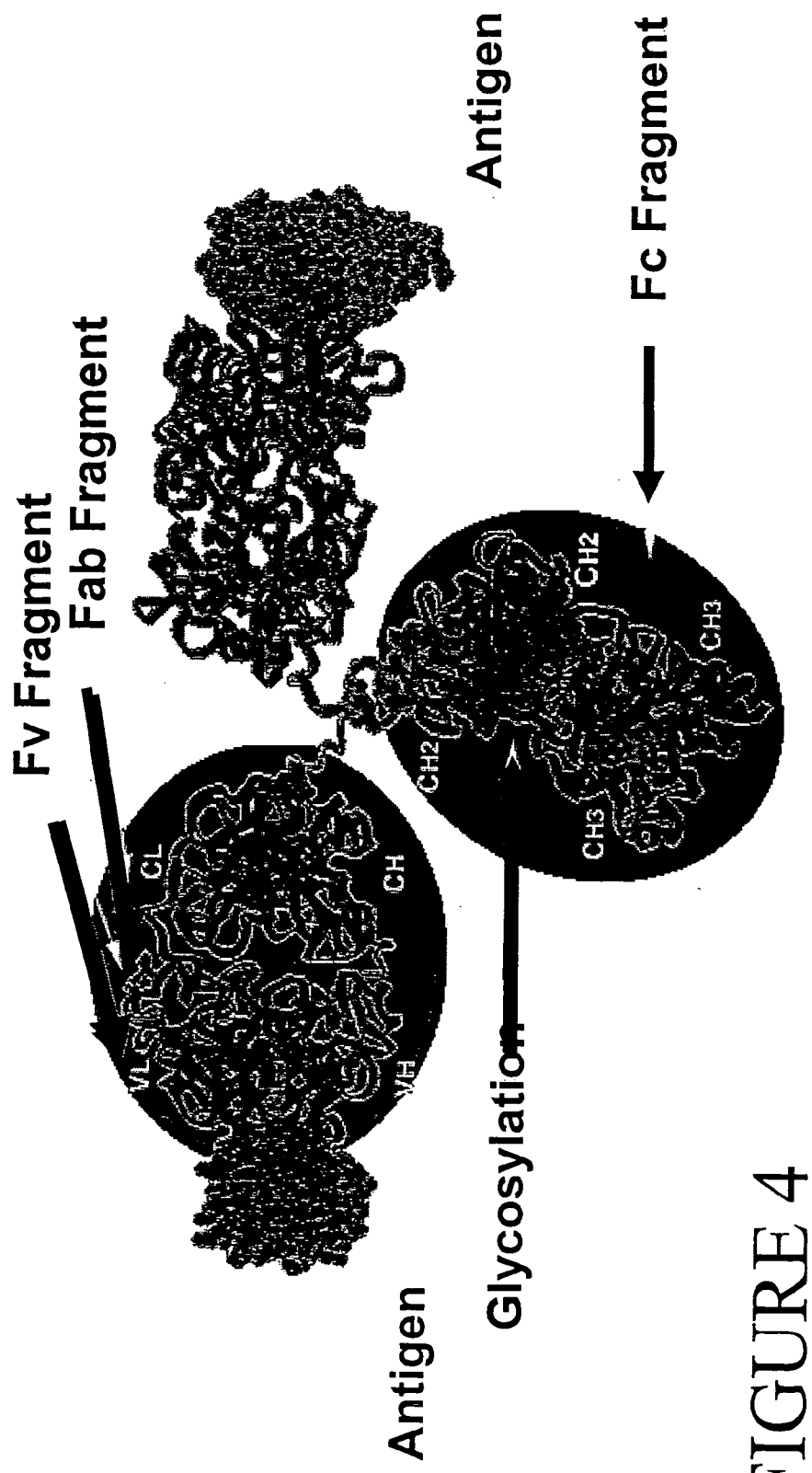
FIG. 4 shows the structure of an antibody molecule bound to an antigen with the Fv, Fab, and Fc fragments identified.
Figure 5:
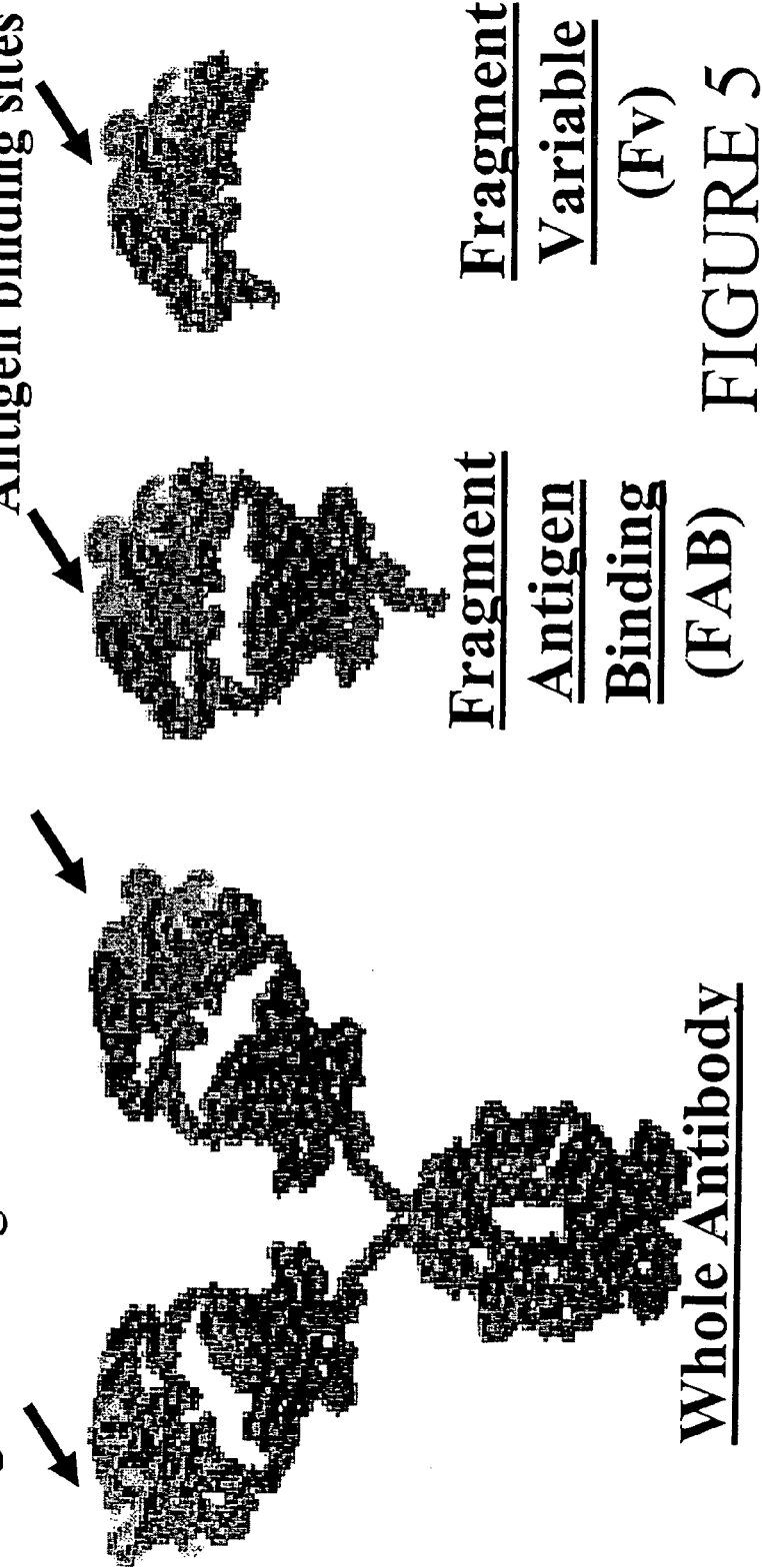
FIG. 5 shows a comparison of the whole antibody molecule to the Fab to the Fv.
Figure 6:
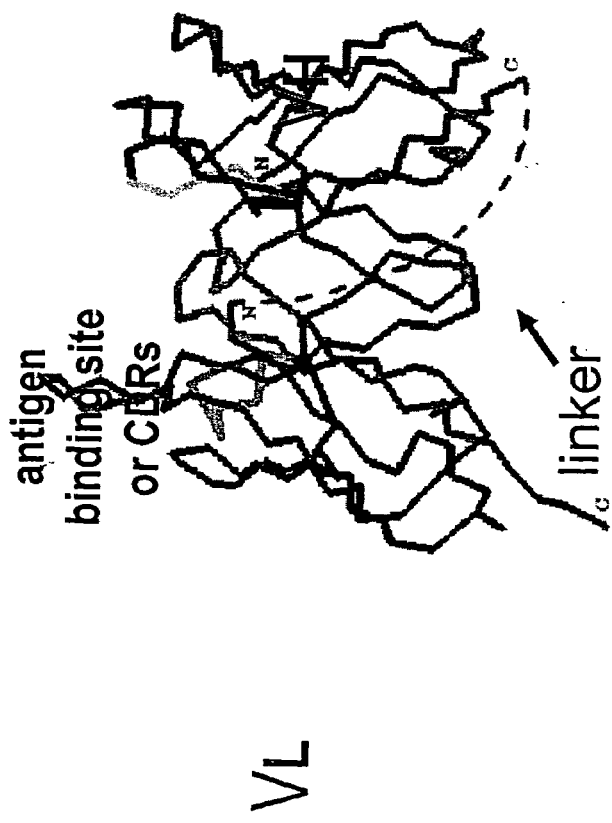
FIG. 6 shows a recombinant scFv polypeptide wherein the amino terminus of the $V_L$ chain is linked via a polypeptide linker to the carboxy terminus of the $V_H$ chain which preserves the antigen binding site of the Fv.

Fv fragments of immunoglobulins are the smallest functional portions of a typical antibody required for high-affinity binding of antigen. Fv fragments are small heterodimers consisting of the heavy-chain variable domain and the light chain variable domain. FIG. 3 shows the structure of an antibody molecule. An antibody molecule consists of two arms, each arm consisting of a light chain and a heavy chain. Each light chain consists of a variable domain ($V_L$) and a constant domain ($C_L$) and each heavy chain consists of a variable domain ($V_H$) and constant domains $C_{H1}$, $C_{H2}$, and $C_{H3}$. The light and heavy chains are held in the proper orientation by an intermolecular disulfide bond between the $C_L$ and $C_{H1}$ domains and the arms are held in the proper orientation by intermolecular disulfide bonds between the $C_{H2}$ and $C_{H3}$ domains of the heavy chains. FIG. 4 shows the structure of an antibody molecule bound to an antigen with the Fv, Fab, and Fc regions identified. The Fv region consists of the $V_L$ and $V_H$ domains; the Fab consists of the light chain $V_L$ and $C_L$ domains linked to the $V_H$ and $C_{H1}$ domains of the heavy chain by the disulfide bond between the $C_L$ and $C_{H1}$ domains; and the Fc consists of the $C_{H2}$ and $C_{H3}$ domains of each arm linked via disulfide bonds. A comparison of the whole antibody molecule to the Fab to the Fv fragments is shown in FIG. 5. The amino acid backbone and spacefill model of a recombinant scFv polypeptide is shown in FIG. 6. In a recombinant scFv polypeptide, the amino terminus of the $V_L$ chain is linked via a polypeptide linker to the carboxy terminus of the $V_H$ chain which preserves the antigen binding site of the Fv.

Recombinant single $V_H$ chain or scFv polypeptides are small (about 27 kDa), which allows a high density of them to be immobilized on a surface while preserving their stability and specificity. Since only the analyte binding region of the antibody is present, nonspecific interactions due to the presence of the constant regions of the antibody are eliminated. The recombinant single $V_H$ chain or scFv polypeptide used herein preferably includes an attachment polypeptide at the carboxy terminus of the polypeptide which contains a polypeptide sequence, one or more amino acid residues, or other group which enables an ordered layer of the recombinant scFv polypeptides to be immobilized on the receptor surface of the piezoelectric material. Methods for constructing recombinant scFv polypeptides can be found in Schmiedl et al., J. Immunol. Meth. 242: 101-114 (2000); Schultz et al., Cancer Res. 60: 6663-6669 (2000); Dubel et al., J. Immunol. Meth. 178: 201-209 (1995); and in U.S. Pat. No. 6,207,804 B1 to Huston et al.

Recombinant single $V_H$ chain or scFv polypeptides offer significant advantages over polyclonal or monoclonal antibodies for immunochemical detection of antigens. Polyclonal antibodies are difficult to use because of their heterogeneous nature. Monoclonal antibodies afford homogeneous binding characteristics, but monoclonal antibody production is labor intensive and expensive. Furthermore, the large size and branching arms of whole antibodies increase their susceptibility to proteases and non-specific binding and trapping of antigen. Further still, because of the small size of the recombinant scFv or single $V_H$ chain polypeptides, it is easier to produce a thin, rigid, and uniform film on a surface, thus maximizing the quantitative information of the recombinant single $V_H$ chain or scFv polypeptide-antigen binding event, which in the case of the present invention, can be detected by the change in resonant frequency. In addition, because of their small and uniform size, which is due to the lack of the branching arms of whole immunoglobulins, and their adaptability to genetic and protein engineering as fusion proteins which incorporate reactive residues for directional binding, recombinant single $V_H$ chain or scFv polypeptides provide significant advantages over the antibodies used in prior art piezoimmunosensors.

Furthermore, the high affinity of a recombinant single $V_H$ chain or scFv polypeptide for its analyte makes it a very versatile analytical reagent capable of reacting specifically with analytes at very low concentrations and in complex solutions such as serum. Additionally, recombinant single $V_H$ chain or scFv polypeptides for a wide range of analytes can be obtained easily through currently available molecular techniques such as phage display (de Haard et al., J. Biol. Chem. 274: 18218-18230 (1999); Saviranta et al., Bioconjugate 9: 725-735 (1999); de Greeff et al., Infect. Immun. 68: 3949-3955 (2000)) or polypeptide synthesis. The small size of single $V_H$ chain or recombinant scFv polypeptides allow them to be constructed with a variety of attachment polypeptides making formation of a SAM layer relatively easy.

The use of SAMs is a rapidly developing field for creating an interface-layer between a metal surface and a solution or vapor. A SAM is formed by the spontaneous association of molecules under equilibrium conditions. This spontaneous association yields a stable, structurally well-defined two-dimensional aggregate on the surface. For example, it has previously been shown that long chain alkanethiols (number of methylene groups n is greater than 10) assemble in a crystalline-like way. A perfectly aligned, closely-packed, rigid film can be made by self-assembly of sulfur-containing molecules on a metal (for example, gold). Consequently, SAMs are inherently manufacturable on a large scale.

Immobilization of a thin, rigid film is of paramount importance for the piezoimmunosensor. However, in the case of immobilizing whole antibodies or fragments thereof (for example, Fv or Fab fragments) to a surface, adsorption of the antibodies to the surface produces a randomly orientated film in which not all analyte binding sites are available for binding and in which the antibodies can pile up on each other (See FIGS. 2A to 2E). Thus, an uneven film is produced in which not all analyte binding sites are available for binding. This distorts the relationship between mass change with frequency change. The above problem can also occur when recombinant single $V_H$ chain or scFv polypeptides are substituted for the whole antibodies or fragments thereof. Therefore, in order to preserve the biological activity of the recombinant single $V_H$ chain or scFv polypeptides after immobilizing on the receptor surface of the receptor layer on the piezoelectric crystal wafer and to preserve the linear relationship of mass change with frequency change of the sensor, a smooth lawn of recombinant single $V_H$ chain or Fv polypeptides must be deposited onto the receptor surface of the receptor layer on the piezoelectric crystal wafer and a substantial number of the recombinant single $V_H$ chain or scFv polypeptides must be in an orientation which enables the binding site to bind the analyte.

The present invention provides a solution to the above problem. The recombinant single $V_H$ chain or scFv polypeptides are designed to include an attachment polypeptide linked to the carboxy terminus of the polypeptide which comprises one or more reactive amino acid residues, binding site, or other group which enables formation of an ordered lawn or monolayer, on the receptor surface of the receptor layer on the piezoelectric crystal and which also allows the proper orientation of the recombinant single $V_H$ chain or scFv polypeptide such that the analyte binding site on each is available for binding analyte. Thus, the process for producing the lawn or monolayer preferably involves creating self-assembling monolayers (SAM) of recombinant single $V_H$ chain or scFv polypeptides in which the recombinant scFv polypeptides are bound to the surface of the receptor layer on the piezoelectric material in such a way as to provide optimal orientation of the antigen-binding region of the recombinant scFv polypeptide and to provide a continuous lawn of the recombinant single $V_H$ chain or scFv polypeptides. The continuous lawn prevents non-specific interactions or trapping of analyte molecules as can occur in the case of using whole antibodies or Fab fragments thereof.

In some embodiments, the receptor layer for binding the recombinant single $V_H$ chain or scFv polypeptides is deposited on the surface of the electrode on the surface of the piezoelectric crystal wafer. The receptor layer can be a diamond layer, a protein layer, or a metal different from the metal comprising the electrode such as copper, gold, silver, palladium, platinum, silver, or titanium. However, in a preferred embodiment, the receptor layer for binding the recombinant single $V_H$ chain or scFv polypeptides is the gold electrode on the surface of the piezoelectric crystal wafer. The surface of the electrode provides the receptor surface. In addition, the recombinant single $V_H$ chain or scFv polypeptides each have a cysteine residue at the carboxyl terminus of the $V_L$ domain or attachment polypeptide. The terminal cysteine binds the receptor surface of the gold electrode on the piezoelectric crystal. This provides a continuous lawn of the recombinant single $V_H$ chain or scFv polypeptide in which the analyte binding portion of the recombinant scFv polypeptide is oriented away from the surface of the electrode on the piezoelectric crystal thereby maximizing the number of binding sites in the lawn available for binding analyte.

Figure 8:
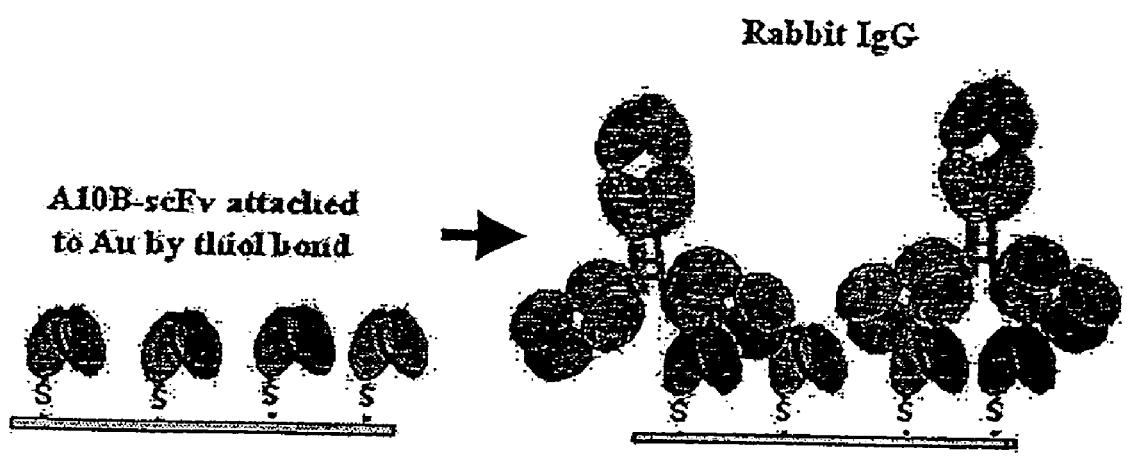
FIG. 8 shows a cartoon of A10B-scFv capturing rabbit IgG. (a) A10B-scFv with cysteine or histidine residue incorporated into the linker. A10B-scFv recognizes the constant heavy chain1 (CH1) domain of rabbit IgG. (b) Rabbit IgG with the CH1 domain labelled.

FIG. 7 shows an embodiment of a piezoelectric biosensor comprising the present invention wherein the piezoelectric crystal is a quartz crystal microbalance with a gold electrode receptor layer and each of the recombinant scFv polypeptides further includes an attachment polypeptide which provides the recombinant scFv polypeptide with a terminal cysteine residue which binds the receptor surface of the receptor layer. As shown in FIG. 7, the terminal cysteine residue binds to the receptor surface which results in the self-assembly of the recombinant scFv polypeptides into a lawn or monolayer of the recombinant scFv polypeptides on the receptor surface. FIG. 8 shows a cartoon of A10B-scFv capturing rabbit IgG.

Figure 10:
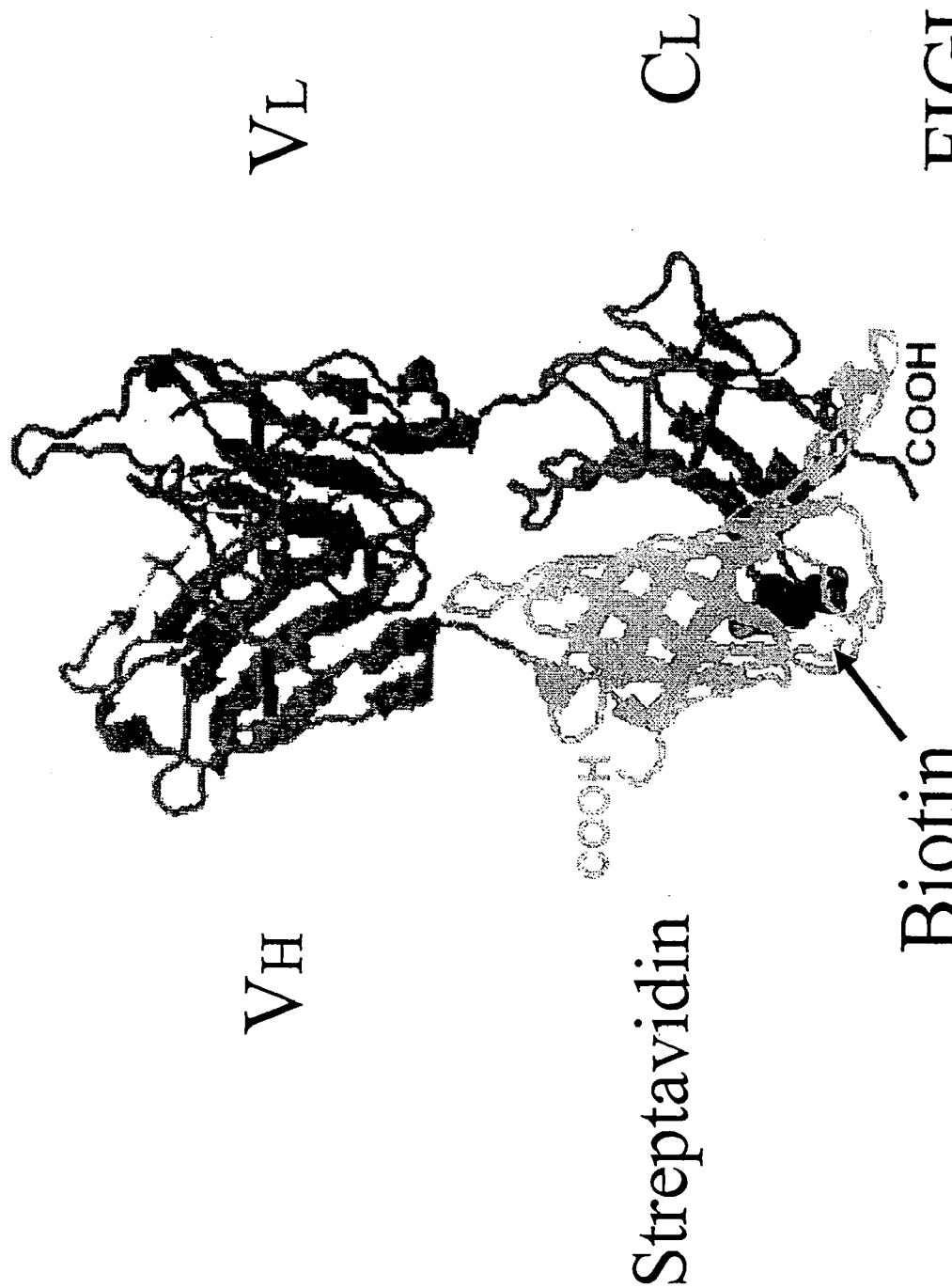
FIG. 10 shows the structure of a streptavidin-Fab complex comprising a $V_H$ chain linked to a streptavidin and the $V_L$ and $C_L$ chain wherein the streptavidin binds the $C_L$ such that the $V_H$ and $V_L$ chains are held in an orientation which allows binding to the antigen.

Other strategies for producing a lawn or monolayer of recombinant scFv polypeptides on the receptor surface of a piezoelectric material are shown in FIGS. 9A to 12. FIGS. 9A-9C show several alternative strategies for binding recombinant scFv polypeptides to the surface of a receptor layer on a piezoelectric crystal wherein the receptor layer is a gold electrode. The common element to these strategies is that biotin molecules, which have been designed to have a cysteine at the carboxy terminus, are self-assembled into a lawn or monolayer on the receptor surface of the gold electrode on the piezoelectric crystal. In FIG. 9A, the recombinant scFv polypeptide has a carboxy terminal strep-tag which binds to streptavidin which is also bound to the biotin lawn. In FIG. 9B, the carboxy terminus of the recombinant scFv polypeptide has a biotin tag which binds to streptavidin which is also bound to the biotin lawn. In FIG. 9C, a streptavidin-Fab complex is bound to the biotin lawn. FIG. 10 shows the structure of the streptavidin-Fab complex. The complex comprises a first recombinant polypeptide comprising a $V_H$ domain polypeptide linked to a streptavidin polypeptide and a second recombinant polypeptide comprising the $V_L$ and $C_L$ domains wherein the streptavidin binds the $C_L$ such that the $V_H$ and $V_L$ chains are held in an orientation to form an analyte binding site.

Figure 11:
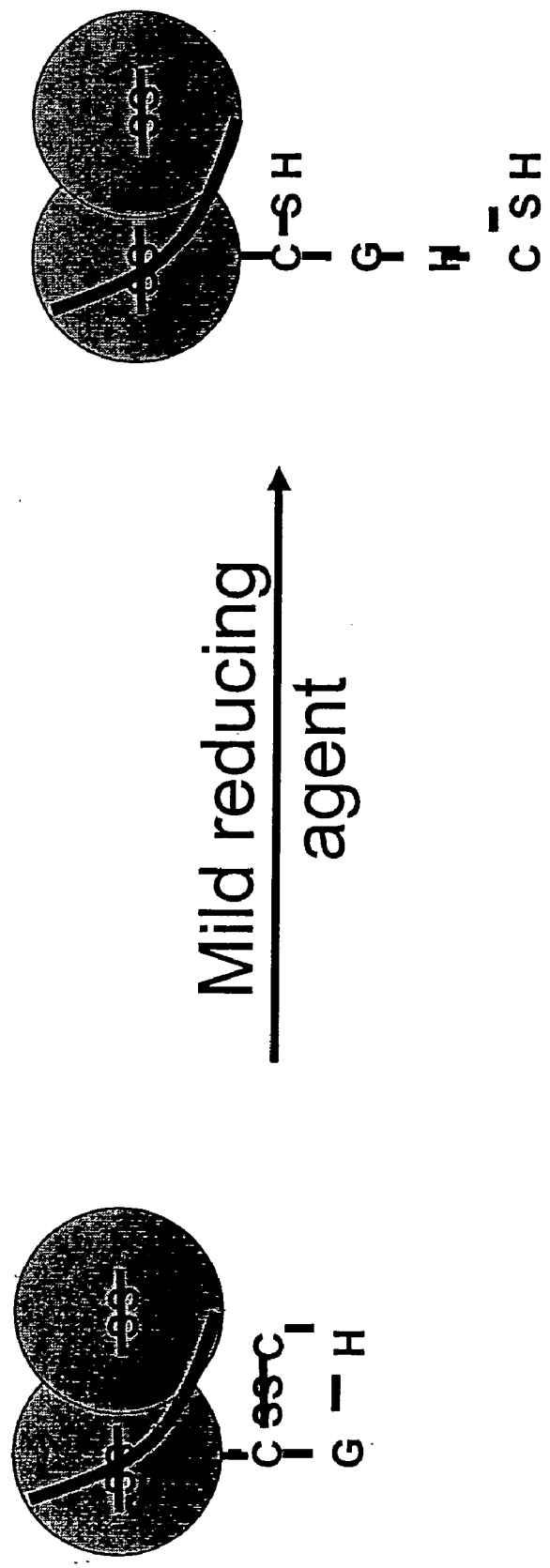
FIG. 11 shows an alternative strategy wherein the attachment polypeptide of the recombinant scFv polypeptide contains an internal and an external cysteine which forms a disulfide bond. Treating with a mild reducing agent reduces the disulfide which makes the terminal cysteine available for binding to the gold-coated surface of a piezoelectric material.

In a further embodiment as shown in FIG. 11, the attachment polypeptide of the recombinant scFv polypeptide contains internal and external cysteine residues which form an intramolecular disulfide bond. Treating the recombinant scFv polypeptide with a mild reducing agent reduces the disulfide bond which makes the terminal cysteine available for binding to the receptor surface of a gold electrode on the piezoelectric crystal.

Figure 12:
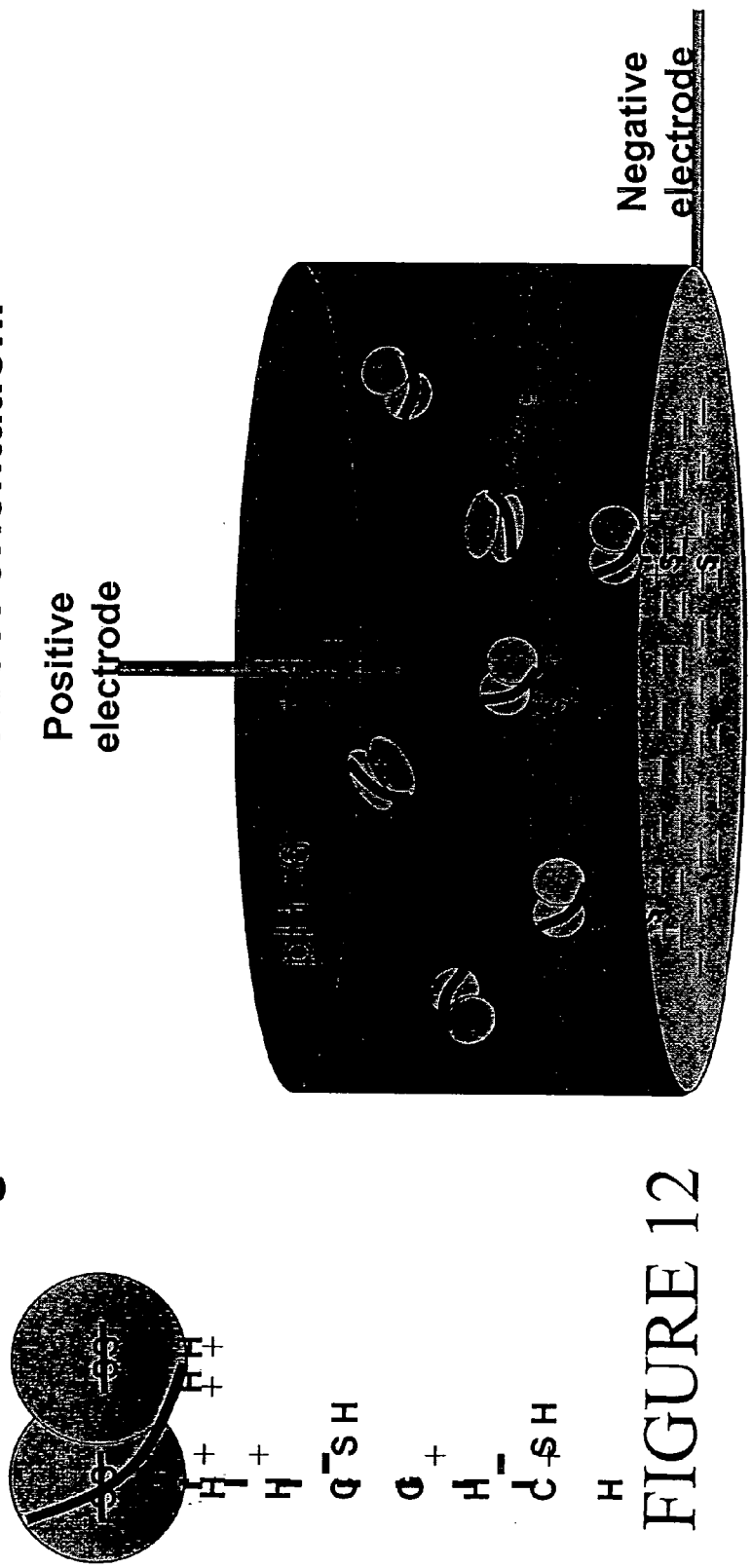
FIG. 12 shows an alternative strategy for binding the recombinant scFv polypeptide to the surface of the piezoelectric material. The attachment polypeptide contains charged residues which enable the recombinant scFv polypeptide to bind to the surface of piezoelectric material in the correct orientation.

A further still embodiment for forming the lawn is shown in FIG. 12. The attachment polypeptide contains charged residues which enable the recombinant scFv polypeptide in a solution to bind to the receptor surface on the piezoelectric crystal in the correct orientation when the surface is a negative electrode and a positive electrode is inserted into the solution.

Other methods for attaching substances to surfaces which can be adapted to attach the recombinant scFv polypeptide to the receptor surface of piezoelectric material are described in U.S. Pat. No. 6,475,809 to Wagner et al., U.S. Pat. No. 6,475,808 to Wagner et al., U.S. Pat. No. 6,368,877 to Zhang et al., U.S. Pat. No. 6,319,674 B1 to Fulcrand et al., and U.S. Pat. No. 5,622,826 to Varma, and Yang et al., Nature Materials 1: 253-257 (2002).

Recombinant single $V_H$ chain or scFv polypeptides specific for a variety of known antigens can be produced and by using the method herein, each bound as SAMs to a receptor surface on a piezoelectric crystal to provide a plurality of piezoelectric sensors, each with a particular recombinant single $V_H$ chain or scFv polypeptide bound thereon specific for detecting a particular analyte and having a characteristic resonant frequency. The plurality of piezoelectric sensors can be assembled into an array of sensors in an apparatus for detecting a plurality of analytes. For example, the apparatus can include one piezoelectric sensor for detecting anthrax, a second for detecting *salmonella*, a third for detecting botulism toxin, and so on.

In another embodiment, the apparatus for detecting a plurality of analytes comprises a single piezoelectric sensor in which the piezoelectric crystal comprises a plurality of electrode pairs, the receptor surfaces of each pair coated with a lawn or monolayer of a particular recombinant scFv polypeptide. The portion of piezoelectric crystal between each electrode pair will have a characteristic frequency. Thus, a single sensor can be fabricated which detects more than one analyte.

Current QCM sensors detect mass changes in liquid or gas phases by monitoring the frequency of the immersed crystal directly or with respect to an external reference crystal. It is important to note that as the temperature of the bathing fluid changes during the course of an experiment, the bathing fluid's viscosity and density also change. This causes a shift in the immersed crystal's frequency. To enable these changes in viscosity and density to be compensated for in an experiment, a further embodiment of the present invention the apparatus is a dual quartz crystal microbalance (DQCM) which in addition to the foregoing sensing sensors further comprises a control or reference piezoelectric mass sensor for detecting fluctuations in density and viscosity which might occur during a measurement. The control piezoelectric mass sensor comprises at least one receptor layer which provides a receptor surface and which has immobilized on the receptor surface a layer of recombinantly derived polypeptide molecules which bind the analyte, wherein each of the molecules comprises a single antibody variable heavy chain ($V_H$) or single-chain Fv (scFv) polypeptide specific for the analyte and an attachment polypeptide having a sequence which provides assembly of the molecules into the layer so as to be immmobilized on the receptor surface wherein binding of the analyte is blocked by a blocking agent. For the control, the analyte binding site of the single antibody variable heavy chain ($V_H$) or single-chain Fv (scFv) polypeptide on the control is blocked with a blocking agent such as oligo(ethylene glycol) which is inert to absorption of protein. When submerging the apparatus into a sample, the frequency difference between the submerged control and sensing sensors is monitored and the frequency of the sensing sensor is adjusted by a mixer in the oscillator circuit between the control and sensing sensors which compensates for frequency changes which might occur because of changes in viscosity or density of the sample during the measurement time period.

The piezoelectric sensors can be regenerated after a use by using different pH washing solutions to decouple the analyte bound to the immobilized recombinant single $V_H$ chain or scFv polypeptides or to decouple the analyte-recombinant single VH chain or scFv polypeptides from the surface and adding a new layer of recombinant single $V_H$ chain or scFv polypeptides. However, because the piezoelectric sensors are inexpensive and easy to prepare, they can also be designed to be one-use only or disposable.

The piezoelectric sensors comprising the present invention allow the production of an inexpensive, easy-to-use sensors, which provide fast, real-time precise identification of biological agents in samples. The sensors can be easily automated or combined with flow injection systems which will allow the use of arrays of the sensors, each reactive to a different biological agent (for example, anthrax, HIV, and the like). These arrays could assay for specific agents in complex samples with on-line display of the results. Optimization of the immobilization of recombinant scFv polypeptides easily satisfies the important prerequisite for mass production of sensors and will lead to a highly reliable piezoelectric sensor with significant advantages over those using current piezoelectric sensor technology. The sensitivity is such as to be able to detect binding of a single specific antigen, toxin, or virus particle. The process for producing the SAM provides a means for producing an inexpensive, easy to-use sensor which provides fast, precise identification of biological agents in real time.

The following examples are intended to promote a further understanding of the present invention.

EXAMPLE 1

This example provides an illustration of a method for making a piezoelectric sensor for detecting human $IgG_2$. The sensor comprises recombinant scFv polypeptides of the Fv of a mouse monoclonal antibody specific for constant 1 domain of the human $IgG_2$ heavy chain with a carboxy cysteine immobilized on the gold receptor surface of a commercially available quartz AT crystal via the sulfur of the carboxy cysteine residue.

The mouse hybridoma producing the anti-human $IgG_2$ monoclonal antibodies was CRL-1752 which was obtained from the American Type Culture Collection, 10801 University Boulevard, Manassas, Va.

The genes encoding the variable is accomplished using standard molecular biology methods. RNA is extracted from hybridoma cells and reverse transcribed to make a cDNA copies of the RNA. Then, the cDNA is PCR amplified with degenerate oligonucleotide primers, one set of primers for amplifying the VH domain and another set of primers for amplifying the VL domain. Each primer set consists of one 3' primer which corresponds to a nucleotide sequence in the constant domain and about ten degenerate primers corresponding to a nucleotide sequence at the amino end of the variable region. Thus, each primer set will produce a PCR product comprising a DNA encoding the variable domain and all or a portion of the adjacent constant domain. The primer set for PCR amplification of the heavy chain of the mouse monoclonal antibody specific for α-human $IgG_2$ comprises a 3' primer (SEQ ID NO:1) corresponding to a sequence in the $C_{H1}$ domain and a degenerate set of ten 5' primers corresponding to the $V_H$ region (SEQ ID NO:2, 3, 4, 5, 6, 7, 8, 9, 10, 11). The primer set produces a DNA encoding the $V_H$ and $C_{H1}$ domains. A similar primer set is used to PCR amplify the $V_L$ and $C_L$ domains. After amplification, the PCR products are ligated into plasmid cloning vectors which are then transformed into $E.\ coli$. EcORI digests of $E.\ coli$ clones produced by the above procedure produced DNA encoding the $C_{H1}$ and $V_H$ of the heavy chain and DNA encoding the $C_L$ and $V_L$ of the light chain of the mouse monoclonal antibody. The 5' VH sequence has the sequence 5'CAGCTGAAGGAGTCAGGACC (SEQ ID NO:12) which corresponded to degenerate PCR primer 5' VHb (SEQ ID NO:3).

DNA encoding a recombinant scFv polypeptide derived from the mouse monoclonal antibody and including a cysteine linked to the carboxy terminus of the $V_L$ was constructed from the above cloned PCR products. The $V_H$ domain is PCR amplified from the above $V_H$-$C_{H1}$ clone using a 5' primer containing a KasI cleavage site and a 3' primer containing codons for an amino acid linker and terminated with an XhoI cleavage site. The KasI site is located such that when the KasI site is cleaved and the PCR product inserted into an expression vector, the codons encoding the $V_H$ domain are in frame with the codons in the expression vector. The $V_L$ domain is PCR amplified from the above $V_L$-$C_L$ clone using a 5' primer containing a XhoI cleavage site followed by codons for an amino acid linker which are in frame with the codons encoding the $V_L$ domain and a 3' primer containing in frame a codon for cysteine followed by a KasI cleavage site. The XhoI site is located such that when the XhoI site is cleaved and its cut end ligated to the cleaved XhoI site at the 3' end of the $V_H$ domain, the codons for the $V_H$ domain, the amino acid linker, and the $V_L$ domain are all in frame. This produced the recombinant scFv polypeptide with nucleotide sequence SEQ ID NO:13.

Plasmid pASK-IBA6 was the expression vector used for cloning the recombinant scFv polypeptide. Plasmid pASK-IBA6 or comparable expression vectors are particularly useful for producing recombinant scFv polypeptides because the OmpA promoter enables the recombinant scFv polypeptides to be preferentially expressed in the periplasma and the strep-tag enables the recombinant scFv polypeptides to be readily isolatable from the periplasma. After isolation, the strep-tag is readily removable from the recombinant scFv polypeptide.

After the recombinant scFv polypeptide is isolated from the periplasma and the strep-tag removed, the recombinant scFv polypeptide is dissolved in a suitable aqueous solvent and applied to the gold receptor surfaces of the gold electrode pair on the commercially available piezoelectric crystal which is integrated in a suitable oscillator circuit such as that shown in FIG. 1A for a time sufficient to bind the recombinant scFv polypeptide thereto. The sulfur group of the terminal cysteine binds to the gold receptor surface forming a correctly oriented, thin, tightly packed monolayer of the recombinant scFv polypeptides on the surface of the gold receptor surface on the quartz crystal as shown in FIG. 7. After the monolayer has been formed, the surface is washed with a washing solution to remove unbound recombinant scFv polypeptides.

For use, the resonant frequency of the sensor is determined and the sensor then incubated with the sample either by dipping in a liquid sample, by application of the liquid sample to the surface of the sensor, or in a liquid, vapor, or gas sample under continuous flow conditions. Afterward a sufficient period of time has elapsed, the resonant frequency of the sensor is measured. A change in resonant frequency indicates that the sample contains the analyte and the degree of change in resonant frequency indicates the quantity of analyte captured by the recombinant scFv polypeptides.

EXAMPLE 2

This example illustrates the general method for making a piezoelectric sensor.

Current biosensors provide accurate detection but have significant disadvantages in terms of cost, time needed for detection, lack of portability, ability to function in a "dirty" environment, and the need for highly trained technicians to operate the systems. Piezoimmunosensor (PZ) technology, which places antibodies on a quartz crystal microbalance (QCM) to detect minute changes in mass as the antibodies bind with antigens, can address these drawbacks. However, use of PZ technology in biosensors is problematic due to the complex nature of whole antibodies, which causes problems with non-specific interactions and molecule trapping.

The present invention is a highly sensitive and specific PZ biosensor which uses recombinant single-chain antibody variable fragments (Fv). The Fvs are engineered so as to form a "lawn" of antigen-binding sites coating the surface of the QCM. This involves creating self-assembling monolayers (SAM) of Fvs that bind to the gold surface of the QCM in such a way as to assure optimal orientation of the antigen-binding region of the Fv and provide a continuous monolayer, which prevents non-specific interactions or trapping of molecules. The antigen-binding event is detected by the QCM, which is able to detect binding of a single specific toxin or virus particle.

The present invention allows for the production of an inexpensive, easy-to-use biosensor which provides fast, precise identification of biological agents. Fvs specific for a variety of known antigens could be produced and, using our process, bound as SAMs to a QCM. Each specific type of Fv can be attached to a different QCM to form an array of sensors. For instance, one QCM could detect anthrax, another *salmonella*, another botulism toxin, etc. The sensor will immediately detect the presence of an antigen as it binds to the specific Fv monolayer and display that information. Such a biosensor would be small, portable, and inexpensive. It would provide real time output and high sensitivity. It would provide simultaneous and continuous analysis of multiple analytes. No sample preparation by the user would be required, and no secondary label needed to establish identification. In short, the process would lead to a truly reliable piezoimmunosensor with significant advantages over current biosensor technology.

Sample antigens are used to compare our Fv-SAM-PZ sensor and existing immunoassay devices (ELISA and traditional monoclonal piezoimmunosensors) for selectivity, sensitivity, linearity, stability, and longevity. Detection limits, appropriate positive and negative controls, and interference will also be addressed. Our objectives are to (1) validate our proposed methods to bind Fvs to the surface of the QCM to form a self-assembled monolayer (SAM); (2) evaluate and validate the Fv-SAM-PZ sensor for rigidity, sensitivity, selectivity, linearity, and dynamic range; and (3) refine the sensor to increase stability, heighten sensitivity, and reduce cross-reactivity. This example focuses on testing current methods in piezoimmunosensor technology. The objective is to define the problems with current piezoimmunosensors and develop a sensor which is compared with current piezoimmunosensors.

A QCM piezoimmunosensor was used to quantitatively determine the kinetics of binding of antibody with carbohydrate. The anti-α-galactosyl antibody was immobilized on Au 10 MHz AT cut crystal and its binding with α-galacosyl epitopes was elucidated with the QCM. A —COOH terminal thiol was used to immobilize the anti-α-galactosyl antibody. This immobilization method generates a film with non-homogenous binding of antibody molecules, which produced variation of available binding sites even though the same amount of antibody is immobilized. This variability in available binding sites was attributed to the fact that the orientation of immobilized antibody is impossible to control. In addition, aggregates of antibody may also form. These preliminary studies indicated that the best way to develop a piezoimmunosensor is through the developments of Fv-SAMs.

Validation of a method to bind Fvs to the surface of the QCM to form a self-assembled monolayer (SAM): The physics of biofilms in liquid is a complex interaction, making it difficult to obtain the relationship between the added mass and the change in frequency detected. Use of the QCM as a biosensor for the study of antigen-antibody binding has raised questions regarding the validity of Sauerbrey's relationship. Several papers have shown that the deposited mass is generally overestimated (Babacan S, Pivarnik P, Letcher S, Rand A G. Biosensors & Bioelectronics. 2000; 15:615-621 and Bizet K, Gabrielli C, Perrot H, Therasse J, Biosenors & Bioelectronics. 1998; 13:259-269). Another limitation of QCM biosensors arises from the large size of immunoglobulins. Consequently, low densities of antibodies are immobilized on the sensor surface. Although multiple immobilization methods have been used with piezoelectric biosensors, there is still no ideal method to give high immobilization yield and good stability.

Using self-assembling monolayers of Fvs on the QCM surface has the potential to solve the drawbacks of current piezoimmunosensors. A highly organized Fv-SAM will have high avidity for the antigen and little surface area for non-specific adsorption. Current molecular techniques allow design of Fvs with appropriate conjugates to form the SAMs. The critical parameters are loading the Fv-SAM on the QCM and the binding affinity of the Fv-SAM. These criteria determine the sensitivity and the selectivity of the biosensor. The following are strategies used to design and immobilize a Fv-SAM sensing layer on the Au support.

Figure 13:
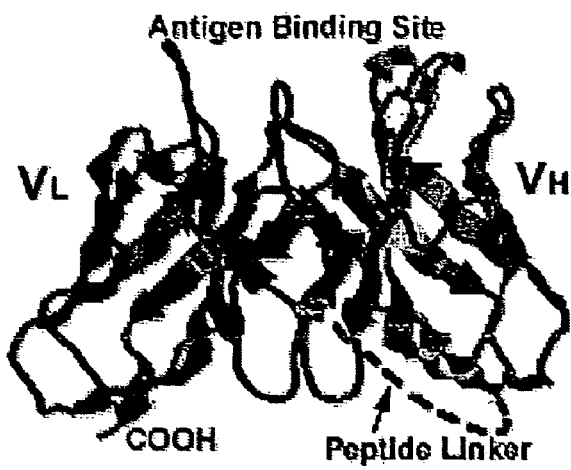
FIG. 13 shows a three-dimensional view of a single-chain Fv protein. The $V_H$ (red) and $V_L$ (blue) domains are shown as well as the antigen binding site (complementarity determining regions or "CDRs"). Also included are the Peptide linker from the carboxyl terminal of the $V_H$ to the amino terminal of $V_L$ and the $V_L$ carboxyl terminal, which will be used to attach the Fv to the Au surface.

Model system to test the stability and binding of several Fv-SAMs: A α-human/goat IgG Fv-SAM is designed. Reverse transcription polymerase chain reaction (RT-PCR) is used to clone the $V_H$ and $V_L$ regions (Orlandi R, Gussow D H, Jones P T, Winter G., Proc Natl Acad Sci USA. 1989; 86:3833-7) of an antibody specific for human or goat IgG (ATCC hybridoma HP6000). Total RNA from the hybridoma is prepared as a template for cDNA synthesis and cloning of the immunoglobulin variable region gene regions. At the 5' end of the $V_H$ a bacterial export signal is provided to direct the protein to the periplasmic space for proper folding and disulfide formation within the bacteria (Skerra A, Pluckthun A., Science. 1988; 240:1038-41). A flexible peptide bridging sequence GP(GGGGS) in the $V_H$-linker-$V_L$ orientation is provided to create a single-chain Fv (Tang Y, Jiang N, Parakh C, Hilvert D., J. Biol. Chem. 1996; 271: 15682-6) (FIG. 13). The constructed scFv gene is inserted into two different commercially available bacterial expression systems for testing.

Expression Systems: Two expression systems are used to express the Fvs to be bound to the Au surface of the QCM. The STREP-TAGII Protein Expression/Purification System utilizes the tightly controlled tet-promoter/operator system to express cloned proteins as fusions with the Strep-tag (Skerra A, Schmidt T G., Biomol Eng. 1999; 16:79-86). The vector leads to the protein's expression in the periplasm of *E. coli* by means of the ompA signal sequence. Periplasmic expression leads to proper folding of the Fvs in *E. coli*. The Strep-tag is a small 8 amino acid streptavidin binding sequence. The short Strep-tag II should not interfere with the folding of the recombinant Fv. Strep-tagged recombinant proteins can be easily purified from crude cell extracts to near homogeneity with a single pass through the StrepTactin column in a mild physiological buffer. A second system, the PINPOINT Xa Protein Purification System, is designed for the production and purification of fusion proteins that are biotinylated in vivo. Biotinylated fusion proteins are produced in E. coli and are affinity-purified using the SOFT-LINK Soft Release Avidin Resin under mild conditions.

Figures 14A, 14B, 14C, 14D, 14E:
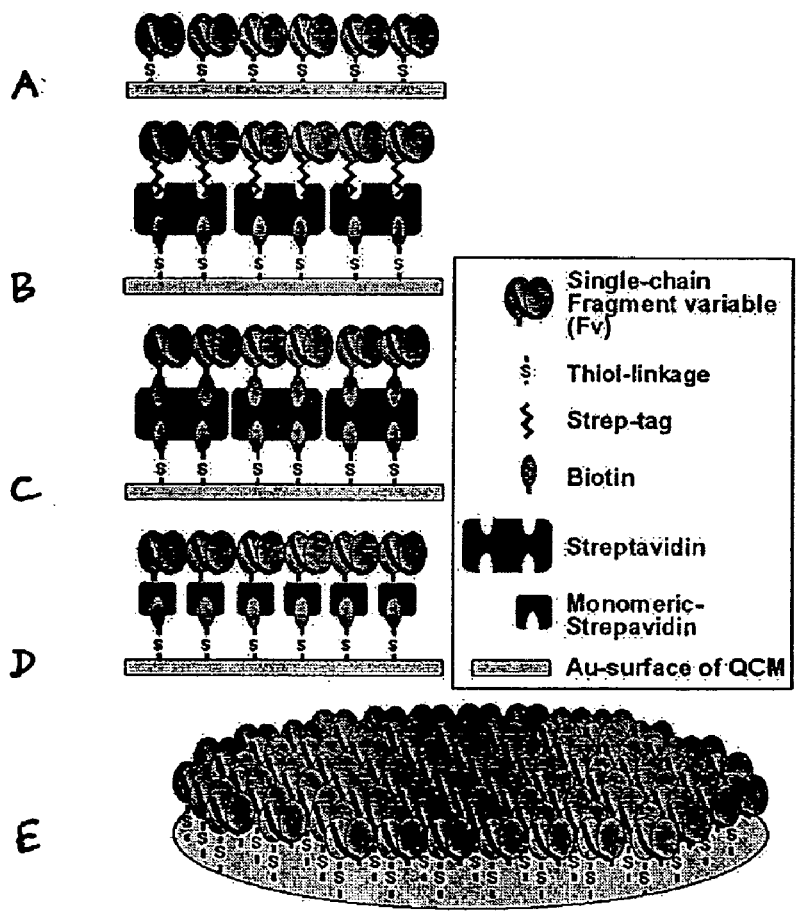
FIG. 14A shows a strategy for creating Self-Assembling Monolayers on the QCM.
FIG. 14B shows a strategy for creating Self-Assembling Monolayers on the QCM.
FIG. 14C shows a strategy for creating Self-Assembling Monolayers on the QCM.
FIG. 14D shows a strategy for creating Self-Assembling Monolayers on the QCM.
FIG. 14E shows a strategy for creating Self-Assembling Monolayers on the QCM.

Strategies for Self-assembled-Fv on Au: The simplest and most straightforward method of creating a SAM with the recombinant Fvs is to create an Fv with a terminal cysteine (Dawson S L, Tirrell D A., J Molecular Recognition. 1997; 10:18-25 and Kneller L R, Edwards A M, Nordgren C E, Blasie J K, Berk N F, Krueger S, Maikrzak C F., Biophysical Journal 2001; 80:2248-2261) for covalent conjugation to the Au surface (FIG. 14A). This should theoretically create a highly ordered, correctly oriented SAM on the QCM (FIG. 14E). This is the preferred method for the microbalance due to the very thin and rigid nature of this monolayer. This approach can be achieved with either vector due to Factor Xa endoproteinase cleavage sites. This allows exposure of a terminal cysteine we will incorporate into the construct for direct conjugation of the Fv onto the Au surface. Should problems due to disulfide formation between Fvs in the periplasm be encountered, large pinholes in the monolayer, or no SAM formed with this method, three alternate systems to develop a SAM are available (FIGS. 14B-D). These other systems are tested, regardless of initial results with the terminal cysteine studies, for comparison of SAM formation and linearity of the Sauerbrey equation.

FIG. 14B demonstrates leaving the Strep-tag on the Fv to provide a specific substrate with which to bind the Fv to streptavidin on the surface of the QCM. A potential problem with this method is that leaving on the Strep-tag requires eluting the Fv with biotin by competitive displacement on the StrepTactin column. Any contaminating biotin would react with the streptavidin we are using as a substrate to form our SAM on the QCM. An alternative purification method would be to use a Goat IgG affinity column to purify the Fvs.

A distinct advantage to the PINPOINT system is the addition of biotin to the Fv. By purifying the Fvs with an antigen-specific (i.e., goat IgG) column, the biotin can be maintained. The biotinylated recombinant Fv provides a specific substrate with which to bind the Fv with high affinity to streptavidin on the surface of the QCM (FIG. 14C).

Monomeric streptavidin Fv: Streptavidin is a protein made up of 4 identical subunits, approximately 15 kDa each, produced by the bacterium *Streptomyces avidinii*. The streptavidin/biotin system has one of the largest free energies of association observed for noncovalent binding of a protein and small ligand (Biotin is 24 kDa) in aqueous solution ($Ka=10^{14}$) (Jung L S, Nelson K E, Stayton P S, Campbell C T., Langmuir. 2000; 16:9421-9432 and Green N M. Avidin. Adv Protein Chem. 1975; 29:85-133). One monomer of streptavidin forms a beta barrel with extended hairpin loops. Biotin is bound at the open barrel side and a surface loop folds over the biotin. This complex is stable over a wide range of temperatures and pH.

Most studies aimed at developing monomeric streptavidin have focused on reducing the association constant to develop a reversible binding reagent (Mohammad Hassan Qureshi, et al., J. Biol. Chem. 2001; 276: 46422-46428 and Sano T, et al., Proc. Natl. Acad. Sci. USA 1997; 94: 6153-6158). Previous work on fusion of streptavidin to single-chain Fvs had the goal of creating multivalent or multispecific antibody fragments (Dubel S, et al., J Immunol Methods. 1995; 178:201-9 and Kipriyanov S M, et al., Hum Antibodies Hybridomas. 1995; 6:93-101). The wealth of information available on the crystal structure (Weber P C, et al., Science 1989; 243:85-88 and Weber P C, et al., J Am Chem Soc 1992b; 114:3197-3200) and interactions between the subunits will allow for rational site-directed mutagenesis of the protein. These studies proceed if there are difficulties developing a SAM with a terminal cysteine residue on the Fv. The development of a monomeric streptavidin focuses on mutating the hydrophobic amino acids at the points of contact between the subunits. This should prevent association and increase the solubility of the subunit. This monomeric streptavidin is then be expressed as a fusion protein with the single chain Fv (FIG. 14D).

Figure 15:
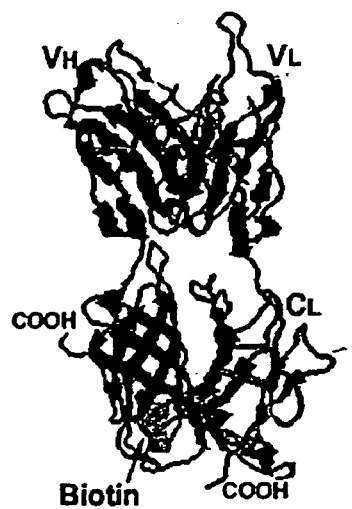
FIG. 15 shows a cartoon of the Streptavidin-FAB fragment. This hypothetical molecule would contain the entire Light chain ($V_L$ and $C_L$) and the variable region of the Heavy chain ($V_H$) expressed as a fusion protein with streptavidin. A cysteine residue could be added to the carboxyl terminal of the $C_L$ and the alpha helical loop of streptavidin to create a covalent bond between the proteins for greater stability, similar to the natural disulfide bond between the light and heavy chains of an immunoglobulin. The area of close contact between $C_L$ and streptavidin are both hydrophobic and should further stabilize the molecule.

The fact that a subunit of streptavidin is similar in size and shape to an immunoglobulin domain has potential advantages (FIG. 15). This allows creation of a fragment antigen binding (FAB) with the $C_H$ domain replaced by a monomer of streptavidin. The $C_L$ domain can stabilize the streptavidin through hydrophobic interactions between the two proteins. By incorporating a cysteine into the side of the streptavidin that normally interacts to form a dimer, it should be possible to create a disulfide-bond with the constant domain of the heavy chain. The hydrophobic side groups and the disulfide-bond should create a stable FAB fragment that could be affinity purified on an antigen column and form an irreversible biotin interaction on the surface of the QCM.

Biotinulation of the gold surface: A distinct advantage of using a biotinylated gold surface to build our SAM is that this system has been well characterized (Spinke J, et al., J Chem phys. 1993; 99:7012-7019; Nelson K E, et al., Langmuir. 2001; 17:2807-2816; Mittler-Neher S, et al., Biosensors & Bioelectronics. 1995; 10:903-916 and Haussling L, et al., Angew Chem Int Ed. 1991; 30:569-572). Biotinylated alkylthiolate can be either purchased commercially. This compound can also be synthesized with varying chain lengths of biotinylated alkylthiolate (Booth C., et al., Tetrahedron. 2001; 57:9859-9866 and Spinke J, et al., J chem Phys. 1993; 99:7012-7019). It is dissolved in ethanol and the Au QCM electrode is incubated in 1 mM biotinylated alkylthiolate for 24 hours to form a self-assembled monolayer. It is then washed thoroughly in the appropriate solvent and dried in $N_2$. The biotinylated SAM is characterized using the techniques described previously before exposing it to streptavidin solution. Should steric hindrance prevent an ordered SAM formation in the systems shown in FIG. 14A-E, a spacer such as $HS(CH_2)_{11}OH$ can be added (Booth C., et al., Tetrahedron. 2001; 57:9859-9866 and Spinke J, et al., J chem Phys. 1993; 99:7012-7019).

Site-directed mutagenesis and chimeric proteins: PCR based site-directed mutagenesis is primarily used in these studies (Higuchi R, et al., Nucleic Acids Res. 1988; 16:7351-67). Gene-specific oligonucleotide primers with one or more mismatches containing the desired mutation are used. Many variations on this protocol exist for tailoring the procedure to various needs. PCR-based methods offer the advantages of speed and convenience for simple substitutions. pfu DNA polymerase will be used for its 3'→5' proofreading activity to prevent secondary mutations. All mutations are confirmed by DNA sequencing.

Evaluation of antigen binding to QCM bound Fv fragments is as follows: (1) ELISA: Binding affinity of the Fvs are evaluated relative to standard ELISA techniques using the parent monoclonal antibody. The HP6000 hybridomas are grown in serum free media and affinity purified on a protein G column. The monoclonals are then used in a standard sandwich ELISA. Briefly, 1-10 µg/mL of the α-human/goat IgG monoclonals are diluted in coating solution (10 mM PBS, pH 7.2) to immobilize the antibody to the microplate. The plate is blocked with a BSA solution followed by addition of the varying dilutions of goat antibody (antigen) to be tested. A secondary α-goat horseradish peroxidase conjugated antibody and ABTS is used for detection of antigen binding. This allows for comparison of the sensitivity of the Fv-SAM-Pz Biosensor relative to a standard immunological assay.

Traditional monocolonal piezoimmonosensors: The system herein is ideal for comparison to a traditional monoclonal piezoimmunosensor because of the wealth of data available in literature focusing on the immunological reaction of anti-goat/human antibody with IgG (Suleiman A A, et al., A review. Analyst. 1994; 119:2279-82 and Su X, et al., Anal Biochem. 1999; 273:62-72). For example, the first PZ quartz SAW sensor was developed to detect human IgG in solution by Roederer et al. (Roederer J E, et al., Anal Chem. 1883; 55:2333-2336). The ST-cut crystal was modified with glycidoxypropyltrinethoxy saline. An antibody, goat anti-human IgG, was immobilized on the crystal and tested for the detection of IgG. The detection limit is 13 μg and linear range is 0.0225-2.25 mg/mL. Muramatsu et al. developed another IgG piezoimmunosensor by immobilizing protein A onto the surface of crystal modified with (γ-aminopropyl)-triethoxy-silane (Muramatsu H, et al., Anal Chem. 1987; 59:2760-2763). The linear range is $10^{-6}$-$10^{-2}$ mg/mL. In the above system, even though the correlation between the observed frequency shifts and the concentration of human IgG were found in the linear range, the frequency shift is greater than the values deduced from the Sauerbrey equation. It is valuable to test the correlation obtained with the Fv-SAM-PZ.

Evaluate and validate the Fv-SAM-PZ Sensors for rigidity, sensitivity, selectivity, linearity, and dynamic range: Even though piezoimmonosensors have been proposed for over 20 years (Suleiman A., et al., Analyst. 1994; 119:2279-2282), there is no well established immobilization procedure which provides a sensing layer that is chemically stable during the measurement process, contains high numbers of binding sites, and forms a thin uniform surface. As shown previously, four bioengineering methods will be used to create a Fv that can form a SAM possessing the necessary attributes. Successful development of a Fv-SAM-PZ may lead to a highly accurate and inexpensive alternative to other labeled and non-labeled immunoassays currently available. Extensive studies are carried out to (1) grow a stable Fv-SAM (2) characterize each step of Fv-SAM formation; (3) study the properties of Fv-SAMs as a biorecognition agent for the piezoimmunosensor.

An α-goat Fv with a cysteine tail (Fv-SH) on the Au electrode is used as the model system to illustrate the experimental protocol below. The protocol can be applied to the other three strategies described previously (FIG. 14A-E).

Growth of rigid α-goat Fv-SAM films on Au surface: The surface roughness may affect the order of SAM and consequently affect the order and rigidity of immobilized Fv. Two Au surfaces (polished and non-polished) of 10 MHz AT cut quartz crystal are used (International Crystal Manufacturing Company, Inc., Oklahoma City, Okla.). Use of the unpolished surface allows measurements on how surface roughness affects the quality of immobilization of Fv-SAM. The piezoelectric active area is 0.22 cm$^2$.

The Au quartz crystal is cleaned with hot Piranha solution (30% $H_2O_2$:$H_2SO_4$, 1:3) and dried with nitrogen. The frequency is measured. Fv-SH is dissolved in appropriate buffer (0.05M phosphate buffer pH=7.0). The freshly cleaned crystal is dipped in the Fv-SH solution for 24 h at room temperature. It is then washed with solvent and deionized water to remove any loosely adsorbed Fv-SH. This immobilizing procedure is the most important step. For a stable, robust sensor, the Fv-SH should be immobilized in high concentration and proper orientation to obtain the highest possible capture capacity for the antigen. The quality of the immobilization affects the sensitivity and specificity of the measurement because the surface coverage affects the sensitivity of mass sensing device. Moreover, nonspecific adsorption can be minimized by complete surface coverage. Consequently, the concentration, temperature and immobilization time on the quality of the film is studied to determine the optimum combinations for the highest yield of Fv-SAM.

Characterization of the Fv-SAM layers: Electrochemistry, network impedance analysis, and Atomic Force Microscope (AFM) is used in parallel to characterize the immobilized Fv-SAM layers for defects/pin hole structure, rigidity, orientation, stability, and surface coverage. The concentration of Fv-SH, time of immobilization, type of solvent, and temperature is varied to understand the conditions that lead to formation of an ordered, rigid, and complete SAM-Fv film. This information is used to guide experimental design to optimize Fv engineering and the immobilization methods to design the best system for the ultimate piezoimmunosensor.

Figure 16:
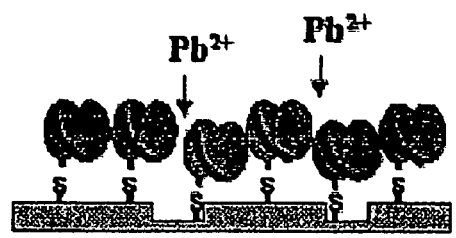
FIG. 16 shows a UPD probe for Fv-SAM porosity and defects.

Electrochemistry methods: A hyphenated electrochemistry method is used to study the growth mechanism and defects and/or porosity of Fv-SAM. As shown in FIG. 16, this involves interpreting the changes in $Pb^{2+}$ underpotential deposition (UPD)features on a Fv-SAM modified Au electrode. UPD is usually the first stage of metal deposition on a foreign metal substrate. One of the important findings on both single and polycrystalline surfaces is that UPD is very sensitive to the surface structure of the substrate crystal. Using cyclic voltammetry (CV) to follow UPD deposition and stripping of lead from single crystal gold, Hamelin et al. (Hamelin A., J Electroanal Chem. 1982; 142: 299-316; Hamelin A, Lipkowski J. J Electroanal Chem. 1984; 171: 317-330; Hamelin A. J Electroanal Chem. 1984; 165:167-180; Hamelin A., J Electroanal Chem. 1979; 101:285-290 and Hamelin A., Edt. Plenum Press, New York 1985; 16:1-40) and Adzic et al. (Adzic R, Yeager E, Cahan D D., J Electrochem Soc. 1974; 121:474-480) showed that the number of UPD peaks, peak potentials, peak heights, and peak widths were characteristic of the substrate surface's crystallographic orientation. Therefore, the surface "signature" of Pb UPD processes could be used to study chemisorptions of organic/bio molecules at both single crystal and polycrystalline electrodes by characterization of the UPD adatoms that form from dissolved metal ions that penetrate the SAM layer (Oyamatsu D, Kuwabata S, Yoneyama H., J. Electroanal. Chem. 1999; 473:59-67 and Whelan C M, Smyth M R, Barnes C J; J. Electroanal. Chem. 1998; 441:109-129). As shown by Porter et al. (Porter M D, Bright T B, Allara D L, Chidsey C E., J Am Chem Soc. 1987; 109: 3559-3568), an ideal, densely packed, crystalline-like, defect-free SAM provides substantial barriers to electron transfer and is strongly resistant to ion penetration. By using Pb UPD probe we can identify the primary substrate metal surface sites participating in concurrent adsorption process from changes in the UPD isotherm. This isotherm information will provide the basis for elucidating the interaction of organic/bio molecules with Au surface; in particular, the molecular orientation and surface coverage of the Fv-SAM adsorbate will be correlated with the modified surface's electrochemical reactivity. The blocking properties of Fv-SAM will indicate a perfect, defect free layer. A major attraction of the UPD probe technique is the availability of different, unique UPD metals that can be selected to study a specific system.

Figures 17A, 17B, 17C:
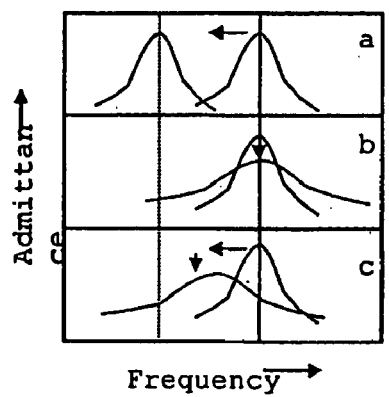
FIG. 17A shows a schematic representation of crystal impedance response for purely gravimetric changes.
FIG. 17B shows a schematic representation of crystal impedance response for purely viscoelastic.
FIG. 17C shows a schematic representation of crystal impedance response for simultaneous gravimetric and viscoelastic changes.

Network Impedance Analysis: As discussed previously, some piezoimmunosensor researchers report a linear relationship between frequency shift and the amount of mass loaded on the sensor. Other researchers report that frequency shift is affected by mass load, viscosity, and density of the media and shows no association with the classic microgravimetry signal. It is important that our engineered SAM-Fv film is a thin (adheres well to the surface) rigid film, for then the measured frequency shift is proportional to the mass of the film. The added mass moves synchronously with the shear motion of the surface. QCM acoustic impedance analysis (Agilent 4395A network impedance analyzer) can be used to validate the use of the Sauerbrey equation by characterization of any changes in energy loss upon the binding of antigen to antibody. It determines the electroacoustic impedance (or admittance) spectrum over a specified frequency range in the vicinity of crystal resonance. By comparing the shape of the spectrum of the perturbed resonator to an unperturbed device, one can explore the validity of the Sauerbrey equation (Schmitt N., Tessier L., Watier H., Patat F., Sensors and Actuators B. 1997; 43:217-223). As shown in FIG. 17A (Hillman A., Mobile species populations and viscoelastic effect in electroactive polymer films, solid state ionics, 1997; 94:151-160), a translation toward lower frequency with no change in the shape of the spectrum is characteristic of a rigidly coupled mass layer. Damping of the crystal oscillation is characteristic of a fluid or viscoelastic material (FIG. 17B). Simultaneous gravimetric and viscoelastic changes result in both peak position and shape changes (FIG. 17C). The electroacoustic admittance measurement around the resonance frequency will be used for Fv-SAM interface modeling that will guide us to achieve the ultimate goal of a thin rigid Fv-SAM layer.

Figure 18:
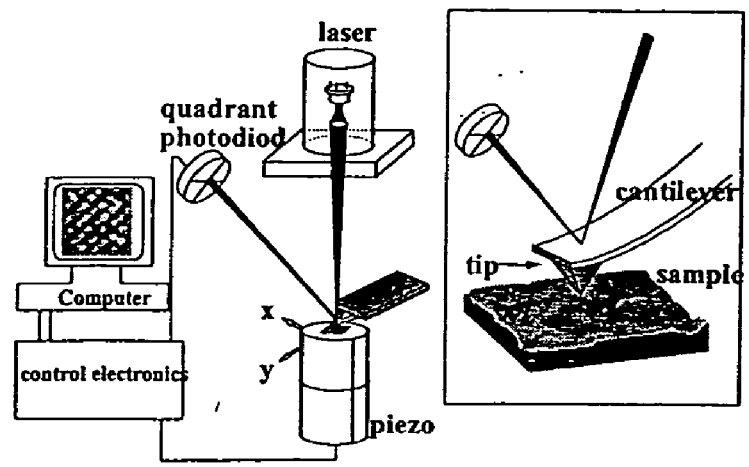
FIG. 18 shows a schematic diagram of a typical AFM, with an optical beam deflection configuration. As shown more clearly in the frame, a tip (1-2 mm) is in contact with the surface. A laser beam is focused on the back of the cantilever, and detected by a four-segment photodiode detector. The cantilever bends up and down, and twists left and right during a scan along the X-axis. Detection of these deflections enables simultaneous measurement of surface topography and frictional force.
Figure 19:
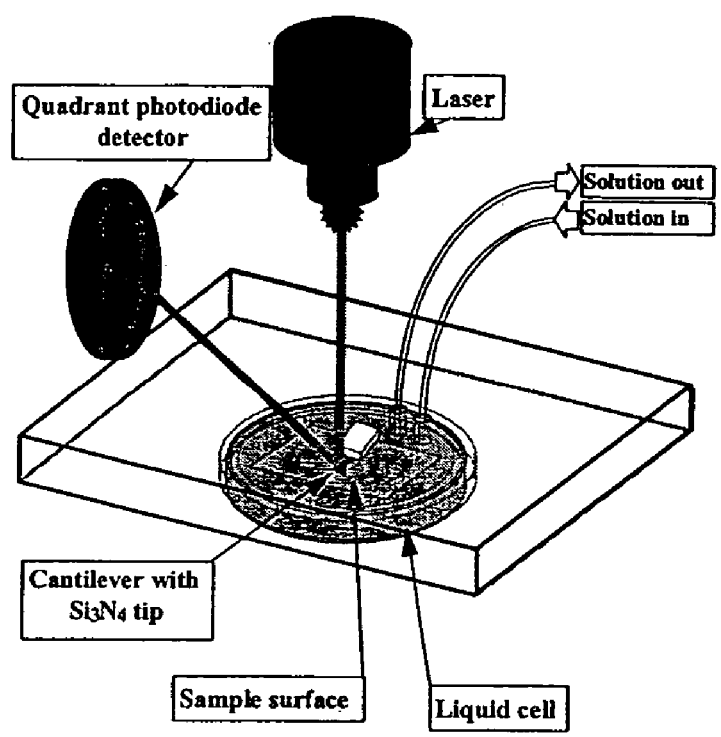
FIG. 19 shows a schematic diagram of the experimental set-up used for in situ AFM imaging of monolayer formation in liquid solutions. The cell contains up to 1.0 mL of a liquid that can be injected or removed from the cell with minimal perturbation to the system.

Atomic Force Microscope (AFM): AFM studies provide a molecular level understanding of specific antigen/antibody interactions. FIG. 18 is the schematic diagram of AFM instrumentation. It can be operated under physiological conditions and enable high-resolution microscopic images to be acquired in situ (Browning-kelley M E, Wadu-Mesthrige K, Hari V, Liu G Y. Langmuir. 1997; 13:343-350). A liquid cell (FIG. 19) that allows injection of solutions with minimal disturbance during in situ imaging is used. By imaging in liquid, the capillary force between the tip and sample is eliminated; therefore, the total imaging force can be reduced to as low as 0.1 nN. With such a low imaging force, the spatial resolution can be significantly improved due to lowered sample deformation. The liquid also serves as solvent and buffer (Bard A J, Abruna H D, Chidsey C E D, Faulkner L R, Feldberg S W, Itaya K, Majda M, Melroy O, Murray R W, Porter M D, Soriaga M P, White H S, J Phys Chem. 1993; 97: 7147-7173). During experiments, the surface is imaged continuously during growth. Therefore, the structural evolution is monitored in situ and in real time. This provides information on growth mechanisms and kinetics. Approximately every two or five minutes, we zoom to desired areas and examine the surface structure with high resolution to investigate whether and when a crystalline structure forms. Thus, AFM imaging will allow direct observation of the structure of each phase, and quantitative information about film kinetics may be observed. Surface coverage will be determined as a function of time using image analysis software in conjunction with AFM data acquisition and analysis software. Taking advantage of the high resolution in the z direction, the height thresholds of Fv-SAM and the lying-down or standing-up phases can be visualized from the corresponding cursor plots and histograms of height distribution. The coverage of these phases can then be calculated from the peak areas in the histograms by counting pixels within images. We estimate that coverage can be determined with uncertainties in the range 5 to 15%, depending on the quality of the AFM images. The uncertainty in coverage determination is a consequence of mainly two factors: first, the uncertainty in determining the boundaries of the adsorbed domains due to convolution of the finite size of the AFM tip; second, the imperfections of the gold substrate (steps, defects) which complicates the height distribution histogram and introduces an uncertainty in thresholds. A flat, polished Au surface will be used in AFM study.

Characterization of Fv-SAM piezoimmunosensor: The requirements of various sensors are based to a large extent on their respective applications, but the common stipulations are (1) sensitivity in the range of interest; (2) selectivity for the analyte; (3) broad dynamic range; (4) reversibility; (5) robustness and reliability; (6) lack of frequent calibration; (7) fast response; (8) inertness to sample matrix; (9) unattended operation, robot-compatibility, user friendliness; (10) small size; and (11) low cost (Wolfbeis Otto S., Fresenius J Anal Chem. 1990; 337:522-527). In particular, we emphasize (1) studying the effect of the immobilized Fv-SAM on the frequency of the piezoelectric quartz crystal; (2) comparing the experimental data with the results predicted by Sauerbrey's equation; (3) testing the sensitivity and selectivity of immobilized $\alpha$-human/goat antibodies with goat IgG; and (4) obtaining the kinetic and thermodynamic data for $\alpha$-human/goat antibodies with an IgG immunoassay.

The sensitivity, response time, reproducibility and detection limit of $\alpha$-goat/human Fv-SAM piezoimmunosensor: Sensitivity, fast response time, reproducibility, and low detection limits are basic requirement for any sensor. The detection limit is the smallest amount of analyte that can be determined with confidence. Sensitivity is the change in signal per unit change in the amount of analyte and is equivalent to the proportionality constant in a standard calibration curve. The immobilized Fv-SAM is incubated in phosphate buffer (pH=7). The standard calibration curve is obtained by incubating various concentrations of goat IgG with different $\alpha$-goat/human Fv-SAM coated crystal for 1 hour. The goat IgG standard can be obtained commercially. The IgG standard solution is made in phosphate buffer. The change of frequency of coated crystal before and after incubation with IgG is measured and monitored in situ over time during the injection. This provides information for the sensor response time to analyte. The detection limit and linear range is obtained by studying the linearity of the calibration curve when different standard solutions are used. The reproducibility is studied by using at least 5 duplicates for the whole antigen (IgG) range. The sensor response is also studied for its linearity according Sauerbrey equation by comparing the theoretical (Sauerbrey equation) and experimental frequency decrease due to mass loading by immobilization of a known amount of Fv-SAM.

Figure 20:
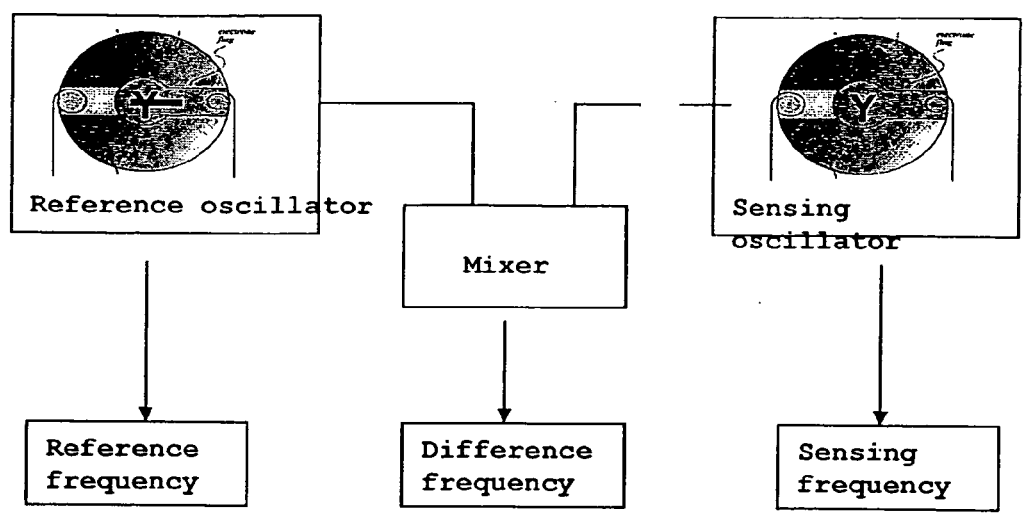
FIG. 20 shows a block diagram of DQCM oscillator circuit.

Current QCM sensors detect mass changes in liquid or gas phase by monitoring the frequency of the immersed crystal directly or with respect to an external reference crystal. It is important to note that as the temperature of the bathing fluid changes during the course of an experiment, the bathing fluid's viscosity and density also change resulting in the shift of the immersed crystal frequency. Consequently, a Dual Quartz Crystal Microbalance (DQCM) technique is used (FIG. 20). This technique has previously been used in electrochemistry studies for separating the redox induced frequency changes from medium induced frequency change (Bruckenstein S, Michalski M, Fensor A, Li Z., Anal Chem. 1994; 66:1847-1852). Here, we use the DQCM to extract a signal corresponding only to the Fv-antigen binding. A cell incorporating two quartz crystals will be used; one, the reference sensor, consists of a quartz crystal with a Fv-SAM where the binding site is blocked by a blocking agent, such as oligo(ethylene glycol) group, which is inert to the adsorption of protein (Mrksich M., Chem Soc Rev. 2000;29: 267-273), and the other, the Immunosensor, consists of the Fv-SAM with available binding sites. While adding antigen to the DQCM cell, the frequency difference between the submerged reference and sensing crystals will be monitored. This design will improve the sensitivity and detection limits. In addition, our instrument can also manipulate the interface potential/charge of the sensing crystal. This enables us to regenerate the surface (described below) and study the electrostatic interaction of the antibody immobilization process and antigen-antibody binding processes. The potential control was accompanied using an AFCBP1 bipotentiostat (Pine instrument company) or EG&G 283 potentiostat. The output, either frequency or mass, will be recorded either by an X-Y1-Y2 recorder (Western graphic W3000 recorder) or a PC computer.

Selectivity and reversibility of α-goat/human Fv-SAM piezoimmunosensor: A sensor is selective if its signal is a function of only the amount of analyte present in the sample. Mouse IgG is used to test whether there is cross-reactivity of our Fv-SAM piezoimmunosensor. For individual sensors, reversibility is not critical as a piezoimmunoassay is inexpensive, that is, it is affordable to use disposable transducers. However, it is important to study the reversibility of the binding reaction to assess the feasibility of continuous monitoring without calibration. The bound IgG antigen can be removed with a high salt solution or low pH (65)Carter R M, Mekalanos J J, Jacob M B, Lubrano G J, Guilbault G G. J. Immunological Methods, 1995; 187:121-125). This condition does not harm the immobilized antibodies. This method is not expensive but it can cause significant degradation after several re-uses. Therefore, it is safer practice to remove the whole antigen-Fv complex or use freshly labeled crystals for each assay. In addition, for biohazard detection, once the QCM sensor is exposed to antigen, it is considered to be contaminated and should be disposed of or de-contaminated. De-contamination will likely destroy the immobilized antibody and not allow for re-use. Since the formation of Fv-SAM is based on the chemisorption of the sulfur atom of the thiols onto the gold surface: $Fv-SH+Au \rightarrow Fv-Au+e+H^+$, the Fv-SAM can be removed from the metal surface through a reductive desorption (Fung Y S, Wong Y Y., Anal Chem. 2001; 73:5302-5309). Crystals can be cleaned with proper reagents such as NaOH and then relabeled with Fvs. This procedure can be repeated until the gold substrate is either too thin or becomes uneven, which will produce poor immobilization of the Fv coating.

Robustness and reliability of α-goat/human Fv-SAM piezoimmunosensor: It is important that the α-goat/human Fv-SAM piezoimmunosensor is robust (stable) and reliable (few false positive and false negative detections). We will calibrate the sensor frequently to determine its long term stability and reliability. In this context, "long term" is the time period until which the calibration curve shows deterioration of linearity and sensitivity. Our goal is to develop our sensor to be robust and reliable for long-term use. This is important for such applications as underground monitoring. In flow injection analysis, calibration can be performed at any time or at any defined rate, thus the calibration process could be automated.

Evaluation of sensor performance in real world sample analysis: An evaluation protocol is developed which uses real-world samples (for example, goat serum) and compares the data obtained by Fv-SAM-PZ not only with other immunochemical methods but also with those obtained by conventional methods such as Gas chromatography (GC) or liquid chromatography (LC) and GC/Mass Spectrometry (MS) or LC/MS. Matrix effects are addressed by providing comparative data of standard curves produced in buffer and in the real world matrix. The offset of the curves can then be established for quantitating samples. Controls are used to quantify matrix effects and antibody cross-reactivity. Because of the large sample capacity inherent in immunoassays, it is easy to include extensive controls in the analysis.

Evaluation of the Fv-SAM-PZ by determining the binding constant: Sauerbrey's equation allows for obtaining the association constant ($K_a$), the binding amount at the nanogram level ($\Delta m$), and the binding constant ($k_1$ and $k_{-1}$) by measuring the time relationship of frequency decrease at various antigen concentrations, according to the following equations (Ebara Y, Itakura K, Okahata Y, Langmuir. 1996; 12:5165-5170; Okahata Y, Natsuura K, Ito K, Ebara Y., Langmuir. 1996; 12:1023-1026 and Yang M, Yau Hellas C M, Chan H L., Langmuir. 1998; 14:6121-6129):

$$[antigen]+[Fv]_{k-1} \rightleftarrows^{k1} [antigen\text{-}Fv\ complex] \quad (1)$$

$$[antigen]_0/\Delta m = [antigen]_0/\Delta m_{max} + 1/(\Delta m_{max} K_a) \quad (2)$$

$[antigen]_0/\Delta m$ vs. $[antigen]_0$, which, according to equation (2), yields a straight line. The association constant $K_a$ and maximum binding amount $\Delta m_{max}$ can be calculated from the slope and intercept.

Binding kinetics can be calculated from the equations 3-5 below. The time relationships of antigen-Fv complex formed at time t after injection are (Ebara Y, Itakura K, Okahata Y, Langmuir. 1996; 12:5165-5170; Okahata Y, Natsuura K, Ito K, Ebara Y., Langmuir. 1996; 12:1023-1026 and Yang M, Yau Hellas C M, Chan H L., Langmuir. 1998; 14:6121-6129):

$$[antigen\text{-}Fv\ complex]_t = [antigen\text{-}Fv\ complex]_{infinite}(1-e^{-(1/\tau)t}) \quad (3)$$

$$\Delta m_t = \Delta m_{max}(1-e^{-(1/\tau)t}) \quad (4)$$

$$\tau^{-1} = k_1[antigen]_0 + k_{-1} \quad (5)$$

A plot of reciprocal of relaxation time ($\tau^{-1}$) of binding against various concentrations of antigen gives a linear relationship as shown in equation (5). The slope and intercept give $k_1$ and $k_{-1}$ respectively. The kinetic and thermodynamic data obtained from the Fv-SAM-PZ are compared with literature values.

Figure 21:
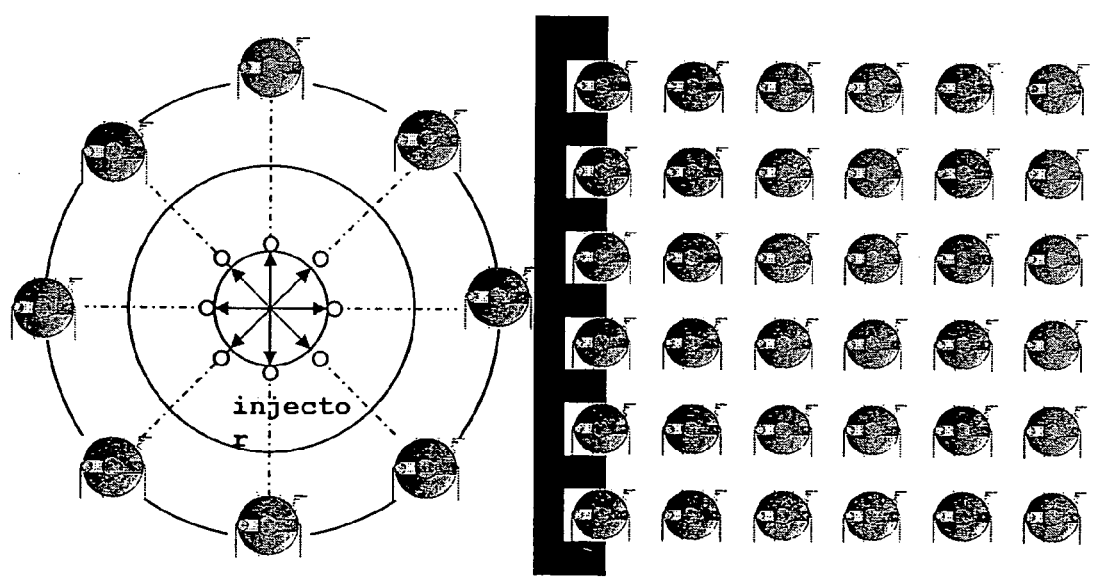
FIG. 21 shows a schematic diagram of Fv-SAM QCM sensor array. Each QCM is sensitive for a different antigen. An electronic circuit will provide the frequency shift of each QCM immunosensor in relation to its reference QCM sensor.

Sensor Arrays for multi-analyte detection: Automation of immunoassay has been a challenge to chemists and engineers. The need to screen analyte panels in blood, urine, water, sewage, etc., has become increasingly frequent in clinical diagnostic, forensic medicine, and environmental monitoring where several analytes need to be determined. Sensor arrays not only permit measurement of multiple analytes in the same small sample but also reduce the analysis time. Fv-SAM-PZ allows highly sensitive detection for small samples. A new automated immunoassay method based on flow injection analysis is developed to detect multi-analyte samples. The flow injection immunoanalysis format consists of multiple QCM sensors. Each QCM sensor has a specific Fv-SAM. Reagents are pumped in a time-controlled manner through a center valve for multi-channel sample injection (FIG. 21). Sophisticated computer software interprets the data and provides immediate detection and identification of antigen. This device could monitor water supplies, pesticide runoff, industrial effluents, and clinical samples.

Refine the sensor to increase stability, heighten sensitivity, and reduce cross-reactivity: Fv fragments are the smallest units of antibodies that retain the specific antigen binding characteristics of the whole molecule. These are non-covalently associated heterodimers of the $V_H$ and the $V_L$ chain domains. Without modification, Fvs tend to dissociate, unfold, and/or nonspecifically aggregate. The fragments we use are stabilized by producing a recombinant single-chain protein in which the two chains are linked by a short polypeptide linker (Bird R E, Hardman K D, Jacobson J W, Johnson S, Kaufman B M, Lee S M, Lee T, Pope S H, Riordan G S, Whitlow M., Science. 1988; 242:423-426). However, application of Fvs can be limited due to their unpredictable stability and solubility. Stability can be further improved by replacement of the hydrophobic residues that normally interact with the constant domains of the FAB (Nieba L, Honegger A, Krebber C, Pluckthun A., Protein Eng 1997; 10:435-444). There is a wealth of literature available on methods to increase the stability of the single chain Fvs through modifications of residues (Worn A, Pluckthun A., J. Mol. Biol. 2001; 305:989-1010). An alternative strategy is to substitute an internal disulfide bridge for the peptide linker to connect the two variable chains (Jung S H, Pastan I, Lee B., *Proteins*. 1994; 19:35-47). This method, while having the disadvantage of having to express two separate proteins, produces stable Fv proteins, which may prove helpful in the present invention. Our goal is to create a Fv framework upon which different antigen binding sites may be grafted to produce a highly stable Fv-SAM sensitive to any antigen of interest.

Stability engineering of Fvs: There is a wealth of information available on stability engineering of antibody single-chain Fv fragments (Worn A, Pluckthun A., J Mol Biol 2001; 305:989-1010). Studies have been done using both site-directed and evolutionary approaches to increase the stability, solubility, and half-life of Fvs predominately for use in vivo. The fact that Fvs can survive for days to weeks in the body is promising for their use on the QCM as a biosensor. However, formation of a SAM offers unique challenges for Fv engineering. Rather than solubility being of utmost concern, stability of the SAM in a dirty environment is critical. If generating a Fv with the characteristics needed for SAM formation we reduce the solubility of the protein, a gentle solvent can be added (such as DMSO) to the SAM formation process to keep the Fvs in solution until they bind the QCM.

Figure 22:
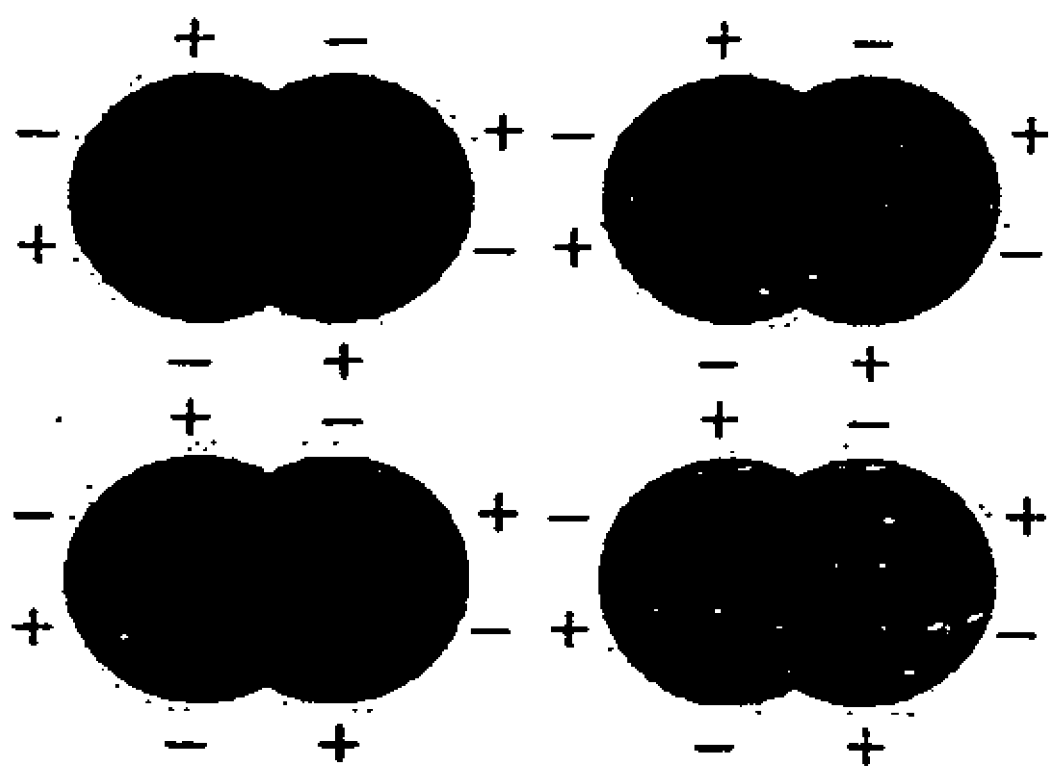
FIG. 22 shows a top view of Fvs with introduced charged side residues that will lead to salt-bridges between highly ordered Fvs on the QCM surface.

More critical than solubility for SAM formation is the ability to form a tightly packed monolayer on the QCM surface. This may be facilitated through rational manipulation of side residues on the Fv. The abundance of crystallography data on Fvs allows for prediction of residues due to the conserved nature of the Fv scaffolding. Creating positive, negative or hydrophobic patches on the sides of the Fvs would allow the Fv to form salt-bridges or hydrophobic interactions at the contact points (FIG. 22). Manipulation of side residues to form a tightly packed SAM should increase the stability of the Fvs on the QCM surface leaving only the antigen binding sites available for interaction with the solute. This tight packing of the Fvs should reduce the effects of protease's on the Fvs and lend to the overall stability of the Fv-SAM. The packing rules can be applied to any antigen-specific Fv for creation of a Fv-SAM-PZ.

Cross-reactivity: Immunological recognition is based on the spatial complementarities of groups in the epitope of the antigen with those in the paratope of the antibody. In the case of macromolecules, each antibody recognizes a specific epitope that generally constitutes a fraction of the total structure. In favorable cases, antibodies can be used to recognize a single substance in the presence of several thousand similar species. The problem with substance-specific immunological assays is that antibodies target epitopes, not the whole antigen. Multiple substances may have the same or similar epitopes. When this is true, antibodies fail to discriminate by "cross-reacting" with structurally similar species (Emon Van J M, Lopez-Avila V., Anal Chem. 1992; 64:79A-88A and Walters R R. Affinity Chromatography. Anal Chem. 1985; 57:1102A-1114A). In an effort to overcome false positives, a second level of immunological discrimination is often used. To address cross-reactivity, two Fvs are developed for each antigen to be detected. Each Fv binds to a different epitope of the same antigen. The individual Fvs are attached to separate QCMs within the sensor. Positive detection requires simultaneous binding on both of the QCMs.

Single Antigen binding domains for detection of antigen: An alternative for developing a SAM with specific antigen binding properties is to use a single $V_H$ domain for binding. Minimization of the antigen-binding fragment to such a small single-domain protein offers the advantage of enhanced stability (Nuttall S D, Irving R A, Hudson P J., Curr Pharm Biotechnol. 2000; 1:253-63). In one embodiment only the VH domain is used in the biosensor. The disadvantage of this system is that new fragments would have to be cloned for each antigen to be detected. However, this single-domain strategy can provide a more uniform lawn of binding sites that creates a better SAM and has fewer sites available for non-specific interactions.

Biofouling: Biofouling of any biological sensor is inevitable due to accretion of contaminants over time. This is addressed by developing improved buffers for the Fv-SAM-PZ. While initial studies use a standard phosphate buffer for detection of antigen, once Fv-SAM formation is established we test the stability of the monolayer in multiple buffers. This includes spiking various buffers with solvents and protease inhibitors to monitor the stability over time. The QCM allows us to continually monitor the monolayer for degradation in each test solution and test at incremental time points for sensitivity to antigen.

An advantage of our system is that the "lawn" of Fvs covering the QCM surface is uniform and densely packed, leaving less opportunity for non-specific interactions or molecule trapping. Therefore, there should be less accretion of contaminants than in current piezoimmunosensors. Nevertheless, the QCM sensor arrays will have to be replaced over time. Replacement costs will be significantly less than for other biosensor systems due to the relatively low cost of both the transducer component (the QCM) and the biological component (recombinant antibody fragments).

Creation of useful Fv for detection of biological agents: Fv-SAMs can be used for detection of a toxin (e.g., botulism toxin tainted food), a virus (e.g., HIV contaminated blood), a bacterium (e.g., *E. coli*), and a protozoan (e.g., *Cryptosporidium parvum* contaminated water). Fv-SAM piezoimmunosensor are a viable solution to the need for a highly accurate, easy to use biosensor for mass production. The basic principle of Fv-SAM-PZ is elegant and simple. Once immobilization of Fv by SAM is completed, duplication is straightforward and mass production of biosensors is feasible. A SAM is formed by the spontaneous association of molecules under equilibrium conditions that yields a stable, structurally well-defined two-dimensional aggregate. Consequently, SAMs are inherently manufacturable. The high affinity of Fv makes it a very versatile analytical reagent capable of reacting specifically with analytes at a very low concentration in a complex solution such as serum. Additionally, Fv for a wide range of substances can be obtained easily through currently available molecular techniques such as phage display. The small sizes of Fvs allow them to be engineered with a variety of linkers making formation of a SAM layer relatively easy. The piezoelectric transducer is a mass sensor that only requires oscillator circuits. Oscillator circuits are relatively simple and inexpensive to fabricate, which make our sensor suitable for field instruments. Digital frequency counters to measure the oscillator signal are equally suitable for fabrication as lightweight components of field instruments. The frequency measurements are also beneficial because frequency is one of the most precisely measurable quantities with precision of about $1:10^{10}$. The devices can be easily automated or combined with flow injection systems extending their capability for continuous and repeated assays. This raises an exciting possibility of using crystal arrays to assay different analytes in complex samples with on-line display of the results.

The Fv-SAM piezoimmunosensors disclosed herein will open up new avenues in ultra-sensitive analysis of trace substances in complex biological systems. We are convinced a whole spectrum of piezoimmunosensors will be developed using our approach. Our system can be used for bioterrorism defense, environmental pollutant monitoring, forensic analysis, biological research, and routine clinical tests in laboratory medicine. With parallel developments in microbiology for better biorecognition reagents, a wide spectrum of piezobiosensors for gas, liquid, and solid detection could be produced. Despite current thinking to the contrary, the advantages implicit in combining the highly sensitive microbalance with highly selective immunochemical reactions can be realized by rational manipulation of recombinant antibody fragments.

EXAMPLE 3

The A10B hybridoma cell line, producing a monoclonal antibody (MAb) specific for rabbit IgG was used to provide an ScFv antibody for the piezoimmunosensor of the present invention. The hybridoma cell line designated A10B was used as the source of genetic information for production of scFv. This cell line produces a monoclonal IgG antibody that binds specifically to the constant region (CH1) of rabbit IgG. A10B scFv thus generated contained antibody variable heavy and light chains joined together by either a GGGGSGGGGSGGGGS (A10B scFv) or CGGGSGGGGSGGGGS (A10B scFv-cys) or SHG-GHGGGGSGGGGS (A10B scFv-his) linker sequences. Female Balb/c mice immunized with purified rabbit IgG were used as a source of B spleen cells to produce the A10B hybridoma cell line. The QUICKPREP mRNA purification kit (AmershamFrom Biosciences, Piscataway, N.J.) was used to purify mRNA from approximately $5\times10^6$ A10B hybridoma cells. The RPAS kit (AmershamFrom Biosciences, Piscataway, N.J.) was used to produce A10B ScFv according to the manufacturer's instructions, with the following modifications. The (GGGGS)$_3$ linker peptide sequence used in the RPAS kit was changed to CHG-GHGGGGSGGGGS (SEQ ID NO:21). This modification was used to increase ScFv avidity through the formation of cysteine-linked A10B ScFv dimers and to enable the ScFv to bind metals (e.g. copper) via the GGH (diglycylhistidine) sequence. The cysteine in the A10B ScFv linker sequence also enables the A10B ScFv to bind to gold. A10B ScFv displaying the modified linker sequence retained antigen-binding activity.

From the A10B hybridoma a bacterial clone which produces a single-chain Fv (ScFv) was made. The bacterial clone designated A10B RS, produces the A10B ScFv recombinant antibody which binds to rabbit IgG. This clone contains a linker coding for the amino acid sequence GGGGSGGGGSGGGGS (SEQ ID NO: 18). The A10B ScFv protein has the amino acids of the A10B antibody variable heavy chain joined to amino acids of the A10B antibody variable light chain by a linker. The linker having the amino acid sequence GGGGSGGGGSGGGGS (SEQ ID NO: 18) is known in the art of ScFv recombinant antibodies. The ScFv has the structure: A10B (variable heavy)-GGGGSGGGGSGGGGS-A10B (variable light). The single chain antibody can consist of one variable heavy antibody chain (VH) linked to one variable light chain antibody (VL) as a VH-linker-VL construct, or a VH-linker-VH construct or a VL-linker-VL construct. The constructs can have tags or amino acids located either on the amino or carboxy terminus of the construct. The tags can be engineered to contain amino acids that can be useful to attach single chain antibody to supports, metals (e.g. gold) or reporter molecules (e.g. biotin, dyes, enzymes, etc.). Single chain antibodies (ScFv) can be modified to display one or more cysteines or histidines located within the single chain antibodies in locations that do not interfere with ScFv binding activity or located within the linker sequence connecting the VH-VL or within tags on the amino or carboxy terminus of the ScFv. When loading the ScFv onto the gold surface of the QCM, the ScFv must all be properly oriented and covalently bound to the surface. To optimize this process a transient positive charge on the bottom of the ScFv is used. By lowering the pH to 6 the introduced histidines will be positively charged and attracted to the negatively charge gold surface when electrodes are applied. The construct can be any fragment or portion of a single chain antibody modified to display one or more cysteines or histidines located within the single chain antibodies in locations that do not interfere with ScFv binding activity or located within the linkers or located within tags on the amino or carboxy terminus of the ScFv. The cysteines and/or histidines allow for binding to the metal of the quartz crystal microbalance.

The bacterial clones designated A10B C-3 (ATCC No. PTA-6045 deposited Jun. 4, 2004) and A10B C-4 each produce an A10B ScFv recombinant antibody which binds rabbit IgG. Clones A10B C-3 and A10B C-4 are identical and have the linker amino acid sequence SHG-GHGGGGSGGGGS (SEQ ID NO:19) to take advantage of the fact that the amino acid sequence GGH can bind to metals, so as to enable the ScFv to be bound to the gold quartz crystal microbalance (QCM). The A10B RS can be modified by methods known in the art to have a cysteine in the linker, for example an amino acid sequence of CGGGSGGGGSGGGGS (SEQ ID NO:20) which enables the A10B ScFv to be bound to a gold quartz crystal microbalance (QCM) by thiol coupling. The A10B scFv used in FIGS. 23-30; FIGS. 32-37 are A10B scFv with the SHGGHGGGGSGGGGS (SEQ ID NO:19) linker. The A10B scFv used in FIGS. 38, 40-47 are A10B scFv with the CGGGSGGGGSGGGGS (SEQ ID NO:20) linker. The A10B ScFv was cloned into bacteria using the pCANTAB5E DNA vector (RPAS kit, Amersham Biosciences, Piscataway, N.J.), however any vector suitable for ScFv cloning can be used. U.S. Pat. No. 5,864,019 to King et al., U.S. Pat. No. 6,630,584 B1 to Solomon et al., U.S. Patent Application Publication Nos. US 2003/0100060 A1 to Fulton et al. and US2003/0022244 A1 to Solomon et al., hereby incorporated herein by reference in the their entirety, describe single chain variable fragment antibody (scFv) construction. In further embodiments of the present invention, the ScFv is cloned to have the linker amino acid sequences of CGGGSGGGGSGGGGS (SEQ ID NO:20), CHGGHGGGGSGGGGS (SEQ ID NO:21), or other sequences having one or more cysteine residues to facilitate thiol coupling to the QCM surface.

The A10B anti-rabbit IgG scFv is a functional single-chain Fv with a cysteine tail able to bind, correctly oriented, on the Au surface of the QCM. The A10B-scFv binds to the constant region ($C_HI$) of rabbit IgG. The A10B is a mouse anti-rabbit IgG that binds in the FAB portion of rabbit IgG. The small size of the target antibodies, 150 kD, allows us to use this relatively small molecule as a model antigen to test the sensitivity of the recombinant antibody-based piezoimmunosensors. Our ability to detect such a small molecule in a dirty solution suggests that when we go on to test much larger antigens, such as viruses or bacteria, the signal will be even stronger. By producing recAb fragments which contain only the antigen binding portion of the antibody (the Fv domains), the area available for nonspecific interactions is significantly reduced. Recombinant DNA technology further allows for incorporation of residues for covalent binding to the Au surface of the QCM.

Immobilization of a thin rigid film of scFvs on the QCM and optimal orientation of the antigen-binding region is of paramount importance in preventing non-specific interactions and trapping of molecules. The simplest and most straightforward method of creating a monolayer with recombinant scFvs is through a cysteine incorporated onto the bottom of the scFv. The sulfur of the cysteine can form a thiol linkage between the antibody fragment and the Au surface. We have used an incorporated cysteine residue on the A10B-scFv to attach the scFv to the gold surface of the QCM.

The Au quartz crystal was cleaned with concentrated nitric and sulfuric acid mixture, biograde water, and ethanol in series for three times to remove impurities, and dried with nitrogen. The frequency was measured both dry and in phosphate buffered saline, pH=7.2 (PBS) (Gibco BLR, cat # 20012-027). One side of the gold quartz crystal was incubated with the A10B scFv at 4° C. After incubation, the surface of immobilized Au electrode was rinsed with PBS buffer and biograded water and dried with nitrogen. Next, a blocking reagent such as 0.1% Bovine Serum Albumin (BSA) (catalog # A-9418 Sigma, St. Louis, Mo.) in PBS was applied to the scFv modified electrode for 30 min. to absorb onto any of the Au surface not bound with scFv. After blocking, the electrode was further rinsed with PBS buffer and biograded water to remove any unbound BSA.

The immobilizing procedure is the most important step. For a stable, robust sensor, the scFv should be immobilized at a high concentration and with proper orientation to obtain the highest possible capture capacity for the antigen. Subsequently, the concentration of scFv, the immobilization time, type of blocking reagents, and gold surface roughness on the quality of the film were studied to determine the optimum combinations for the best scFv-SAM.

The Au surface was immobilized in 0.3 mg/mL and 1 mg/mL A10B scFv separately. Our results showed that three times higher concentrations of scFv did not significantly increase the surface density of recAb. Consequently, 0.3 mg/mL was selected for our immobilization concentration.

While keeping all other immobilization conditions fixed, i.e., 0.3 mg/mL scFv, 0.1% BSA blocking reagent, non-polished Au QCM, the effect of different immobilization times (6-hour, 12-hour, 18-hour, 24-hour and 48-hour) on scFv sensor was examined (Table 1). The decrease of frequency for 6-hour and 48-hour immobilization times was much smaller than for other immobilization times. The differences in decrease of frequency and relaxation time between 12-hour, 18-hour, and 24-hour immobilization times were small. Therefore, we chose 18-20 hours as the optimal immobilization time.

TABLE 1

Immobilization time (data correspond to the addition of 20 μL of 0.167 mg/ml rabbit IgG to A10B-scFv immobilized Au surface in 1 mL PBS buffer).

|  | 6-hour | 12-hour | 18-hour | 24-hour | 48-hour |
| --- | --- | --- | --- | --- | --- |
| Δf, Hz | 28-32 | 36-40 | 38-40 | 38-40 | 26-30 |
| τ, Sec | 1200 | 1150 | 1200 | 1110 | 900 |

Blocking reagent: Two different concentrations of BSA were tested for optimal blocking, 0.1% and 5%. The 0.1% BSA solution gave a higher and faster signal response than 5% BSA solution. Methoxy Poly (ethylene Glycol) thiol (PEG) from NEKTAR Transforming Therapeutics (catalogue # 2M4DOH11, M. W. 5000) was also tested as a blocking reagent. The PEG-blocked surface gave a similar response signal as 0.1% BSA; however, as shown in table 2, the relaxation time was almost 3 times longer than the 0.1% BSA. Therefore, 0.1% BSA solution was used as a blocking agent in subsequent experiments.

TABLE 2

Blocking reagent (data corresponds to the addition of 20 μL of 0.167 mg/ml rabbit IgG to A10B-scFv immobilized Au surface in 1 mL PBS buffer).

|  | 0.1% BSA | 5% BSA | PEG |
| --- | --- | --- | --- |
| Δf, Hz | 38-40 | 20-25 | 34-36 |
| Relaxation time (τ), Sec | 1110 | 3800 | 4000 |

Gold surface roughness: The surface roughness of the Au deposited on the QCM can affect the order of the SAM and consequently affect the rigidity of the immobilized A10B scFv. Au surfaces (polished and non-polished) of 10 MHz AT cut quartz crystal were used in this study (International Crystal Manufacturing Company, Inc., Oklahoma City, Okla.). The unpolished Au quartz crystal has 1000 A° Au on quartz wafer. The polished Au quartz crystal has 100 A° Cr under-layer between Au and quartz to increase the adhesion of Au on a smooth surface. The unpolished gold has a rougher surface allowing us to measure how surface roughness affects the quality of immobilized scFv monolayers. The piezoelectric active area is 0.22 $cm^2$.

Our studies show that the scFvs are immobilized with good bioactivity on all the unpolished gold surfaces used in our study. However, when the scFvs are immobilized on the polished Au surface, only one of three experiments gave a positive result. The mechanism of this unexpected result is under investigation. It might be caused by contamination of the Au surface by the Cr under-layer when the electrode is immersed in PBS buffer. As a result of these tests, the unpolished gold has been chosen for subsequent experiments.

Figure 23:
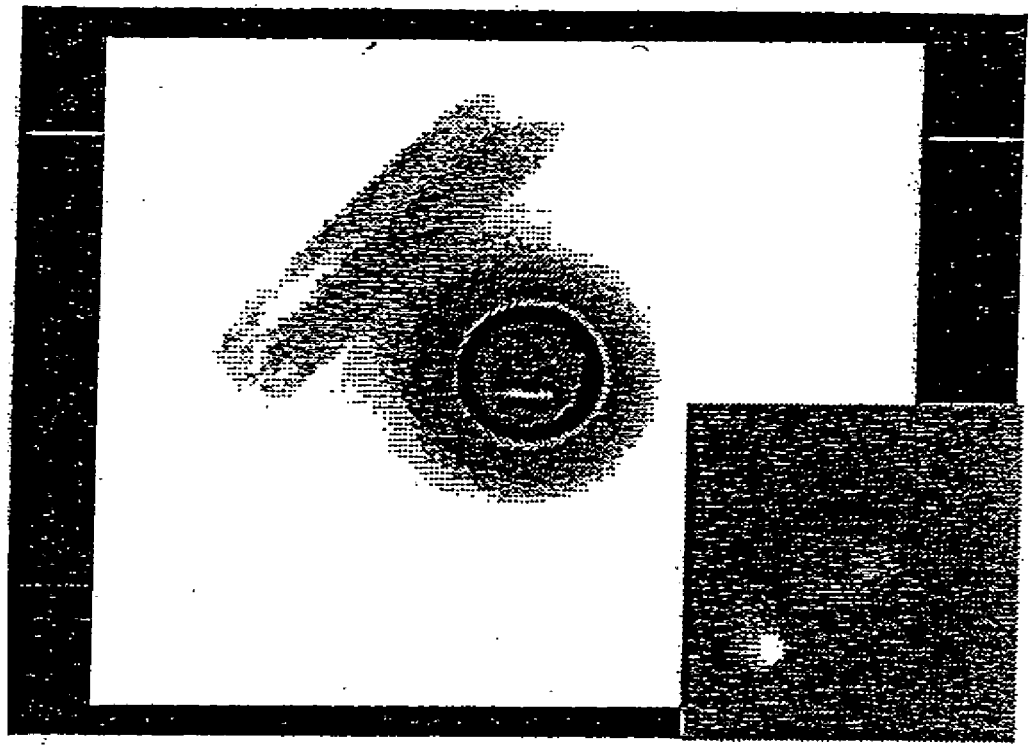
FIG. 23 is a photograph of HRP immunoassay on the A10B-scFv immobilized Au surface ($7.1 \times 10^{-4}$ mg/ml α-E-tag HRP on the scFv immobilized Au surface. After an hour, it was washed with PBS buffer and dried with nitrogen, then ABTS/$H_2O_2$ solution was applied (1.8 microliter of 30% $H_2O_2$. to each ml of ABTS). The green color confirms the successful immobilization of A10B scFv on the Au surface. The insert in right corner is the control experiment done without immobilized A10B-scFv on the Au surface.
Figure 24:
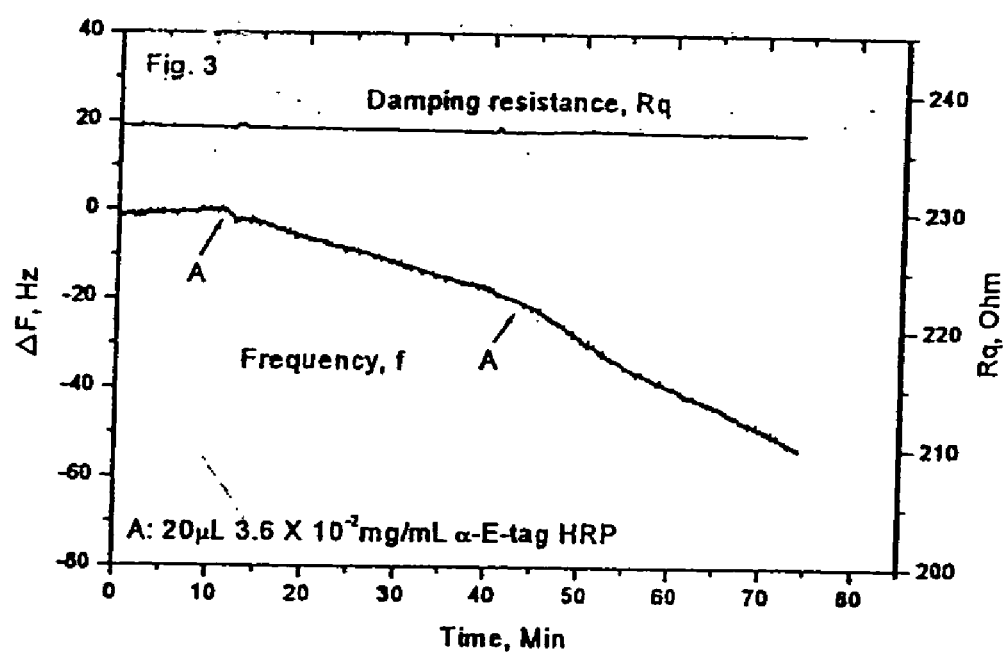
FIG. 24 shows frequency change vs. time curve when 20 µL $3.6 \times 10^{-2}$ mg/ml of α-E-tag HRP in a PBS/Tween buffer was added to the A10B-scFv immobilized Au surface of the QCM in 1 ml PBS-tween buffer.

In summary, the following immobilization conditions were regarded as optimum and were used in further experiments:

Au QCM substrate: unpolished gold surface
ScFv concentration: 0.3 mg/mL
Immobilization time: 18-20 hours
Immobilization temperature: 4° C.
Blocking reagent: 0.1% BSA The A10B-scFv has an E-tag (GAPVPYPDPLEPR; Pharmacia Biotech) incorporated on the amino terminus of the protein. An E-tag is a specific linear epitope recognized by commercially available antibodies. This feature allowed us to directly test the binding of the A10B-scFv on the Au surface by means of a calorimetric assay. If the A10B-scFv is bound to the Au surface, the HRP conjugated α-E-tag antibody will turn green when ABTS and hydrogen peroxide solution are added (FIG. 23). In a second experiment to demonstrate the presence of the scFv on the gold surface, α-E-tag HRP was added to the A10B-scFv immobilized Au QCM electrode. The decrease in frequency, due to binding to the E-tag, upon each addition of α-E-tag HRP is shown in FIG. 24.

Stripping voltammetry: To further test whether the scFv has been covalently bound to the Au via the incorporated cysteine residue, we used electrochemistry stripping voltammetry to characterize scFv immobilization. The binding of the scFv on the Au is based on the chemisorption of the sulfur atom of the cysteine onto the gold surface through a gold thiolate bond as shown here:

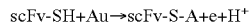

scFv-SH+Au→scFv-S-A+e+H$^+$

Figure 25:
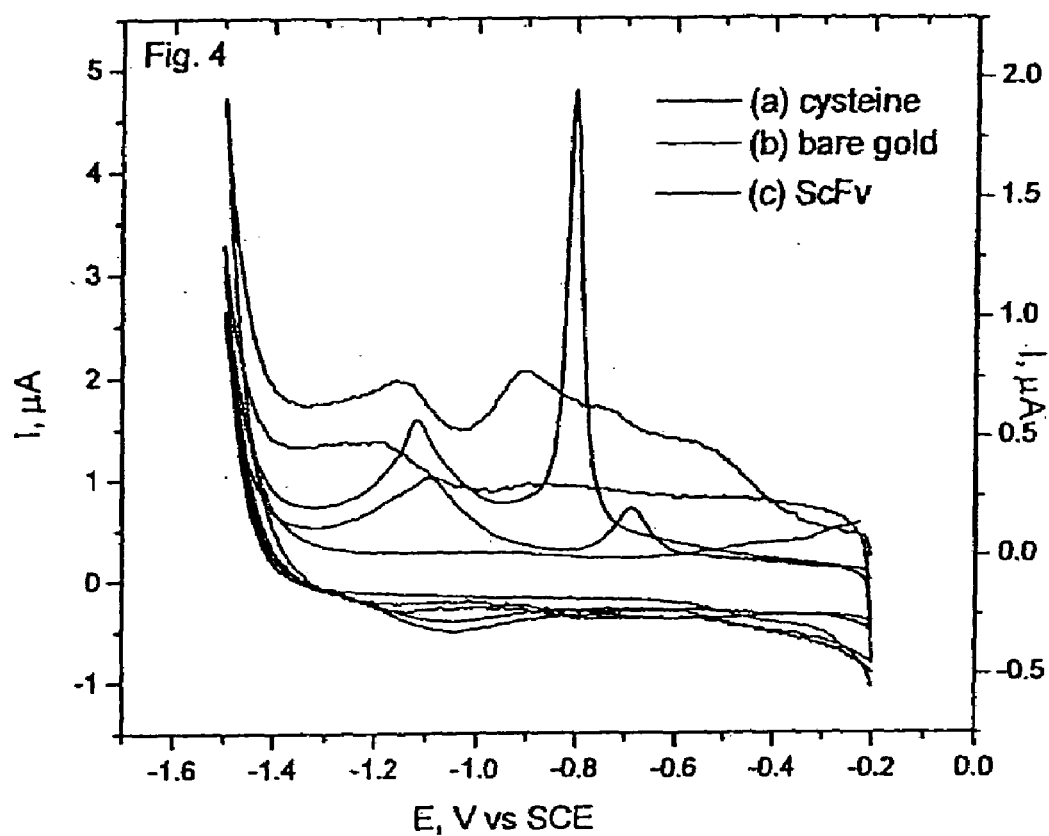
FIG. 25 shows voltammograms obtained in 0.5 mol/L KOH aqueous solution at a scan rate of 100 m V/s. Cyclic voltammetry of (a) cysteine-modified gold electrode; (b) bare gold electrode; (c) scFv-modified gold electrode recorded in a solution of 0.5M KOH. Nitrogen purge for 15 mins to remove the dissolved oxygen.

Thus the organothiol of the scFv monolayer can be removed from the gold surface through reductive desorption if the monolayer has been attached via a cysteine. FIG. 25 shows our data from the stripping voltammetry of bare Au electrode, Au electrode immobilized with cysteine, and Au electrode immobilized with A10B-scFv. A large cathodic peak, observed in the first potential sweep at −0.8~−0.9, and a broad peak at −1.2 V, are shown in the A10B-scFv modified Au electrode. They correlate in shape and position with the characteristic peak of cysteine reductively desorbed under the same conditions. Desorption is almost complete after 6 scans for cysteine modified gold electrode and 3 scahs for scFv modified gold electrode (only two scans are shown in FIG. 25 for clarity of presentation). Surface coverage of the scFv can be calculated by integration of the current peak at −0.9 V. From the Faraday law Q=−nFN (n, number of electrons, F, Faraday constant 96485 Coulombs/mole, and N, number of moles of electroactive species), we obtain a surface coverage of $7.8 \times 10^{-11}$ mol/cm$^2$ with the scFvs. Calculation of the surface coverage of scFvs by quartz crystal microbalance gave a surface coverage $(6.4 \pm 0.4) \times 10^{-11}$ mol/cm$^2$ respectively. The surface coverage obtained by QCM and electrochemical methods were in agreement, this consistency further proving that our biofilms are rigid and Sauerbrey equation is valid for quantitative analysis (see also network impedance analysis).

Previously published studies have reported that a dodecanthiol can obtain a coverage as high as $n \times 10^{-10}$ mol/cm$^2$, ScFvs have a MW of ~27 kD, so $n \times 10^{-11}$ mol/cm$^2$ indicates an excellent surface coverage with the scFv.

We used $K_4Fe(CN)_6/K_3Fe(CN)_6$ to probe the integrity of the scFv-SAM on the gold surface. Since electron transfer between a solution species and the electrode must occur either by tunneling through the monolayer or by approaching the electrode at a "pinhole" or defect in the monolayer, the extent of surface passivation to electron transfer is useful to detect defects in the monolayer. The passivation ability of SAMs of scFv to cyclic voltammetry of contacting aqueous $K_4Fe(CN)_6/K_3Fe(CN)_6$ was studied to further understand the integrity of the scFv-SAM. Shown in FIG. 26A, bare Au surface gave ideal $K_4Fe(CN)_6/K_3Fe(CN)_6$ reversible redox peaks. Faradaic current is dramatically attenuated on the scFv modified surface. Subsequent exposure of these scFv-SAMs to 0.1% BSA blocking reagent resulted in a further increase in passivation, the Faradaic current was completely attenuated, and the only current response to the applied voltage was due to capacitive charging of the electrode. Stripping of the scFv monolayer by reductive desorption renewed the fresh gold surface. These experiments demonstrated that a SAM of scFvs forms an impermeable barrier to electroactive species in aqueous electrolyte and that a primary mode of electrochemical communication between the electrode and the solution electrophore occurs at defect sites rather than by conduction through the monolayer.

Figure 26A:
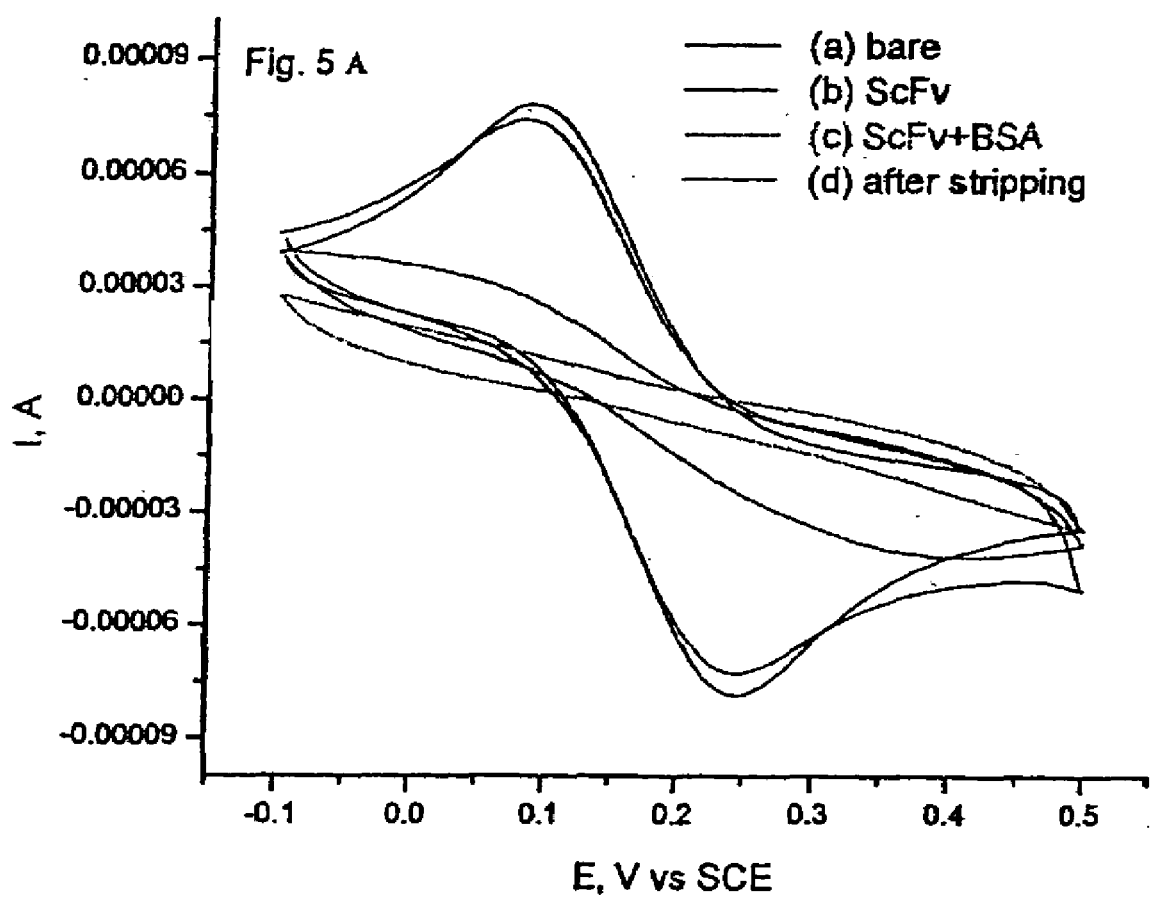
FIG. 26A shows cyclic voltammograms of (a) bare gold electrode; (b) scFv-immobilized gold electrode; (c) ScFv+BSA-immobilized gold electrode; (d) the gold electrode after removal of the scFvs by reductive stripping in a solution of 0.1M sodium perchlorate containing 1 mM $K_4Fe(CN)_6/K_3Fe(CN)_6$.
Figure 26B:
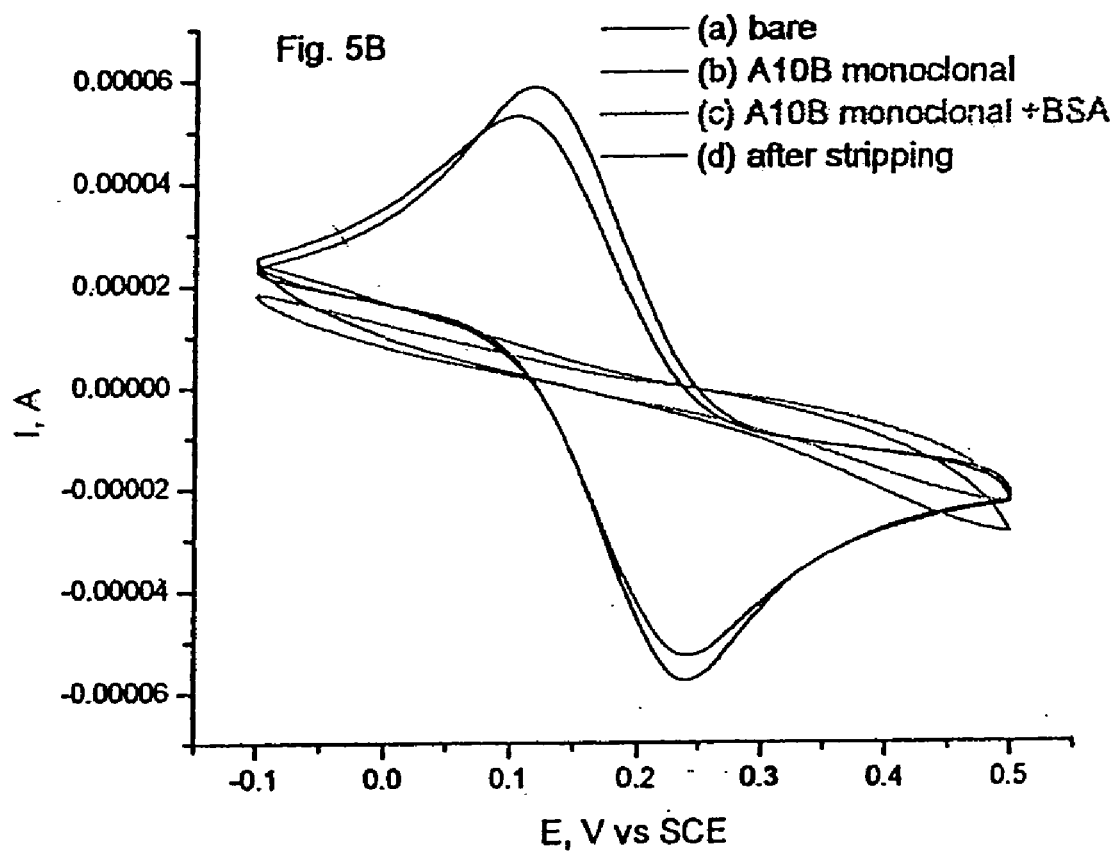
FIG. 26B is the same experimental sequence as FIG. 26A performed on an A10B monoclonal antibody immobilized surface under identical conditions. Cyclic voltammograms of (a) bare gold electrode; (b) A10B monoclonal immobilized gold electrode; (c) A10B monoclonal+BSA-immobilized gold electrode; (d) the gold electrode after removing A10B monocolonal by reductive stripping. Scan rate 100 m V/s.
Figure 27:
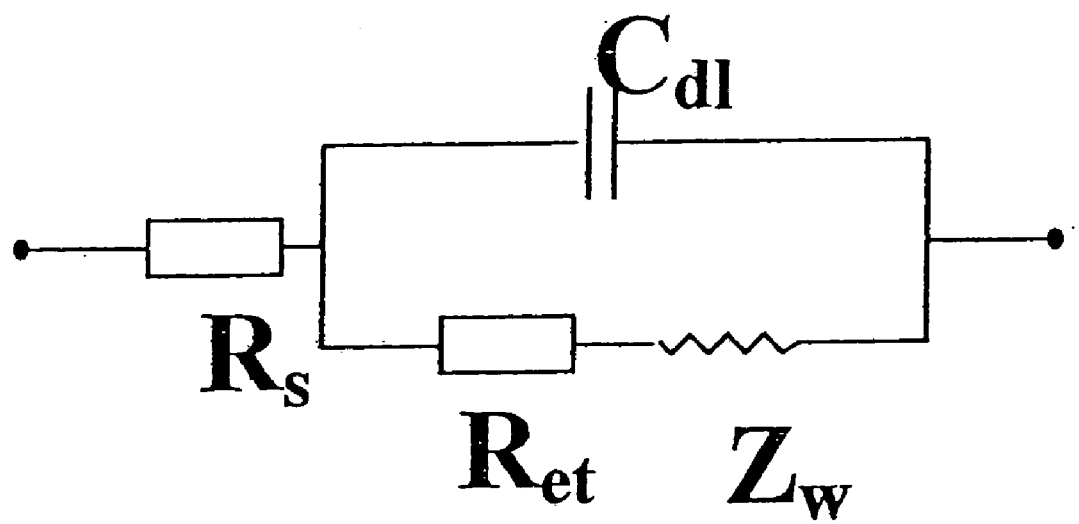
FIG. 27 is an equivalent circuit diagram corresponding to the impedance features of antibody (scFv/or monoclonal) modified electrode interfaces in the presence of redox probe $Fe(CN)_6^{3-/4-}$.

The cyclic voltammograms show similar behaviors between the scFv and the parental monoclonal (FIG. 26B). The difference is that subsequent exposure of these scFv-SAMs to 0.1% BSA blocking reagent did not result in a significant increase in passivation. This indicates that, due to the large size of the monoclonal and its random orientation of immobilization, the surface is almost completely covered. Consequently, the scFv immobilized surface density can be further improved if a much higher scFv immobilization solution is used, suggesting that there is still room for further improvement of the scFv-based piezoimmunosensor. Additionally, this experiment demonstrated that electrochemistry reductive desorption is useful for removal of physically adsorbed proteins (see also electrochemical impedance study below).

Electrochemical Impedance spectroscopy is an effective method for probing the features of surface-modified electrodes[2]. The complex impedance can be presented as the sum of the real, $Z_{re}(\omega)$, and $Z_{im}(\omega)$ components that originate mainly from the resistance and capacitance of the cell, respectively. The general electronic equivalent scheme, Randel circuit, FIG. 27, includes the ohmic resistance of electrolyte solution, $R_S$, the Warburg impedance, $Z_w$, resulting from the diffusion of ions from the bulk electrolyte to the electrode interface, the double layer capacitance, $C_{dl}$, and electron-transfer resistance, $R_{et}$, that exists if a redox probe is present in the electrolyte. The two components of the electronic scheme, $R_s$ and $Z_w$, represent bulk properties of the electrolyte solution and diffusion features of the redox probe in solution, respectively. Therefore, these parameters are not affected by chemical transformations occurring at the electrode interface. The other two components in the scheme, $C_{dl}$ and $R_{et}$, depend on the dielectric and insulating features at the electrode/electrolyte interface. Table 3 lists parallel experiments from FIG. 27 performed by electrochemical impedance spectrometer. As shown by Table 3, $R_{et}$ on the bare gold electrode are very low, less than 0.3 KΩ in all cases. Comparing with the bare Au electrode, the electron transfer resistances increase to 9.7 KΩ and 17.1 KΩ after the electrode surface is modified with scFv and monoclonal A10B, respectively, indicating the successful immobilization of antibody by our strategies. Notice that the Ret of monoclonal A10B modified gold electrode (17.1 KΩ) is much larger than that of scFv modified gold electrode (9.7 KΩ). Blocking with BSA on scFv and monoclonal A10B modified surface further increases the $R_{et}$ to about 17.3 KΩ and 20.0 KΩ, respectively. These data support our rationalization from CV results shown in FIG. 27.

TABLE 3

Comparison of solution resistance $R_s$ and electron transfer resistance Ret for redox probe $Fe(CN)_6^{3-/4-}$ at scFv and monoclonal modified electrode/electrolyte interface by electrochemical impedance spectroscopy.

| A10B ScFv (Ohm) | | | A10B monoclonal (Ohm) | |
|---|---|---|---|---|
| Bared-gold | $R_s$ | 258.4 | 274.9 $R_s$ | Bared-gold |
| | $R_{et}$ | 342.6 | 403.8 $R_{et}$ | |
| ScFv-immobilized | $R_s$ | 243.5 | 306.4 $R_s$ | Monoclonal- |
| | $R_{et}$ | 9718.4 | 17059.2 $R_{et}$ | immobilized |
| ScFv-BSA | $R_s$ | 253.0 | 257.1 $R_s$ | Monoclonal-BSA |
| immobilized | $R_{et}$ | 17280 | 19785.8 $R_{et}$ | immobilized |
| After removing the | $R_s$ | 211.7 | 268.5 $R_s$ | After removing the |
| conjugate by | $R_{et}$ | 305.2 | 490.6 $R_{et}$ | conjugate by |
| electrochemical | | | | electrochemical |
| reductive stripping. | | | | reductive stripping. |

Figure 28A:
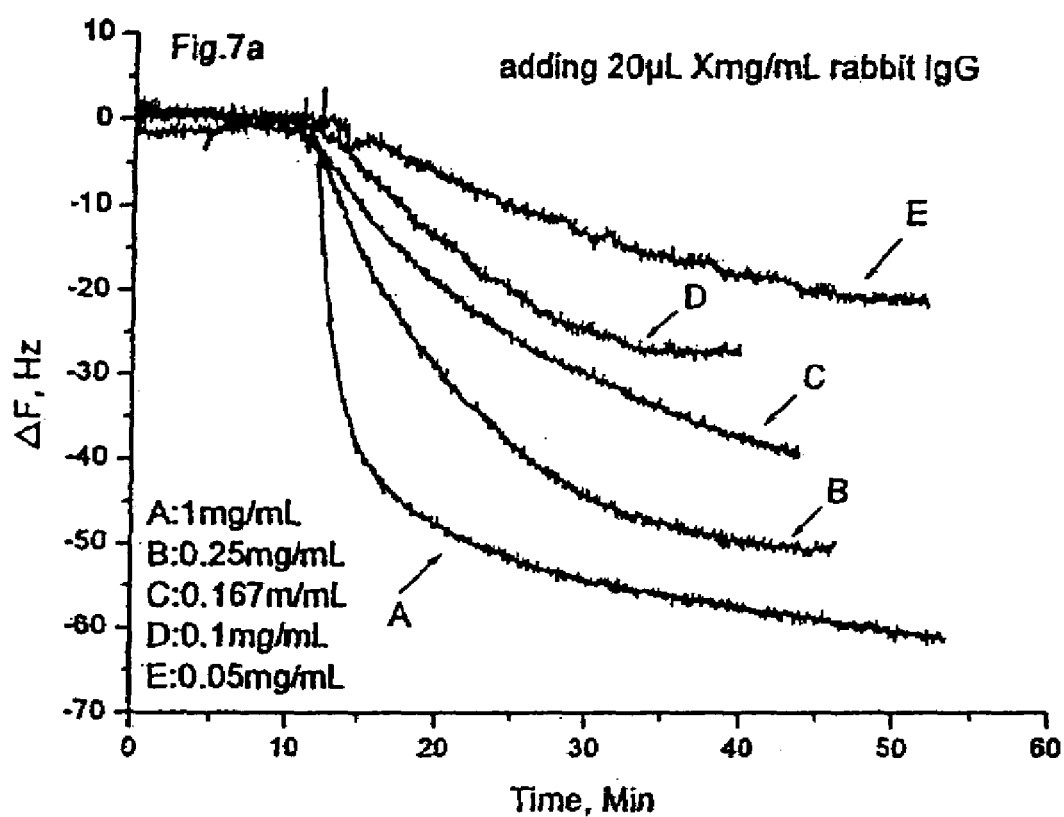
FIG. 28A shows frequency change vs. time.
Figure 28B:
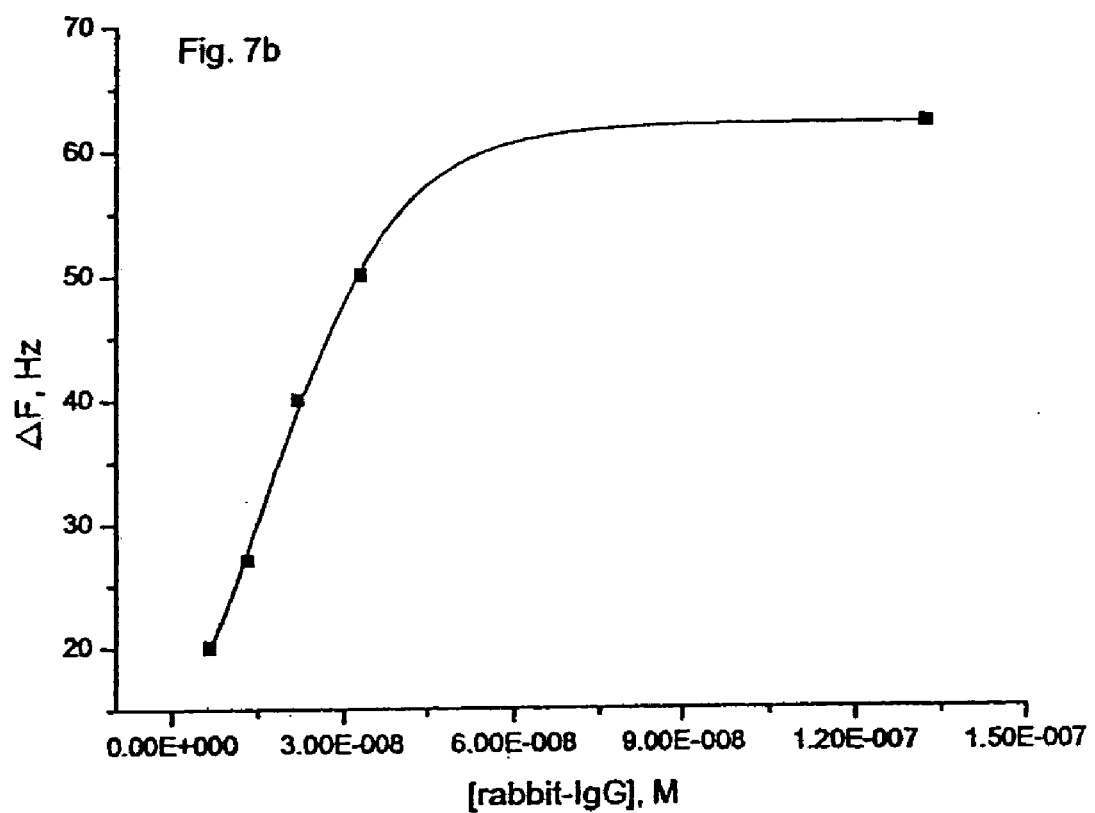
FIG. 28B shows frequency change vs. [rabbit IgG]$_0$ when various concentrations of rabbit IgG were added to the A10B-scFv immobilized Au QCM electrode in 1 ml PBS buffer.
Figure 29:
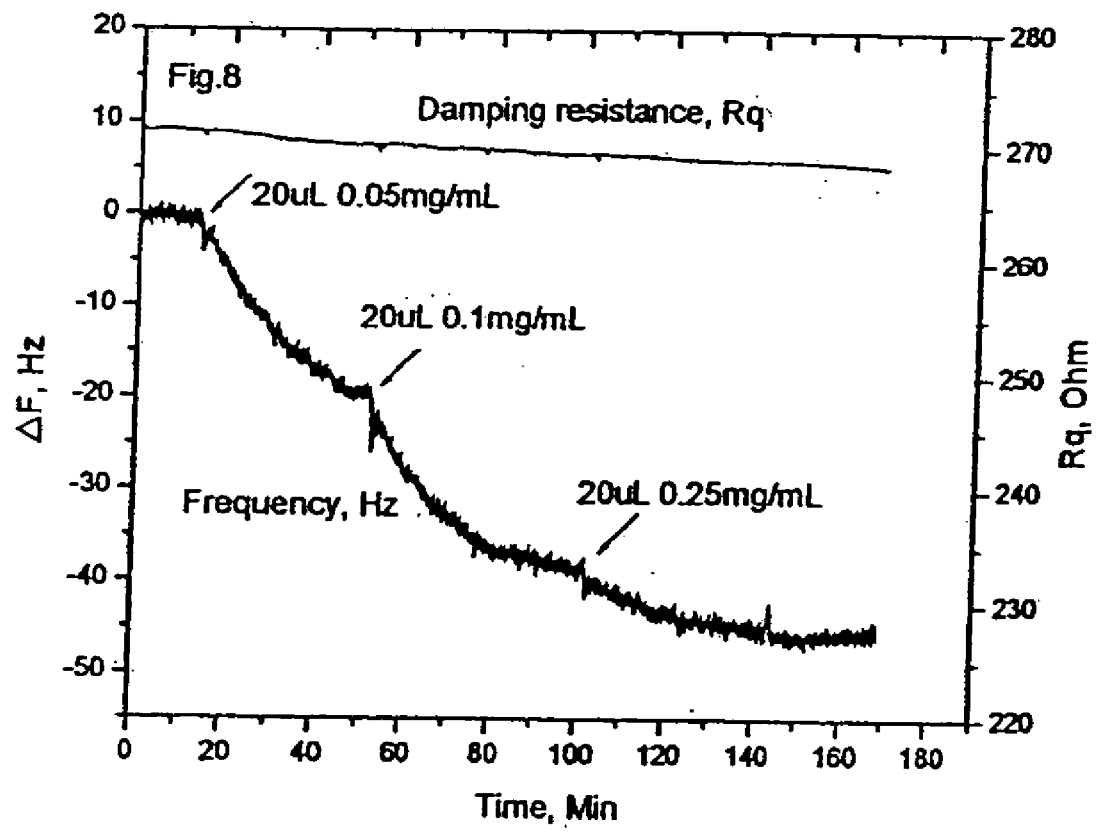
FIG. 29 shows frequency change vs. time curve when successive concentrations of rabbit IgG were added to the A10B-scFv immobilized Au QCM electrode in 1 ml PBS buffer.

Detection of rabbit IgG: The antigen to be detected, rabbit IgG (catalog # I15006 Sigma), was dissolved in PBS buffer. The A10B-scFv was immobilized on five QCM Au electrodes. The frequency change upon adding increasing concentrations (0.05 mg/ml to 1.0 mg/ml) of rabbit IgG vs. time is shown in FIG. 28A. Standard calibration data was obtained from these experiments (FIG. 28B). The detection limit for A10B-scFv binding with rabbit IgG is 0.05 mg/ml, or about $6.6 \times 10^{-9}$ M, and linear range is 0.05 mg/ml-0.25 mg/mL (FIG. 28B). This experiment also shows a fast response time and negligible drift of the baseline. Results were consistent for all 5 scFv-QCM electrodes used in this experiment. FIG. 29 shows the frequency vs. time curve obtained by adding increasing concentrations of 20 uL of rabbit IgG to the immobilized A10B-scFv on the Au QCM electrode. This frequency vs. time curve shows excellent sensitivity of the sensor and fast response time.

Figure 30:
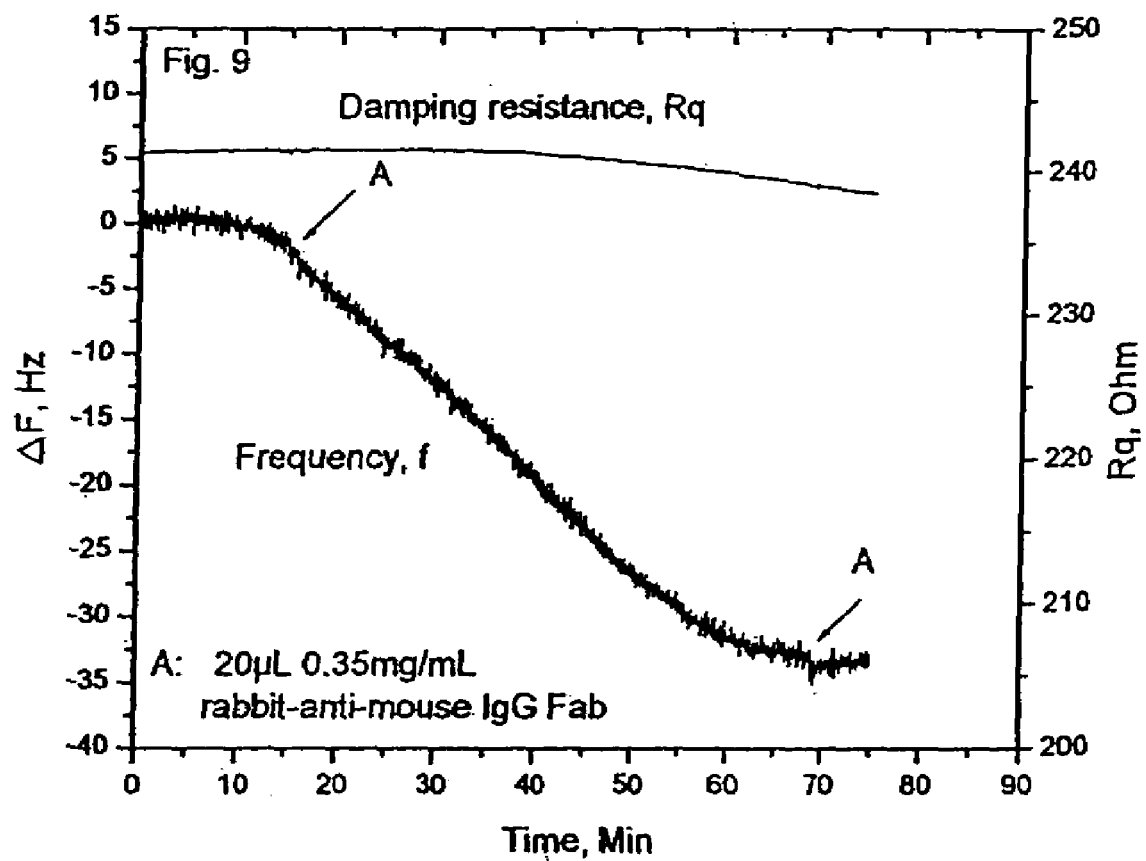
FIG. 30 shows frequency change vs. time when 20 uL of 0.35 mg/ml of rabbit IgG Fab was added to the A10B-scFv immobilized Au QCM electrode in 1 ml PBS buffer.
Figure 31:
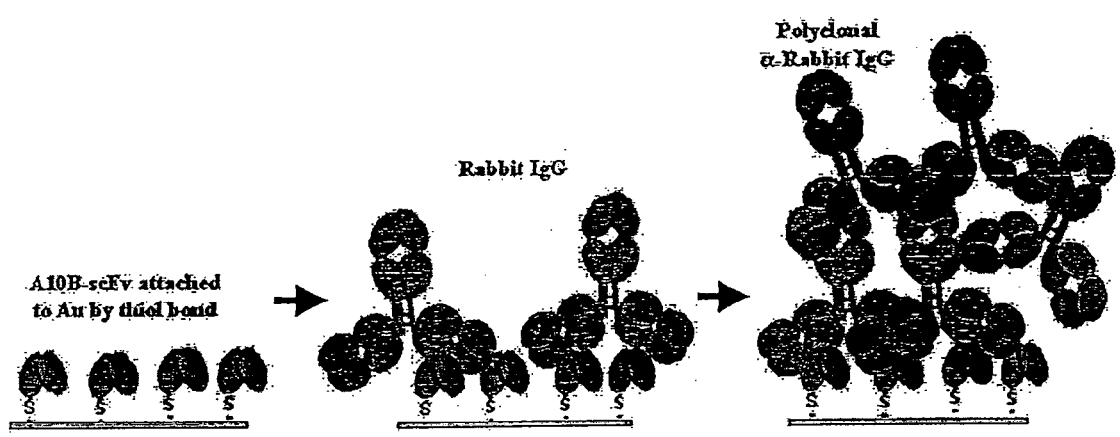
FIG. 31 is a cartoon of A10B-scFv capturing rabbit IgG followed by addition of polyclonal α-rabbit IgG.

The A10B antibody binds to the $C_H1$ region of rabbit IgG. The $C_H1$ region is located at the Fab portion of the rabbit IgG. In order to further confirm binding of scFv, we purchased rabbit IgG Fab from Jackson Immuno labs (catalogue #315-007-003). Since the Fab is only one-third the molecular weight of whole rabbit IgG, this study can further prove the sensitivity of the scFv-piezoimmunosensor. FIG. 30 shows that addition of rabbit IgG Fab to a A10B-scFv immobilized surface results in 25 Hz of frequency decrease. This further demonstrates that the scFvs can detect small antigens, such as toxins, e.g. Ricin toxin, 64 kD; Staphylococcal enterotoxin B, 28 kD; and Botulinum toxin, 190 kD.

Confirmation through sandwich assay: Since A10B-scFv binds to rabbit IgG, we used whole rabbit IgG in our assay, then added a secondary polyclonal α-rabbit IgG to bind to the rabbit antibodies captured by A10B-scFv. Detection of the secondary antibody further demonstrates the capture of antigen by the A10B-scFv on the Au QCM surface.

Figure 32:
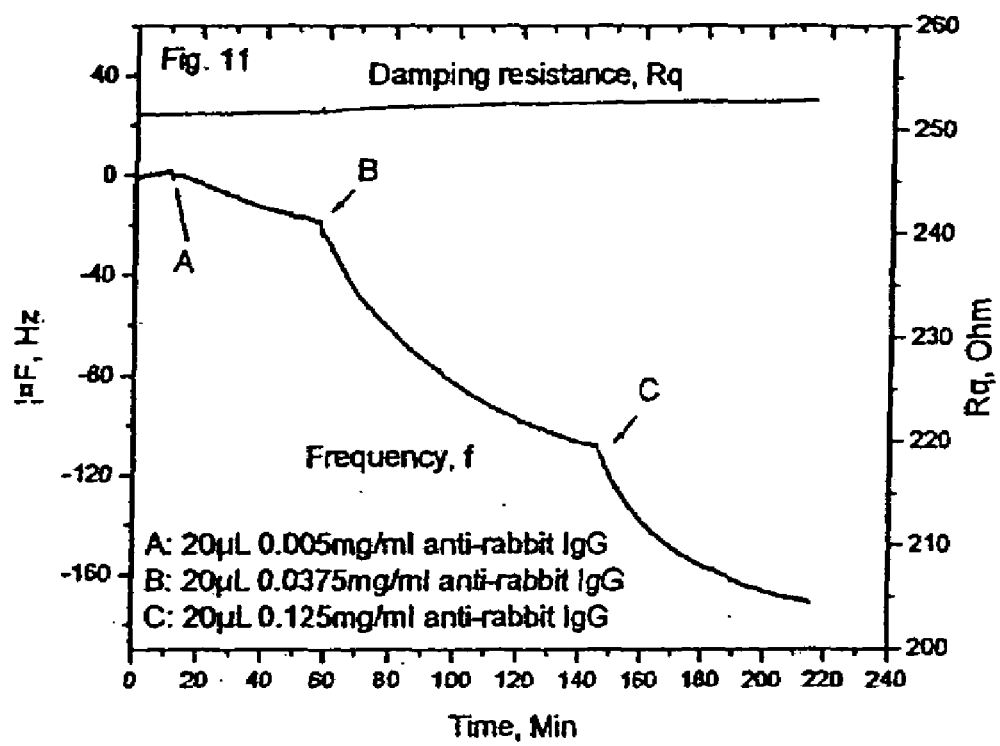
FIG. 32 shows the frequency change vs. time curve when polyclonal goat α-rabbit IgG was added to A10B-scFv immobilized Au QCM electrode after previously binding rabbit IgG in 1 ml PBS buffer. Electrode was washed with biograded water and PBS buffer then dried before the secondary binding with the α-rabbit IgG.

In the sandwich assay shown in FIG. 32, we observed about 3-4 times higher frequency decrease with the secondary antibody binding than previously observed with binding by A10B-scFv with the rabbit IgG. When scFvs are immobilized on the sensor surface, each scFv will either capture a single 150 kD rabbit IgG, share the antibody with a neighboring scFv (two binding sites per rabbit antibody), or inhibit binding of neighboring scFvs due to steric hindrance. The polyclonal goat anti-rabbit IgG contains a population of antibodies, each potentially binding to a different site on the rabbit IgG captured by the A10B-scFv. Therefore, the anti-rabbit IgG antibodies will bind to more than one site on a single rabbit IgG. As a consequence, 3-10 different (150 kd) anti-rabbit antibodies may bind to one rabbit IgG captured by one A10B-scFv on the surface. This significantly lowers the detection limit for this sandwish assay. The detection limit for this sandwish assay is $6.6 \times 10^{-10}$ M. Since goat α-rabbit IgG shows very little frequency decrease when it is added to the A10B-scFv immobilized Au surface (see section 2.3), the frequency decrease is due to specific binding to the captured rabbit IgG.

A sensor is selective if its signal is a function of only the amount of specific analyte present in the sample. Fetal Bovine Serum (FBS), goat α-human IgG, human $IgG_2$, α-rabbit IgG Fab fragments, yeast extract and goat α-rabbit IgG were used to test the specificity of the scFv piezoimmunosensor.

Figure 33:
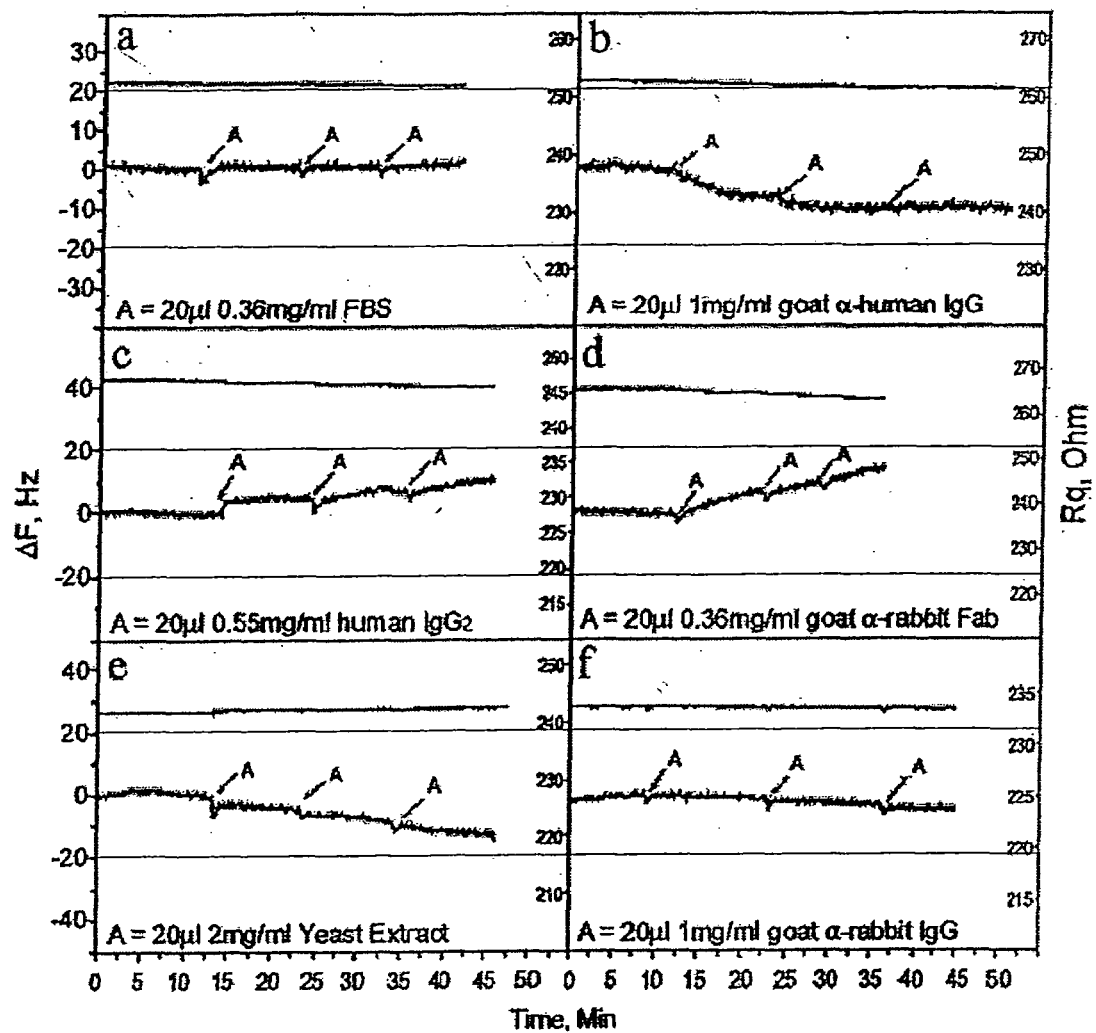
FIG. 33 shows a series of control experiments to look for non-specific binding. Frequency change vs. time curve when aliquot of (a) Fetal Bovine Serum (FBS) (GibcoBRL Cat # 16000-044), (b) goat α-human IgG, (c) human IgG$_2$, (d) goat α-rabbit IgG Fab fragments, (e) yeast extract (Difco, Bacto Yeast Extract, cat # 0127-01), (f) goat α-rabbit IgG were added to the A10B-scFv immobilized Au QCM electrode in 1 ml PBS buffer.

FIG. 33 is a series of negative control experiments in which aliquots of various analytes where added to the A10B-scFv sensor and examined for non-specific binding. Fetal bovine serum (a) and yeast extract (e) are complex mixtures, while the remaining samples are goat or human antibodies (A10B recognized rabbit antibodies). There was a small decrease in frequency with the goat α-Human IgG (b), possibly due to cross-reactive epitopes on the antibodies. However, yeast extract, FBS, and anti-rabbit IgG (f) gave an excellent baseline showing negligible non-specific binding. Since FBS and yeast extract are complex mixtures, similar to the types of samples we hope to test, we compared the A10B-scFv QCM sensor with the A10B monocolonal piezoimmunosensor for sensitivity and selectivity in FBS and yeast extract matrix.

The effectiveness of conventional piezoimmunosensors, which place whole antibodies as the sensing element on a QCM, is limited by non-specific binding and molecular trapping. In our experiments, nonspecific binding was observed when a 0.36 mg/ml concentration of FBS was added to A10B monoclonal immobilized Au QCM surface (FIG. 34), while the same concentration of FBS on A10B-scFv surface showed no detectable nonspecific absorption (FIG. 34).

Figure 34:
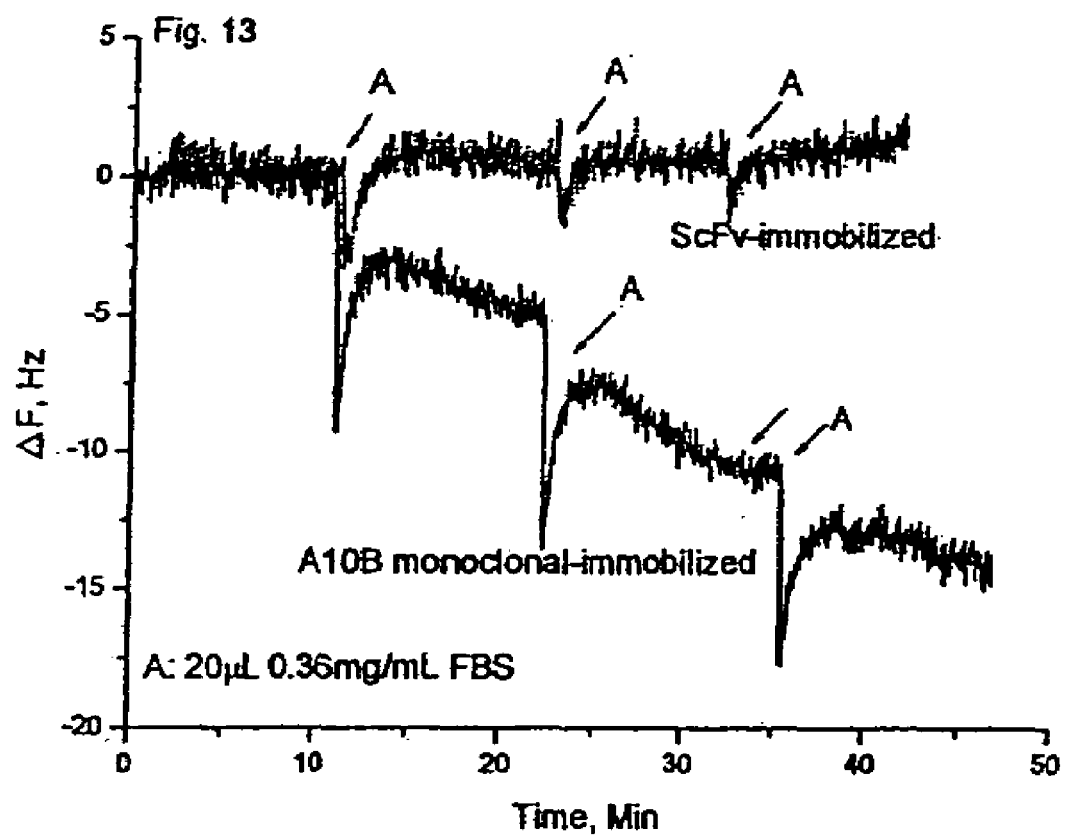
FIG. 34 shows a comparison of frequency change when a complex solute (FBS) is added to either the scFv or the parental antibody in the absence of specific antigen. Frequency change vs. time curve when 0.36 mg/ml FBS was added to A10B-scFv immobilized Au QCM surface or the A10B monoclonal immobilized Au QCM electrode in 1 ml PBS buffer separately.
Figure 35A:
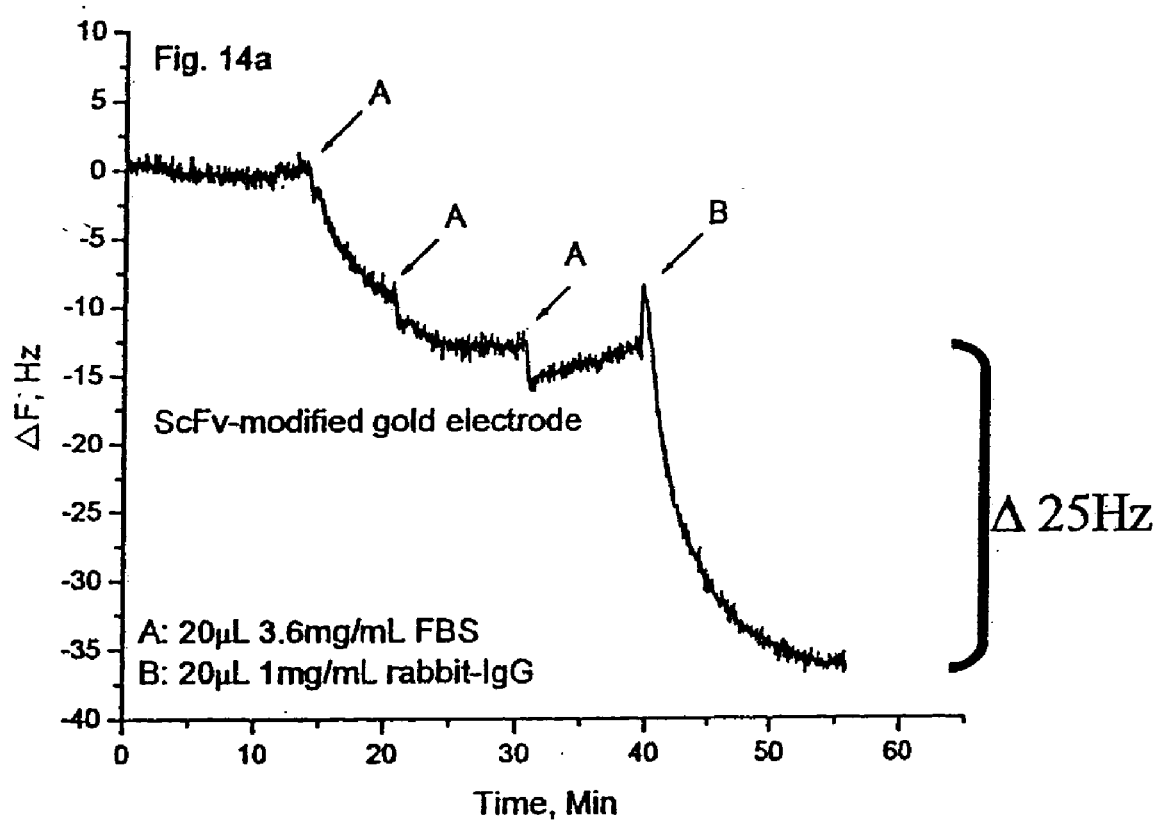
FIGS. 35A and 35B show a frequency change vs. time curve when 3.6 mg/ml FBS were added multiple times (FIG. 35A) in A10B-scFv and (FIG. 35B) A10B monocolonal antibody immobilized Au QCM electrode in 1 ml PBS buffer. 20 μl of 1 mg/ml rabbit IgG was then added to both samples to test antigen detection in a complex solute.
Figure 35B:
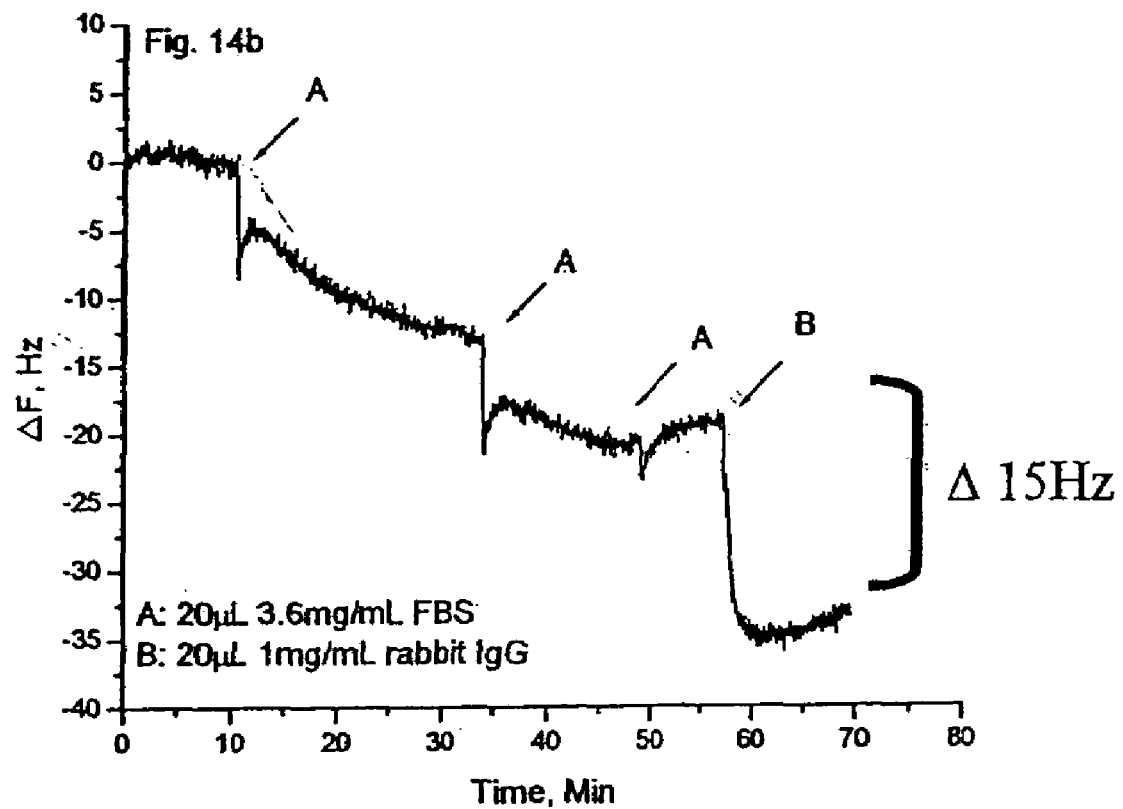

When a higher concentration of FBS (3.6 mg/ml, 10 times higher than experiment in FIG. 34 was added multiple times to either the A10B-scFv or the A10B monoclonal antibody sensors, higher nonspecific adsorption occurred with the whole antibody. Further, detection of the rabbit IgG in the FBS/PBS mixture was significantly inhibited in the dirty solute. The frequency change with the monoclonal A10B modified surface was only 15 Hz, compared with 25 Hz with the A10B-scFv modified Au QCM surface (FIG. 35).

Figure 36A:
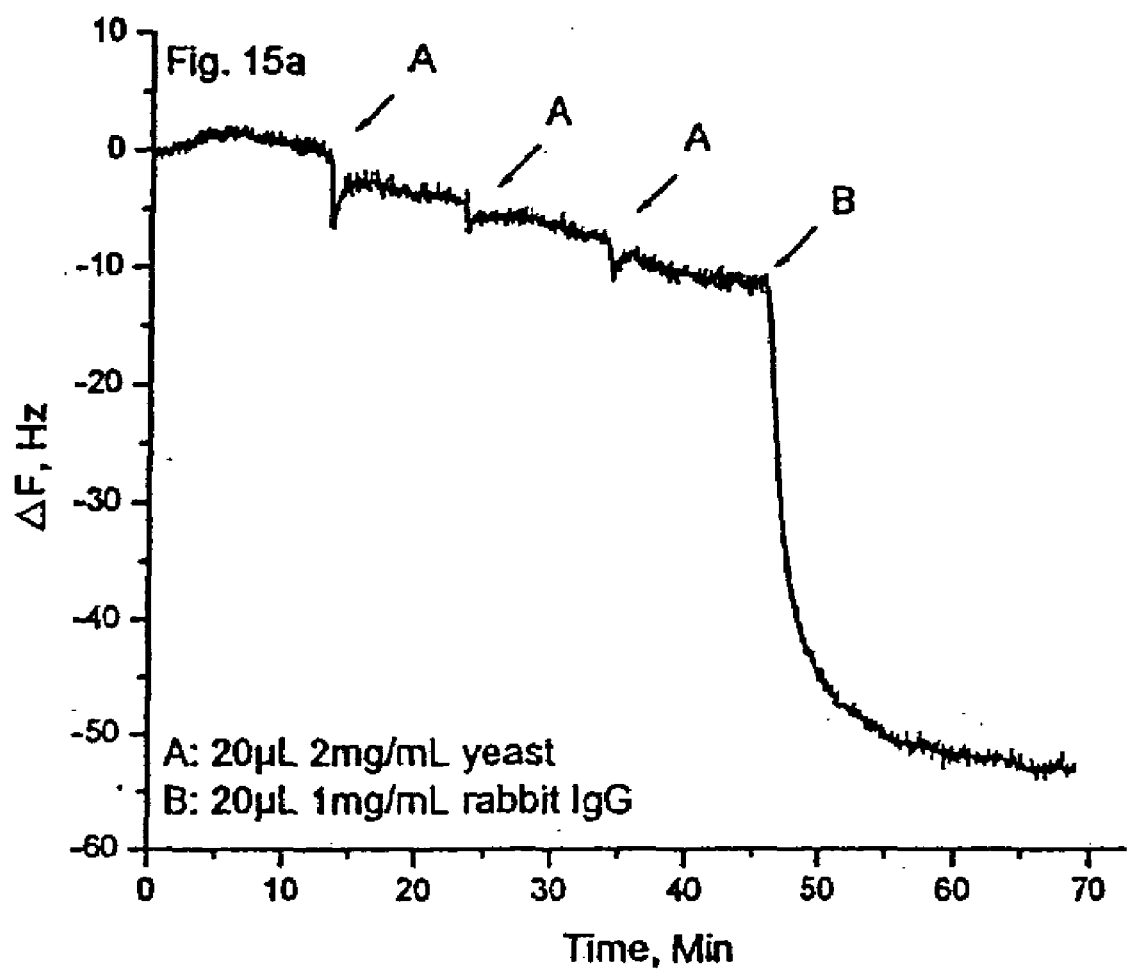
FIGS. 36A and 36B show a frequency changes vs. time curve when 2 mg/ml yeast extract were added multiple times to (FIG. 36A) A10B-scFv and (FIG. 36B) A10B monoclonal antibody immobilized on the QCM in 1 ml PBS buffer. 20 μl of 1 mg/ml rabbit IgG was then added to both samples to test antigen detection in a dirty matrix.
Figure 36B:
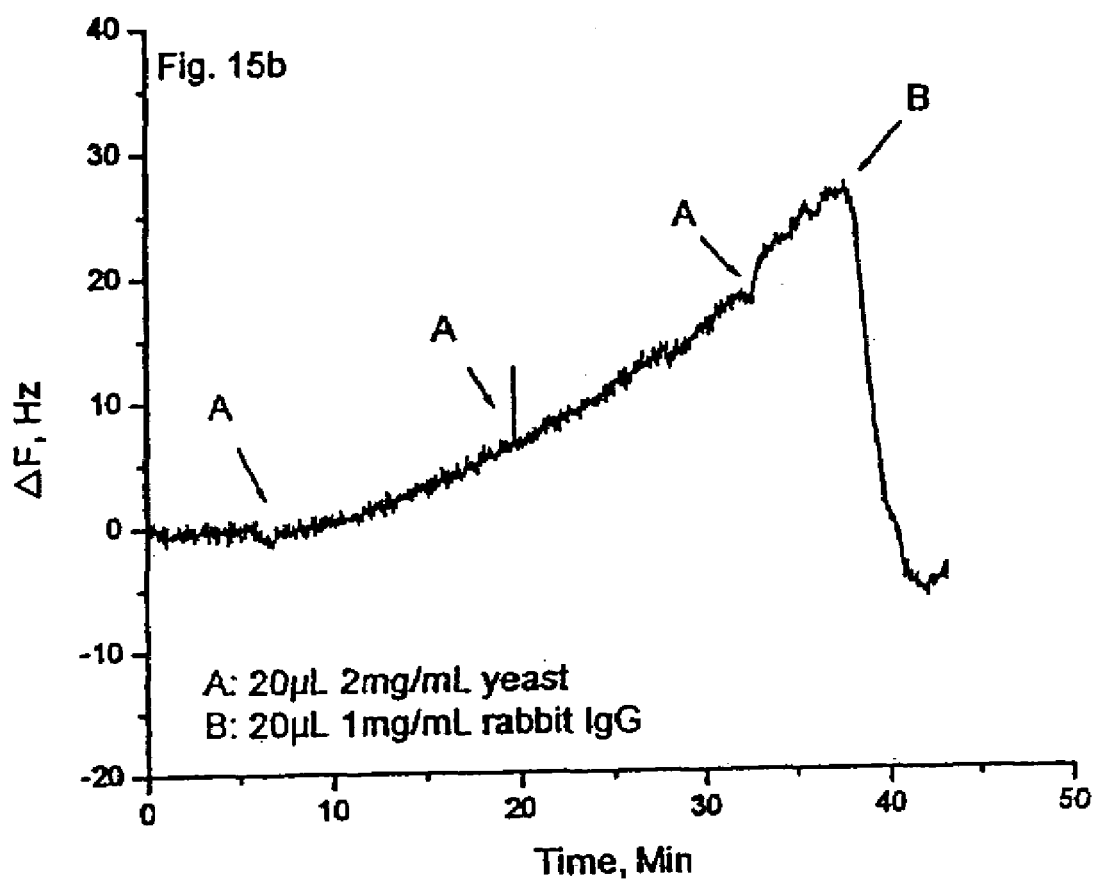

A second complex mixture was used to examine the behavior of the parental monoclonal antibody compared to the scFv cloned from it. A solution of 2 mg/ml yeast extract was added in 20 μl increments to the QCM with either A10B-scFv or the A10B monoclonal immobilized on the surface (FIG. 36). Adding three 20 uL aliquots of yeast extract to the scFv results in less than 10 Hz of non-specific binding (FIG. 36). While in this dirty matrix, addition of antigen, rabbit IgG, results in a 43 Hz frequency decrease on the scFv surface. Adding yeast extract to the A10B monoclonal antibody immobilized on the QCM surface (FIG. 36) resulted in an increase in the frequency, indicating that the A10B monoclonal is dissociating from the sensor surface. Since the A10B antibody is immobilized by physical adsorption, it is possible that debris in the yeast extract displaces the A10B from the surface. Addition of the rabbit IgG antigen to this surface resulted in a frequency decrease that indicates binding of rabbit IgG with the whole monoclonal A10B. However, due to the instability of the monocolonal antibody on the surface, the detection is less sensitive than the scFv immobilized QCM sensor. This ability to detect antigen in a complex/dirty solute further demonstrates the potential sensitivity and selectivity of scFv piezoimmunosensors.

Figure 37:
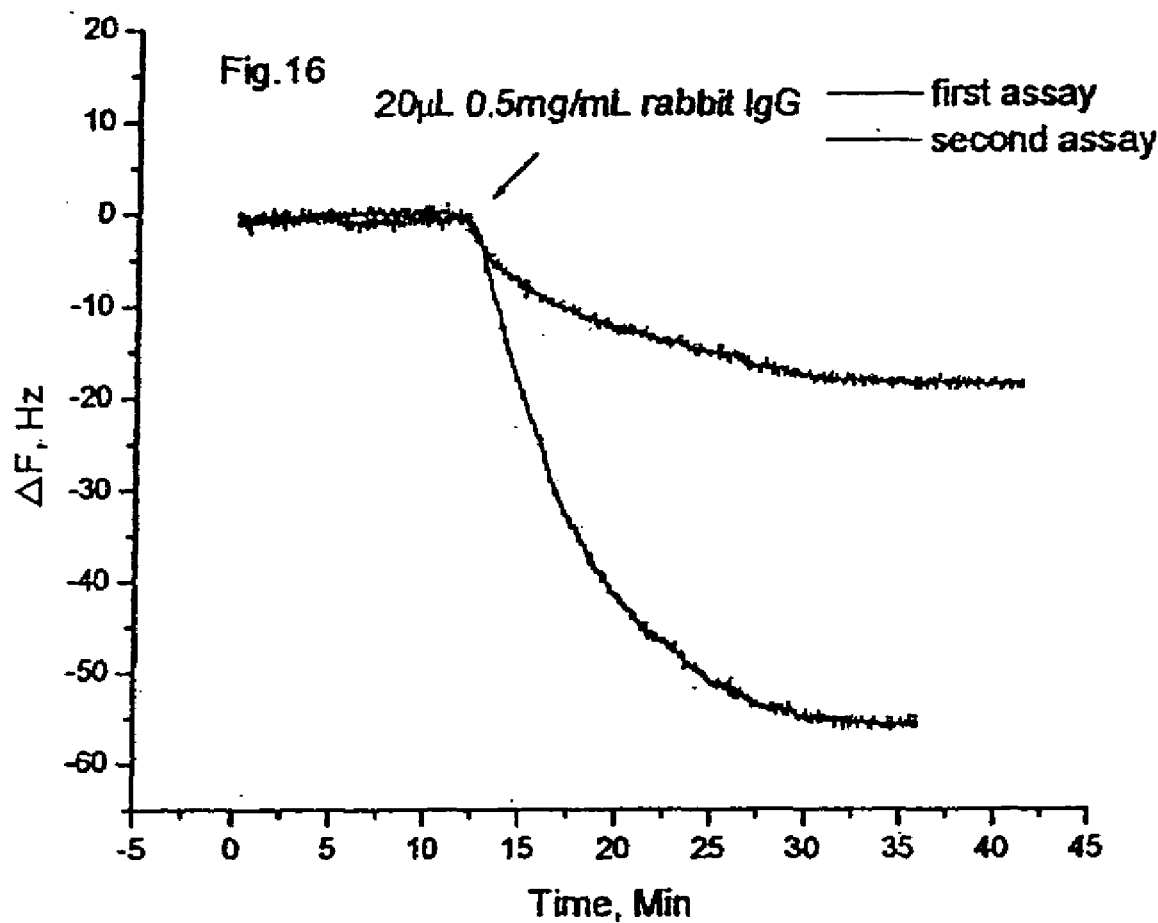
FIG. 37 shows frequency change vs. time (a) when 20 μl of 0.5 mg/mL rabbit IgG were added to the electrode surface immobilized with scFv (b) regenerated scFv surface with 0.5% glacial acetic acid in 1 ml PBS buffer and used for the new assay.
Figure 38:
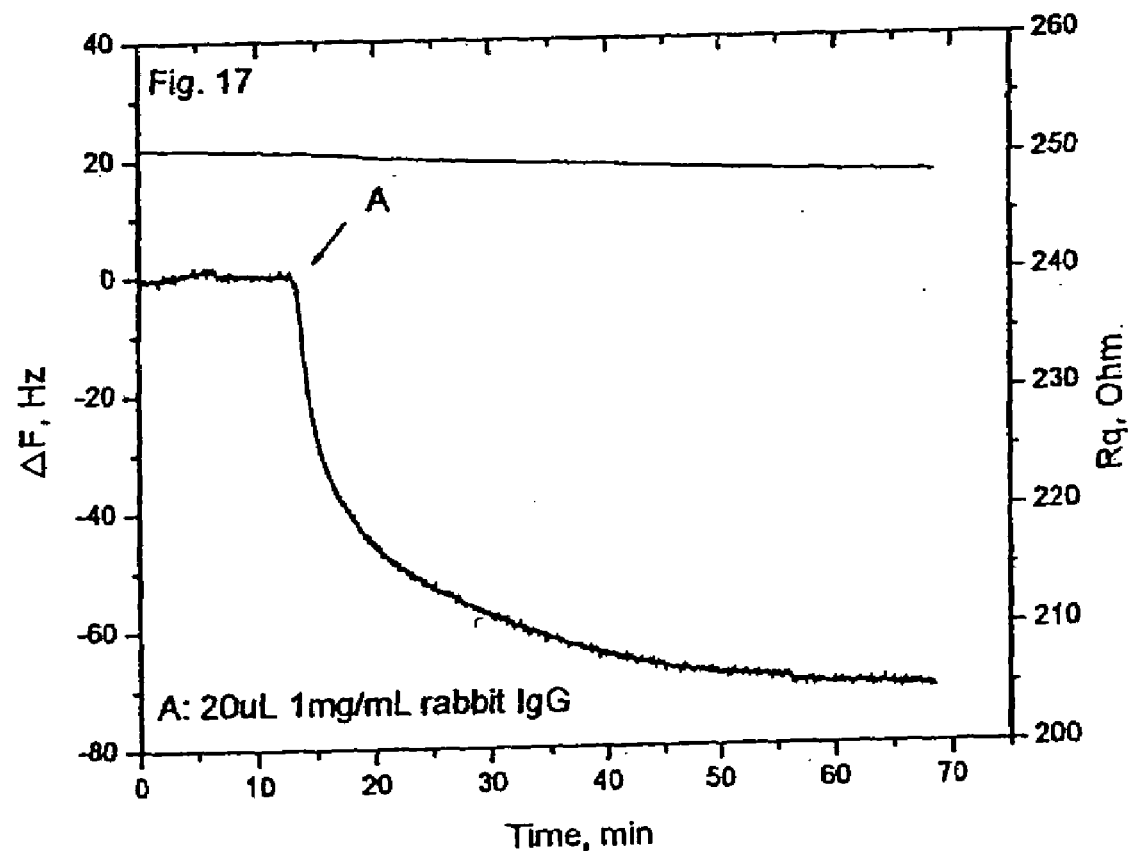
FIG. 38 shows frequency change vs. time when 20 μL of 1 mg/mL rabbit IgG were added to the electrode surface regenerated by stripping the whole A10BscFv-rabbit-IgG conjugate gold surface.
Figure 39:
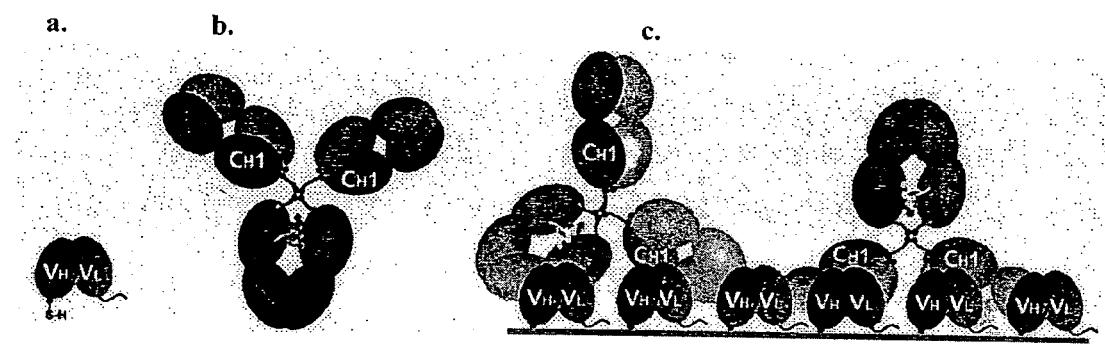
FIG. 39 shows (a) A10B-scFv with incorporated cysteine residue in the linker located at the bottom of the variable heavy (V$_H$) domain. This α-rabbit IgG-scFv recognizes the constant heavy chain 1 (C$_H$1) domain of rabbit IgG. (b) Rabbit IgG with the C$_H$1 domain labeled. (c) Schematic of the α-rabbit-scFvs, covalently bound to the gold surface of the QCM through the incorporated cysteine, binding antigen.
Figure 40:
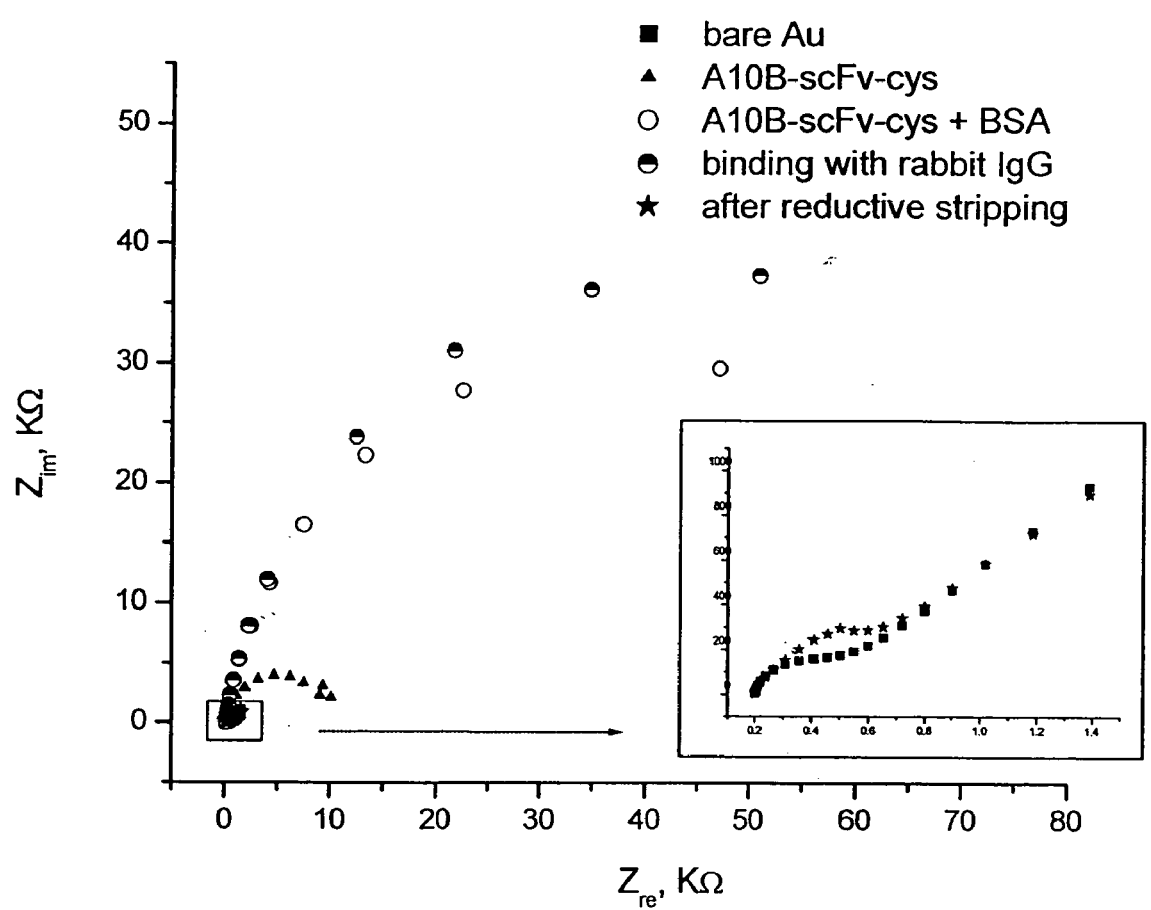
FIG. 40 shows Nyquist plots curve obtained in a solution of 0.1M NaClO$_4$ containing 1 mM K$_4$Fe(CN)$_6$/K$_3$Fe(CN)$_6$. Bare gold electrode (black); A10B-scFv-cys immobilized gold electrode; A10B-scFv-cys+BSA-immobilized gold electrode; the A10B-scFv-cys+BSA surface binds with rabbit IgG; The gold electrode after removal of the scFvs by reductive stripping.
Figure 41A:
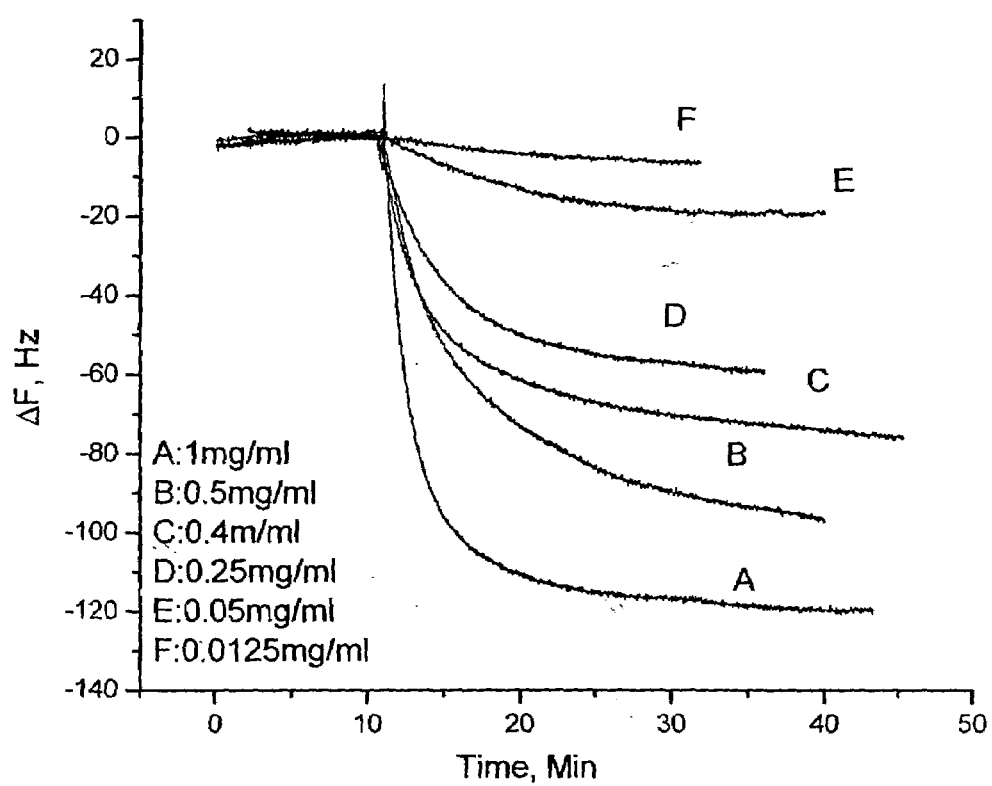
FIGS. 41A-41C show frequency change in hertz for the QCM electrode.
Figure 41B:
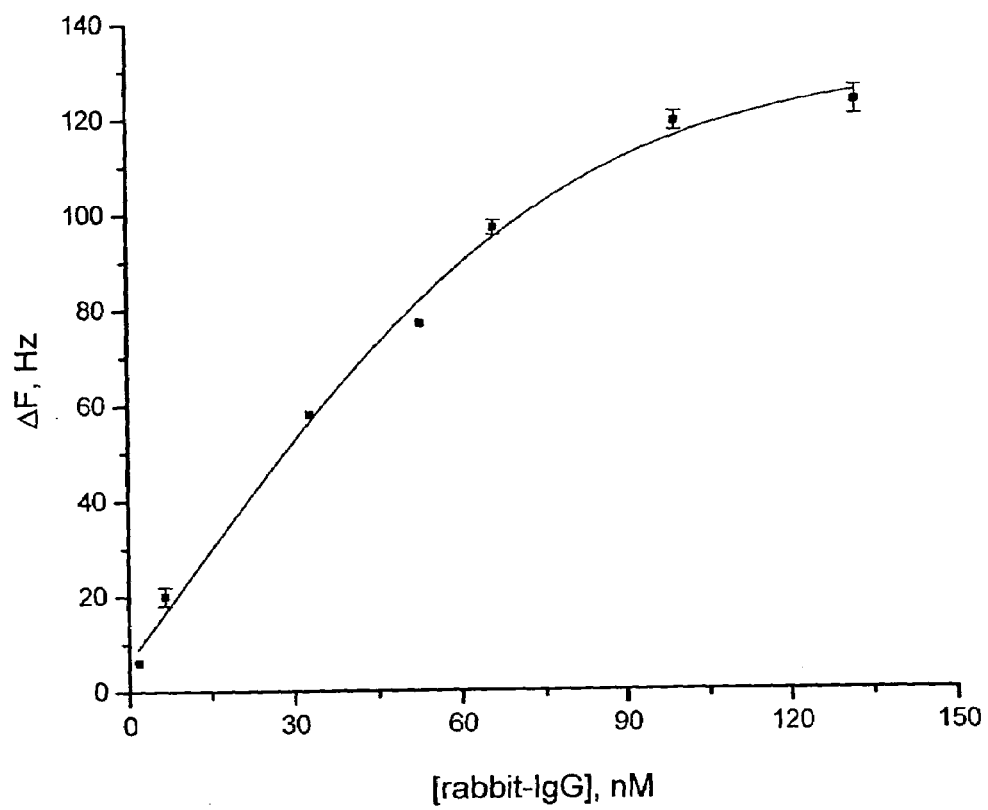
Figure 41C:
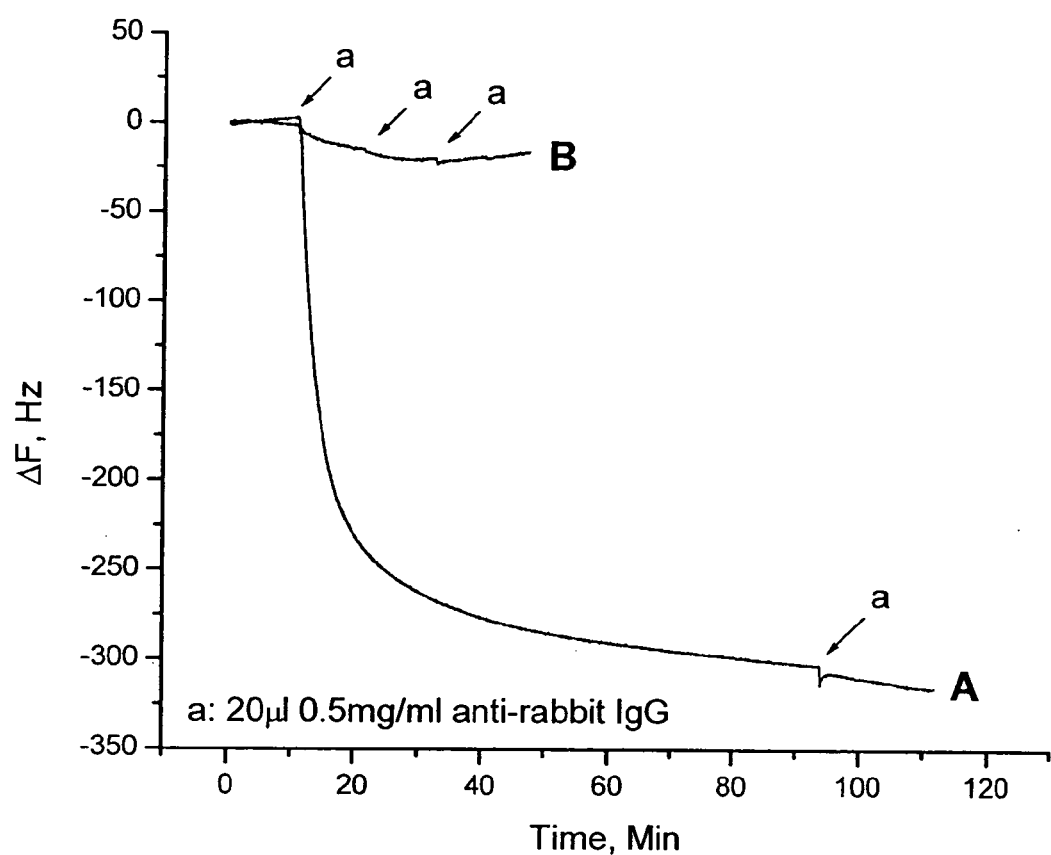
Figure 42:
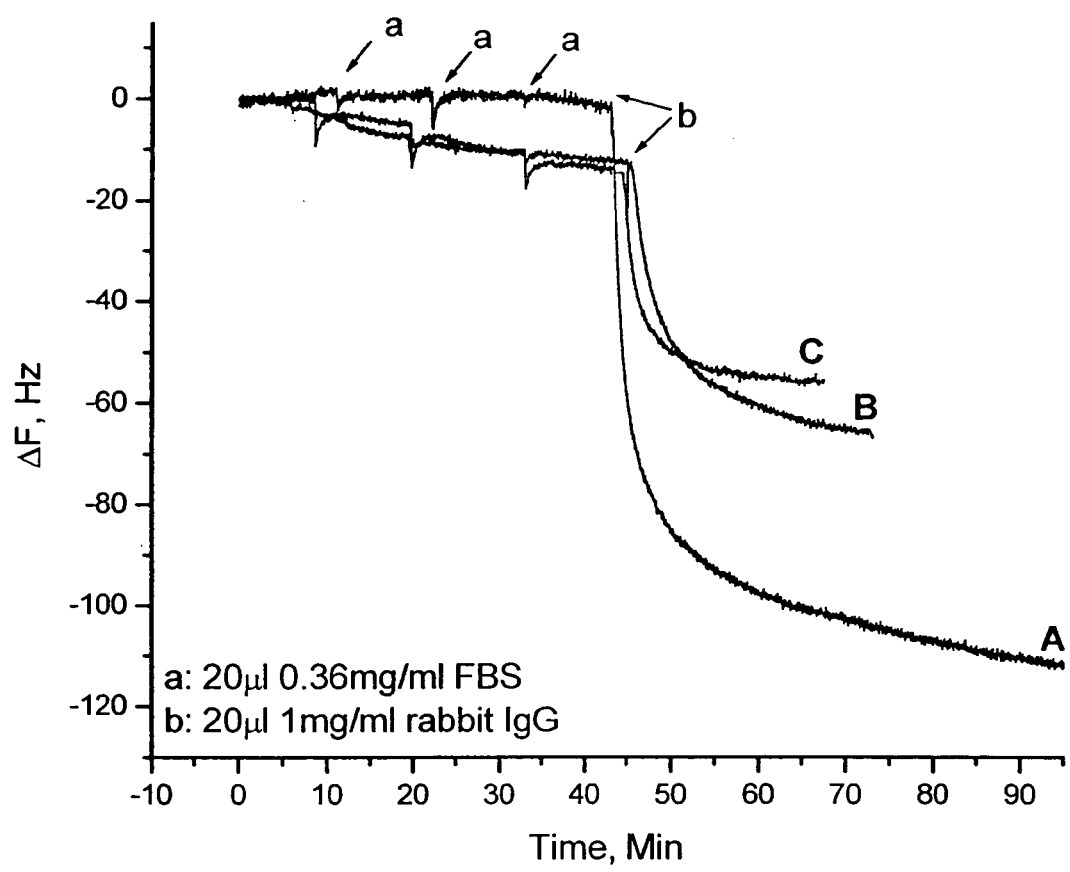
FIG. 42 is a comparison of sensor selectivity, sensitivity for three PZ: A10B-scFv-cys, A10B-scFv, and A10B monoclonal antibody in 1 ml PBS buffer respectively a. 20 μl 0.36 mg/ml FBS was added three times; b. then 20 μl of 1 mg/ml rabbit IgG was added to test antigen detection in a complex matrix. A: scFv immobilized, B: A10B whole antibody immobilized, C: scFv without cysteine linker immobilized gold surface.
Figure 43:
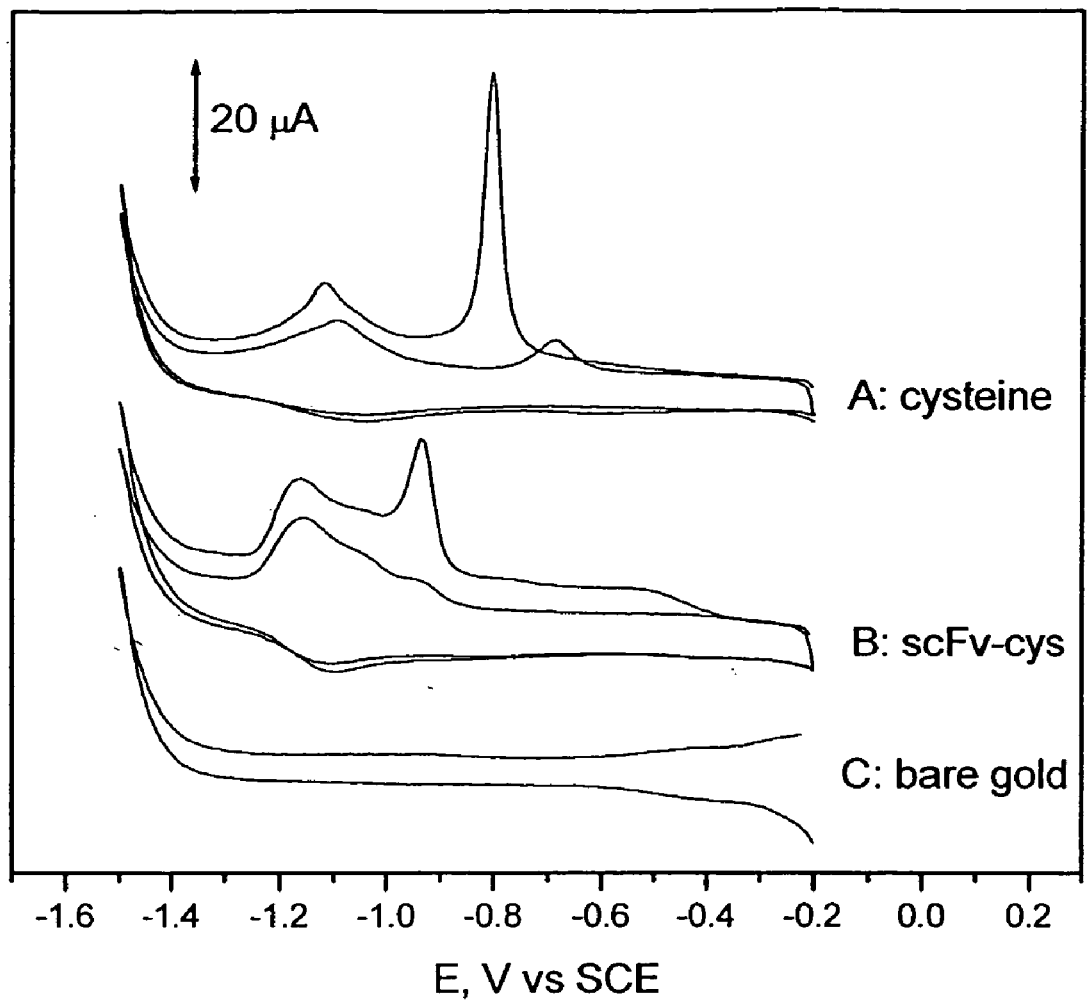
FIG. 43 shows cyclic voltammograms obtained in 0.5 M KOH aqueous solution at a scan rate of 100 mV/s. Nitrogen purge for 15 mins to remove the dissolved oxygen. Two cycles are shown. A: cysteine-modified gold electrode; B: scFv-cys modified gold electrode; C: bare gold electrode. The counter electrode is a Pt wire.
Figure 44:
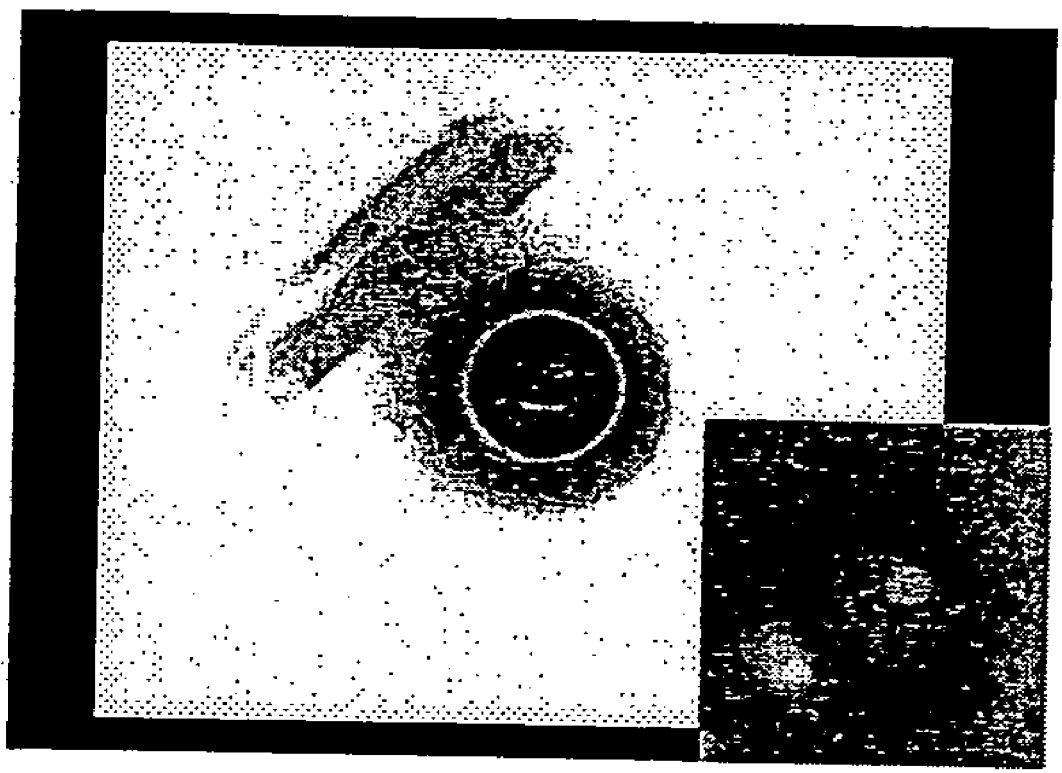
FIG. 44 is a photograph of HRP immunoassay on the A10B-scFv-cys immobilized Au surface (7.1×10$^-$mg/ml anti-E-tag HRP added on the scFv immobilized Au surface. After an hour, wash with PBS buffer and dried with nitrogen, then apply ABTS/H$_2$O$_2$ solution, 1.8 microliter of 30% H$_2$O$_2$ to each ml of ABTS). Insert in right corner is the control experiment done on the Au surface with immobilized mannose with thiol linker.

For individual sensors, reversibility is not critical as piezoimmunoassay is inexpensive, i.e., it is affordable to use disposable transducers. However, it is important to study the reversibility of the binding reaction to assess the feasibility of continuous monitoring without calibration. We have tested the reversibility of the scFv piezoimmunosensor by removing the bound rabbit IgG conjugates with a low pH acetic acid solution (0.5% glacial acetic acid)[1]. FIG. 37 shows the frequency-time response upon addition of rabbit IgG to a regenerated A10B-scFv surface by dissociation of A10B-scFv rabbit IgG conjugated with a mild acid. This experiment shows that washing with a low pH solution does not significantly harm the immobilized scFvs, but it causes some degradation. Consequently, we tried to remove the whole antigen-scFv complex and add new scFvs to the crystals for a new assay. Since the formation of scFv-SAM is based on the chemisorption of the incorporated cysteine's sulfur atom onto the gold surface, scFv-SH+Au→scFv-Au+e+H$^+$, the scFv-SAM can be removed from the metal surface through a reductive desorption. FIG. 38 is the frequency and time curve for the freshly relabeled crystals for a new assay after electrochemical reductive desorption of the antigen-scFv complex. Upon addition of 20 uL 1 mg/ml rabbit IgG, we observed the same 70 Hz frequency decrease. Even though this practice proved successful, for biohazard detection we recommend disposal of the QCM sensor after each use due to contamination.

Network Impedance Analysis: The QCM has been explored as an alternative to optical biosensors in recent years for detection of biological reagents[3]. However, some researchers are still skeptical about the potential of piezoelectric mass sensing devices as biosensors[i] because the physics of biofilms in liquids is complex. This complexity makes it difficult to obtain an explicit relationship between the added mass and change in the frequency output. Generally, the QCM gives a response that characterizes the binding event between a sensing layer, immobilized on the surface of the transducer, and the analytes to be detected. However, the mass estimated with the QCM response through the Sauerbrey equation[4] ($\Delta f=-2\Delta mnf_o^2/[A(\mu_q P_q)^{1/2}]$, where n is the overtone number, $\mu_q$ is the shear modulus of the quartz ($2.947 \times 10^{11}$ g/(cm sec$^2$), $p_q$ is the density of the quartz (2.648 g/cm$^3$), and $\Delta m/A$ is the areal density), for a 10M Hz quartz crystal, the sensitivity is 0.226 Hz cm$^2$/ng depending on the layer rheology. The Sauerbrey relationship was derived by assuming the attached mass is rigid and strongly coupled to the resonator. It does not apply if the deposited mass is, for example, viscoelastic. Quartz crystal resonators are sensitive to viscoelastic properties[3], which limits QCM application for the precise mass detection of biological materials in a liquid phase. In such cases, the true mass and that calculated using the Sauerbrey relationship may be quite different.

We have demonstrated the success of this method by determining the crystal impedance of the resonator with and without the attached biofilms and shown that series resistance in the Butterworth-Van-Dyek-equivalent circuit changes little. This result is proof that the attached biofilms behaves as a rigidly attached mass and that the Sauerbrey equation is valid. A QCM acoustic impedance analysis was used to determine changes in energy loss upon the binding events shown in FIGS. 24, 28-30, and 33-38, i.e., the binding of A10B-scFv and the parental monoclonal A10B antibody with rabbit IgG, and secondary binding of anti-rabbit IgG with the rabbit IgG captured by A10B. Table 4 lists the changes of damping resistance for these experiments. The data demonstrates that the change of damping resistances in all cases was $\Delta R_q/R_q>1.1\%$, which confirmed that the biofilms were exhibiting rigid, rather than viscoelastic, behavior in our experiments.

TABLE 4

Changes of damping resistances for experiments (FIGS. 24, FIGS. 28-30, FIGS. 33-38).

| Figure | $|\Delta Rq|/Rq$ | Figure | $|\Delta Rq|/Rq$ | Figure | $|\Delta Rq|/Rq$ |
|---|---|---|---|---|---|
| 24 | 0.3% | 28A | 0.5% | 29 | 1.1% |
| 30 | 1.1% | 32 | 0.5% | 33 (panel a) | 0.3% |
| 33 (panel b) | 0.1% | 33 (panel c) | 0.6% | 33 (panel d) | 0.6% |
| 33 (panel e) | 0.9% | 33 (panel f) | 0.4% | 34 | 0.2% |
| 35A | 1.1% | 35B | 0.5% | 36A | 0.2% |
| 36B | 0.2% | 37 | 0.2% | 38 | 1.0% |

In the present invention scFv-SAMs can be used for detection the of a toxin (e.g., botulism toxin tainted food), a virus (e.g., HIV contaminated blood), a bacterium (e.g., *E. coli*), and a protozoan (e.g., *Cryptosporidium parvum* contaminated water). Phage display can be used to develop two distinct scFvs (recognizing different antigens on the same agent) for each agent to be detected. Using two distinct sensors to detect the same organism should reduce false positives.

EXAMPLE 4

In this example, A10B ScFv having the linker sequence CGGGSGGGGSGGGGS (SEQ ID NO:20) was used to generate data for FIGS. 39-47.

Figure 45:
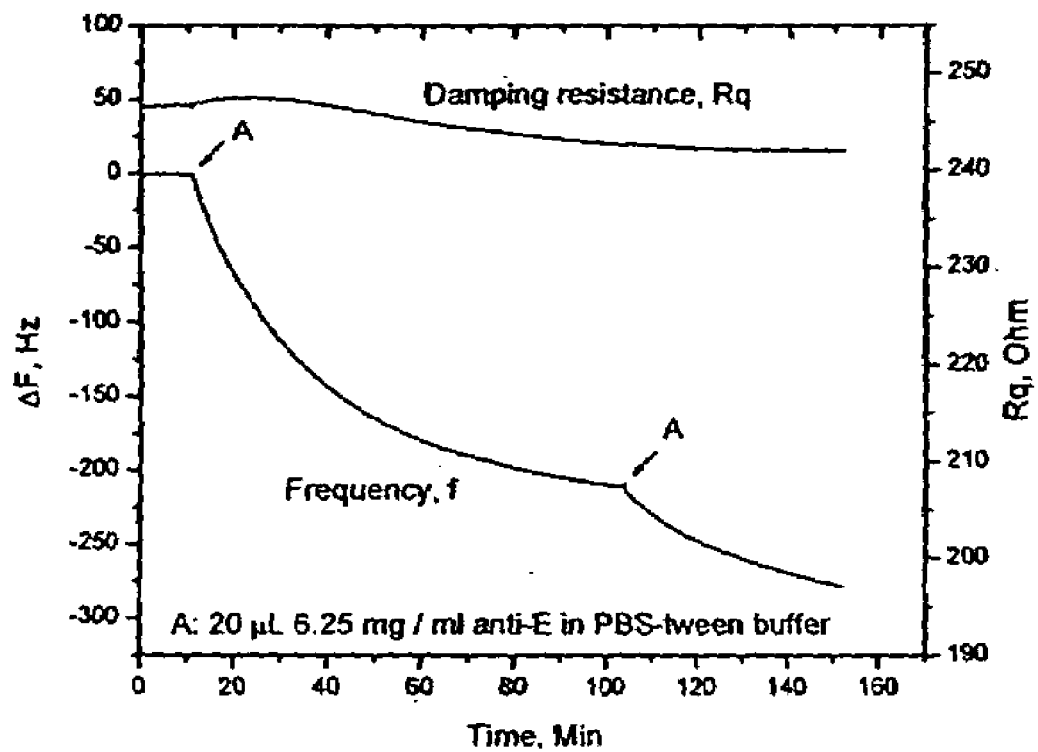
FIG. 45 shows frequency change vs. time curve when 20 μL 6.25 mg/ml of conjugated rat anti-rabbit IgG was added to the A10B scFv immobilized Au surface of the QCM in 1 mL PBS buffer. A: 20 microliters of 6.25 mg/ml anti-E in PBS-Tween buffer.
Figure 46:
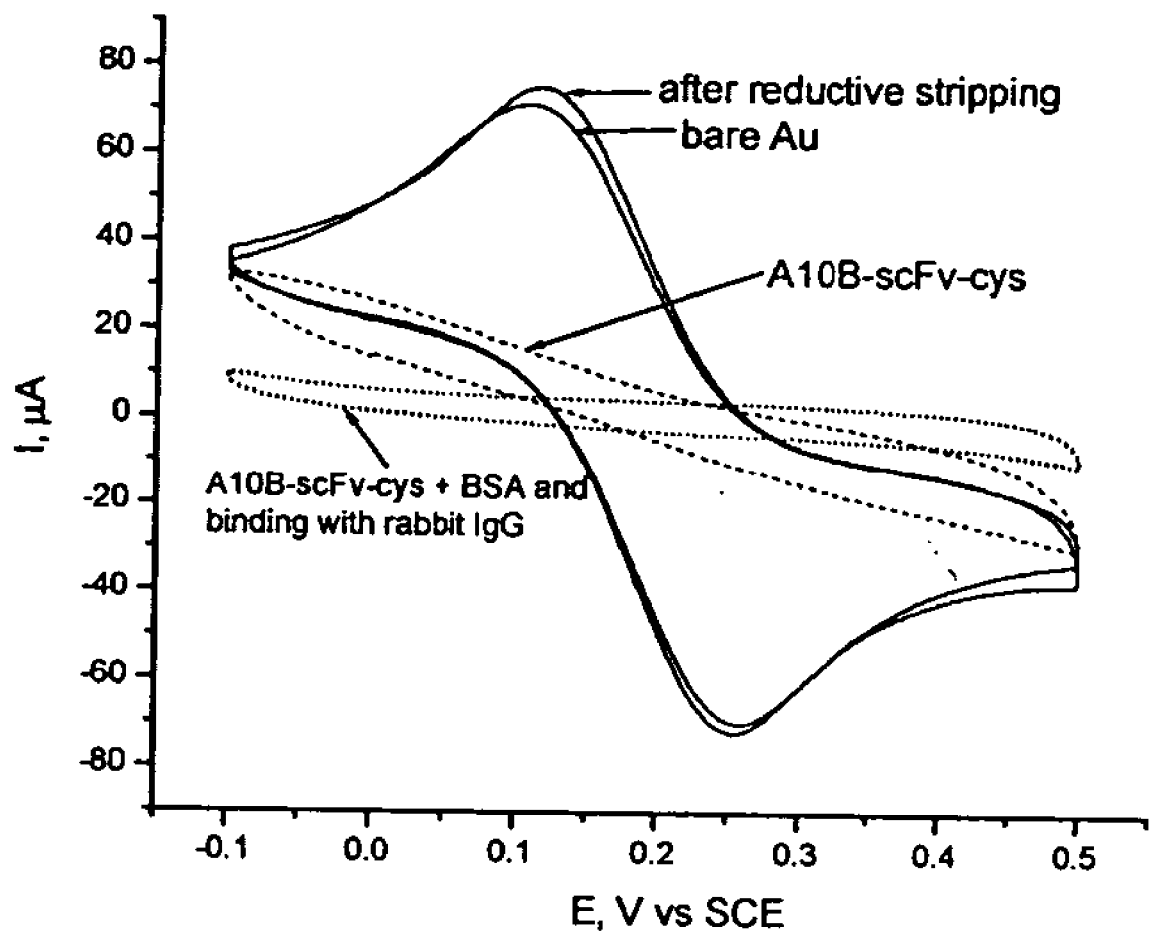
FIG. 46 shows cyclic voltammograms in a solution of 0.1M sodium perchlorate containing 1 mM K$_4$Fe(CN)$_6$/K$_3$Fe(CN)$_6$, scan rate: 100 mV/s at bare gold electrode; scFv-cys immobilized gold electrode; scFv-cys+BSA-immobilized gold electrode; the scFv-cys+BSA surface binds with rabbit IgG and the gold electrode after removal of the scFv-cys by reductive stripping in 0.5M KOH. The counter electrode is a Pt wire.

HRP immunoassay: The A10B-scFv-cys has an E-tag incorporated on the amino terminus of the protein (E-tag: GAPVPYPDPLEPR). An E-tag is a specific linear epitope recognized by commercially available HRP conjugated anti-E-tag antibody. This feature allowed directly test for the binding of the A10B-scFv-cys on the Au surface by means of a calorimetric assay. If the A10B-scFv-cys is bound to the Au surface, the HRP conjugated anti-E-tag antibody will turn green when ABTS and hydrogen peroxide solution are added. The green color shown in FIG. 44 confirms the successful immobilization of A10B scFv-cys on the Au surface. In a second experiment to demonstrate the presence of the scFv on the gold surface, anti-E-tag HRP was added to the A10B-scFv immobilized Au QCM electrode. The decrease in frequency, due to binding to the E-tag, upon each addition of anti-E-tag HRP is shown in FIG. 45.

Electrochemical Probe by Cyclic Voltammetry (CV): We also used $K_4Fe(CN)_6/K_3Fe(CN)_6$ to probe the integrity of the scFv-SAM on the gold surface by cyclic voltammetry. Shown in FIG. 46, CV of bare Au surface gave ideal $K_4Fe(CN)_6/K_3Fe(CN)_6$ reversible redox peaks. Faradaic current is dramatically attenuated on the scFv-modified surface. Subsequent exposure of these scFv-SAMs to 0.1% BSA blocking reagent, then rabbit IgG resulted in a further increase in passivation. Stripping of the scFv-cys monolayer by reductive desorption renewed the fresh gold surface. These experiments demonstrated that a SAM of scFvs forms an impermeable barrier to electroactive species in aqueous electrolyte and that a primary mode of electrochemical communication between the electrode and the solution electrophore occurs at defect sites rather than by conduction through the monolayer.

Figure 47:
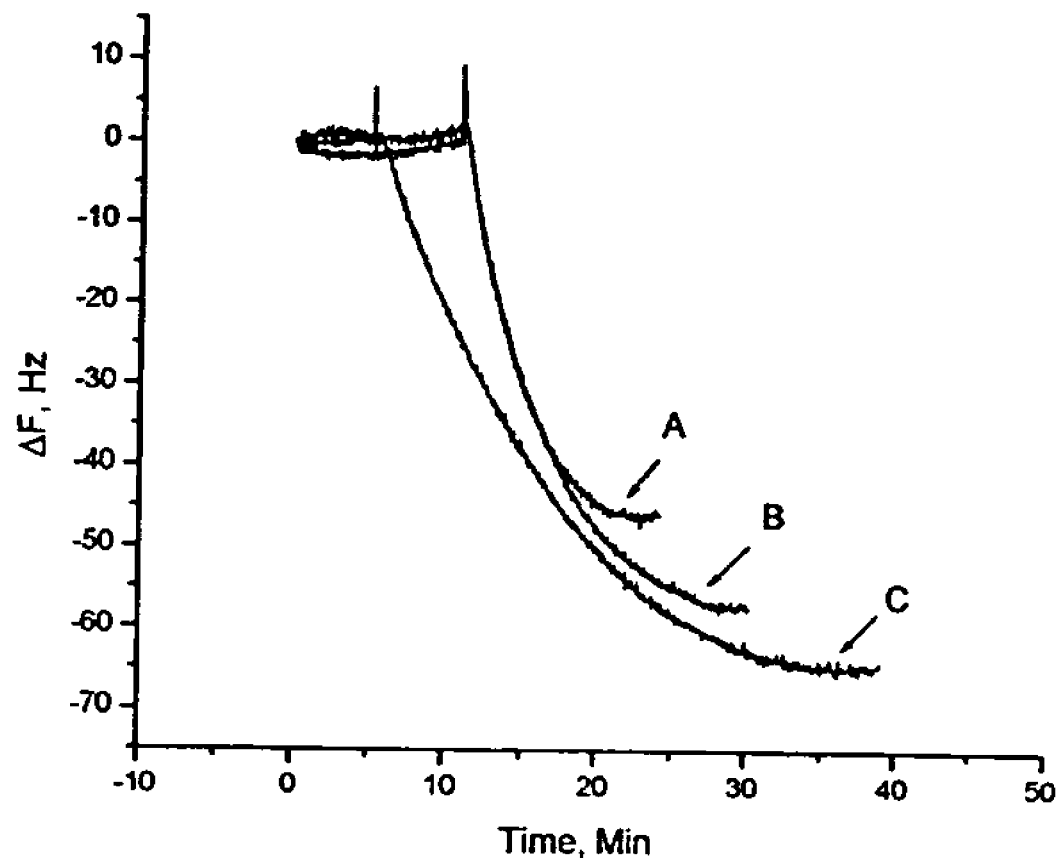
FIG. 47 shows rabbit serum analysis by A10B-scFv-cys PZ. Rabbit serum stock sample solution: rabbit serum sample diluted 100 times by PBS+0.1% Tween buffer. (A): mixture of 10 μl of Rabbit serum stock sample solution+10 μl of 0.25 mg/ml rabbit IgG (B): mixture of 10 μl of Rabbit serum stock sample solution+10 μl of 0.4 mg/ml rabbit IgG (C): mixture of 20 μl of Rabbit serum stock sample solution+ 20 μl of 0.2 mg/ml rabbit IgG. The average value for three measurements was 11.5±0.8 mg/ml.

QCM standard addition experiment for analysis of rabbit serum: The rabbit serum sample was spiked with a known amount of standard and analyzed by by scFv-cys-PZ as shown in FIG. 47.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. An apparatus for immunochemical detection of an analyte, comprising:
a piezoelectric mass sensor with at least one receptor layer which provides a receptor surface and which has immobilized on the receptor surface a layer of recombinantly derived polypeptide molecules which bind the analyte, wherein each of the molecules comprises a single antibody variable heavy chain ($V_H$) or single-chain Fv (scFv) polypeptide specific for the analyte and an attachment polypeptide which provides assembly of the molecules into the layer so as to be immmobilized on the receptor surface.

2. The apparatus of claim 1 wherein the recombinant polypeptide molecules bind a first epitope of the analyte and the apparatus comprises a second piezoelectric mass sensor with at least one second receptor layer which provides a second receptor surface and which has immobilized on the receptor surface a second layer of recombinantly derived polypeptide molecules which bind a second epitope of the analyte, wherein each of the molecules comprises a single antibody variable heavy chain ($V_H$) or single-chain Fv (scFv) polypeptide specific for the second epitope and an attachment polypeptide which provides assembly of the molecules into the layer so as to be immmobilized on the second receptor surface.

3. The apparatus of claim 1 wherein the apparatus comprises a control piezoelectric mass sensor with at least one receptor layer which provides a receptor surface and which has immobilized on the receptor surface a layer of recombinantly derived polypeptide molecules which bind the analyte, wherein each of the molecules comprises a single antibody variable heavy chain ($V_H$) or singlechain Fv (scFv) polypeptide specific for the analyte and an attachment polypeptide which provides assembly of the molecules into the layer so as to be immmobilized on the receptor surface wherein binding of the analyte is blocked by a blocking agent.

4. The apparatus of claim 1, 2, or 3 wherein the single antibody VH polypeptide specific for the analyte is derived from a library of single domain camel or llama antibodies and the amino terminus of the attachment polypeptide is linked to the carboxy terminus of the VH polypeptide.

5. The apparatus of claim 1, 2, or 3 wherein the scFv polypeptide specific for the analyte comprises an antibody variable light chain ($V_L$) polypeptide specific for the analyte and an antibody variable heavy chain ($V_H$) polypeptide specific for the analyte which are covalently linked through a polypeptide linker such that the variable light and heavy polypeptide chains are linked together while still maintaining a conformation which allows the binding of the analyte and the amino terminus of the attachment polypeptide is covalently linked to the carboxy terminus of the $V_L$ polypeptide.

6. The apparatus of claim 5 wherein the polypeptide linker is covalently linked to an amino terminus of the $V_L$ polypeptide and a carboxy terminus of the $V_H$ polypeptide such that the $V_L$ and $V_H$ polypeptide chains are linked together.

7. The apparatus of claim 1 wherein the sequence of the attachment polypeptide comprises at least one cysteine amino acid which provides a sulfhydryl moiety which allows the recombinantly derived polypeptide molecule to bind the receptor surface of the sensor to provide the layer on the receptor surface of the sensor.

8. The apparatus of claim 1 wherein the attachment polypeptide comprises a polypeptide or biotin strep-tag sequence, which allows the recombinantly derived polypeptide molecule to bind streptavidin, and the receptor surface of the sensor comprises a biotin layer immobilized on the receptor surface by a sulfhydryl linkage which binds the streptavidin bound to the recombinantly derived polypeptide molecule to provide the layer on the receptor surface of the sensor.

9. The apparatus of claim 1 wherein the attachment polypeptide comprises a polypeptide sequence for binding biotin, which allows the recombinantly derived polypeptide molecule to bind streptavidin, and the receptor layer comprises a biotin layer immobilized on the receptor surface by a sulfhydryl linkage which binds the streptavidin bound to the recombinantly derived polypeptide molecule to provide the layer on the receptor surface of the sensor.

10. The apparatus of claim 1 wherein the receptor layer comprises an electrode for the piezoelectric mass sensor.

11. The apparatus of claim 1 wherein the piezoelectric mass sensor is a quartz crystal microbalance.

12. A method for immunological detection of an analyte in a liquid sample, comprising:
 (a) providing an apparatus which comprises a piezoelectric mass sensor with at least one receptor layer which provides a receptor surface and which has immobilized on the receptor surface a layer of recombinantly derived polypeptide molecules which bind the analyte, wherein each of the molecules comprises a single antibody variable heavy chain ($V_H$) or single-chain Fv (scFv) polypeptide specific for the analyte and an attachment polypeptide which provides assembly of the molecules into the layer so as to be immmobilized on the receptor surface;
 (b) measuring in a blank solution the resonant frequency of the piezoelectric mass sensor of the apparatus in step (a);
 (c) contacting the piezoelectric mass sensor of the apparatus in step (b) with the liquid sample for a time sufficient to allow the analyte to bind to the recombinantly derived polypeptide molecules; and
 (d) measuring the resonant frequency of the piezoelectric mass sensor of the apparatus in step (c) wherein a change in the resonant frequency indicates presence of the analyte in the sample.

13. The method of claim 12 wherein the recombinant polypeptide molecules bind a first epitope of the analyte and the apparatus comprises a second piezoelectric mass sensor with at least one second receptor layer which provides a second receptor surface and which has immobilized on the receptor surface a second layer of recombinantly derived polypeptide molecules which bind a second epitope of the analyte, wherein each of the molecules comprises a single antibody variable heavy chain ($V_H$) or single-chain Fv (scFv) polypeptide specific for the analyte and an attachment polypeptide which provides assembly of the molecules into the layer so as to be immrnobilized on the receptor surface.

14. The method of claim 12 wherein the apparatus comprises a control piezoelectric mass sensor with at least one receptor layer which provides a receptor surface and which has immobilized on the receptor surface a layer of recombinantly derived polypeptide molecules which bind the analyte, wherein each of the molecules comprises a single antibody variable heavy chain ($V_H$) or single-chain Fv (scFv) polypeptide specific for the analyte and an attachment polypeptide which provides assembly of the molecules into the layer so as to be immmobilized on the receptor surface, wherein binding of the analyte is blocked by a blocking agent, and wherein the resonance frequency of the control sensor detects mass changes due to changes in temperature of the liquid sample during the measuring.

15. The method of claim 12, 13, or 14 wherein the single antibody $V_H$ polypeptide specific for the analyte is derived from a library of single domain camel or llama antibodies and the amino terminus of the attachment polypeptide is linked to the carboxy terminus of the $V_H$ polypeptide.

16. The method of claim 12, 13, or 14 wherein the scFv polypeptide specific for the analyte comprises an antibody variable light chain ($V_L$) polypeptide specific for the analyte and an antibody variable heavy chain ($V_H$) polypeptide specific for the analyte which are covalently linked through a polypeptide linker such that the variable light and heavy polypeptide chains are linked together while still maintaining a conformation which allows the binding of the analyte and the amino terminus of the attachment polypeptide is covalently linked to the carboxy terminus of the $V_L$ polypeptide.

17. The method of claim 16 wherein the polypeptide linker is covalently linked to an amino terminus of the $V_L$ polypeptide and a carboxy terminus of the $V_H$ polypeptide such that the $V_L$ and $V_H$ polypeptide chains are linked together.

18. The method of claim 12 wherein the sequence of the attachment polypeptide comprises at least one cysteine amino acid which provides a sulfhydryl moiety which allows the recombinantly derived polypeptide molecule to bind the receptor surface of the sensor to provide the layer on the receptor surface of the sensor.

19. The method of claim 12 wherein the attachment polypeptide comprises a polypeptide or biotin strep-tag sequence, which allows the recombinantly derived polypeptide molecule to bind streptavidin, and the receptor surface of the sensor comprises a biotin layer immobilized on the receptor surface by a sulfhydryl linkage which binds the streptavidin bound to the recombinantly derived polypeptide molecule to provide the layer on the receptor surface of the sensor.

20. The method of claim 12 wherein the attachment polypeptide comprises a polypeptide sequence for binding biotin, which allows the recombinantly derived polypeptide molecule to bind streptavidin, and the receptor layer comprises a biotin layer immobilized on the receptor surface by a sulfhydryl linkage which binds the streptavidin bound to the recombinantly derived polypeptide molecule to provide the layer on the receptor surface of the sensor.

21. The method of claim 12 wherein the receptor layer comprises an electrode for the piezoelectric mass sensor.

22. The method of claim 12 wherein the piezoelectric mass sensor is a quartz crystal microbalance.

23. A kit for immunological detection of an analyte, comprising:

an apparatus which comprises a piezoelectric mass sensor with at least one receptor layer which provides a receptor surface and which has immobilized on the receptor surface a layer of recombinantly derived polypeptide molecules which bind the analyte, wherein each of the molecules comprises a single antibody variable heavy chain ($V_H$) or single-chain Fv (scFv) polypeptide specific for the analyte and an attachment polypeptide which provides assembly of the molecules into the layer so as to be immmobilized on the receptor surface.

24. The kit of claim 23 wherein the recombinant polypeptide molecules bind a first epitope of the analyte and the apparatus comprises a second piezoelectric mass sensor with at least one second receptor layer which provides a second receptor surface and which has immobilized on the receptor surface a second layer of recombinantly derived polypeptide molecules which bind a second epitope of the analyte, wherein each of the molecules comprises a single antibody variable heavy chain ($V_H$) or single-chain Fv (scFv) polypeptide specific for the second epitope and an attachment polypeptide which provides assembly of the molecules into the layer so as to be immobilized on the second receptor surface.

25. The kit of claim 23 wherein the apparatus comprises a control piezoelectric mass sensor with at least one receptor layer which provides a receptor surface and which has immobilized on the receptor surface a layer of recombinantly derived polypeptide molecules which bind the analyte, wherein each of the molecules comprises a single antibody variable heavy chain ($V_H$) or singlechain Fv (scFv) polypeptide specific for the analyte and an attachment polypeptide which provides assembly of the molecules into the layer so as to be immmobilized on the receptor surface, wherein binding of the analyte is blocked by a blocking agent, and wherein the resonance frequency of the control sensor detects mass changes due to changes in temperature of the liquid sample during the measuring.

26. The kit of claim 23, 24, or 25 wherein the single antibody $V_H$ polypeptide specific for the analyte is derived from a library of single domain camel or llama antibodies and the amino terminus of the attachment polypeptide is linked to the carboxy terminus of the $V_H$ polypeptide.

27. The kit of claim 23, 24, or 25 wherein the scFv polypeptide specific for the analyte comprises an antibody variable light chain ($V_L$) polypeptide specific for the analyte and an antibody variable heavy chain ($V_H$) polypeptide specific for the analyte which are covalently linked through a polypeptide linker such that the variable light and heavy polypeptide chains are linked together while still maintaining a conformation which allows the binding of the analyte and the amino terminus of the attachment polypeptide is covalently linked to the carboxy terminus of the $V_L$ polypeptide.

28. The kit of claim 27 wherein the polypeptide linker is covalently linked to an amino terminus of the $V_L$ polypeptide and a carboxy terminus of the $V_H$ polypeptide such that the $V_L$ and $V_H$ polypeptide chains are linked together.

29. The kit of claim 23 wherein the sequence of the attachment polypeptide comprises at least one cysteine amino acid which provides a sulfhydryl moiety which allows the recombinantly derived polypeptide molecule to bind the receptor surface of the sensor to provide the layer on the receptor surface of the sensor.

30. The kit of claim 23 wherein the attachment polypeptide comprises a polypeptide sequence or biotin strep-tag sequence, which allows the recombinantly derived polypeptide molecule to bind streptavidin, and the receptor surface of the sensor comprises a biotin layer immobilized on the receptor surface by a sulfhydryl linkage which binds the streptavidin bound to the recombinantly derived polypeptide molecule to provide the layer on the receptor surface of the sensor.

31. The kit of claim 23 wherein the attachment polypeptide comprises a polypeptide sequence or biotin, which allows the recombinantly derived polypeptide molecule to bind streptavidin, and the receptor layer comprises a biotin layer immobilized on the receptor surface by a sulfhydryl linkage which binds the streptavidin bound to the recombinantly derived polypeptide molecule to provide the layer on the receptor surface of the sensor.

32. The kit of claim 23 wherein the receptor layer comprises an electrode for the piezoelectric mass sensor.

33. The kit of claim 23 wherein the piezoelectric mass sensor is a quartz crystal microbalance.

* * * * *

UNITED STATES PATENT AND TRADEMARK OFFICE
CERTIFICATE OF CORRECTION

PATENT NO. : 7,329,536 B2
APPLICATION NO. : 10/861617
DATED : February 12, 2008
INVENTOR(S) : Xiangqun Zeng, Gabrielle Stryker and Raymond L. Mernaugh It is certified that error appears in the above-identified patent and that said Letters Patent is hereby corrected as shown below:

Column 40, line 32, "VH" should be --$V_H$--.

Column 45, Line 33, "scFv–SH + Au → scFv–S–Au + e + $H^+$" should be --scFv–SH + Au → scFv–S–A + e + $H^+$--.

Column 46, line 63, "Ret" should be --$R_{et}$--.

Column 49, line 44, "($\Delta$f=–2$\Delta$mnf" should be --($\Delta f$=–2$\Delta mnf$--.

Column 50, line 4, "Rq>1.1%" should be --Rq$\geq$1.1%--.

Column 62, line 55, "VH" should be --$V_H$--.

Column 62, line 59, "VH" should be --$V_H$--.

Signed and Sealed this

Second Day of December, 2008

JON W. DUDAS
*Director of the United States Patent and Trademark Office*

SEQUENCE LISTING

<160> NUMBER OF SEQ ID NOS: 21

<210> SEQ ID NO 1
<211> LENGTH: 31
<212> TYPE: DNA
<213> ORGANISM: Artificial
<220> FEATURE:
<223> OTHER INFORMATION: 3' PCR primer mouse IgG1 CH1 domain

<400> SEQUENCE: 1
acaatccctg ggcacaattt tcttgtccac c                           31

<210> SEQ ID NO 2
<211> LENGTH: 20
<212> TYPE: DNA
<213> ORGANISM: Artificial
<220> FEATURE:
<223> OTHER INFORMATION: 5' PCR pprimer mouse IgG1 VH domain

<400> SEQUENCE: 2
magcttcagg agtcrggacc                                        20

<210> SEQ ID NO 3
<211> LENGTH: 20
<212> TYPE: DNA
<213> ORGANISM: Artificial
<220> FEATURE:
<223> OTHER INFORMATION: 5' PCR primer mouse IgG1 VH domain

<400> SEQUENCE: 3
cagctgaags astcaggacc                                        20

<210> SEQ ID NO 4
<211> LENGTH: 21
<212> TYPE: DNA
<213> ORGANISM: Artificial
<220> FEATURE:
<223> OTHER INFORMATION: 5' PCR primer mouse IgG1 VH domain

<400> SEQUENCE: 4
mwgskggtgg agtctggggg a                                      21

<210> SEQ ID NO 5
<211> LENGTH: 21
<212> TYPE: DNA
<213> ORGANISM: Artificial
<220> FEATURE:
<223> OTHER INFORMATION: 5' PCR primer mouse IgG1 VH domain

<400> SEQUENCE: 5
arsstggtgg aatctggagg a                                      21

<210> SEQ ID NO 6
<211> LENGTH: 20
<212> TYPE: DNA
<213> ORGANISM: Artificial

```
<220> FEATURE:
<223> OTHER INFORMATION: 5' PCR primer mouse IgG1 VH domain

<400> SEQUENCE: 6
argstgrtsg agtctggagg                                              20

<210> SEQ ID NO 7
<211> LENGTH: 18
<212> TYPE: DNA
<213> ORGANISM: Artificial
<220> FEATURE:
<223> OTHER INFORMATION: 5' PCR primer mouse IgG1 VH domain

<400> SEQUENCE: 7
carsygcagc aryctggg                                                18

<210> SEQ ID NO 8
<211> LENGTH: 18
<212> TYPE: DNA
<213> ORGANISM: Artificial
<220> FEATURE:
<223> OTHER INFORMATION: 5' PCR primer mouse IgG1 VH domain

<400> SEQUENCE: 8
cagytgswgc artctgga                                                18

<210> SEQ ID NO 9
<211> LENGTH: 18
<212> TYPE: DNA
<213> ORGANISM: Artificial
<220> FEATURE:
<223> OTHER INFORMATION: 5' PCR primer mouse IgG1 VH domain

<400> SEQUENCE: 9
cagctgcagc agtcwgtg                                                18

<210> SEQ ID NO 10
<211> LENGTH: 20
<212> TYPE: DNA
<213> ORGANISM: Artificial
<220> FEATURE:
<223> OTHER INFORMATION: 5' PCR primer mouse IgG1 VH

<400> SEQUENCE: 10
masytgswgg wgwctggagg                                              20

<210> SEQ ID NO 11
<211> LENGTH: 17
<212> TYPE: DNA
<213> ORGANISM: Artificial
<220> FEATURE:
<223> OTHER INFORMATION: 5' PCR primer mouse IgG1 VH domain

<400> SEQUENCE: 11
cagmtscagc agyctgg                                                 17

<210> SEQ ID NO 12
<211> LENGTH: 20
<212> TYPE: DNA
<213> ORGANISM: Artificial
<220> FEATURE:
<223> OTHER INFORMATION: 5' PCR primer mouse IgG1 VH domain with actual
      sequence

<400> SEQUENCE: 12
cagctgaagg agtcaggacc                                              20
```

<210> SEQ ID NO 13
<211> LENGTH: 734
<212> TYPE: DNA
<213> ORGANISM: Artificial
<220> FEATURE:
<223> OTHER INFORMATION: recombinant scFv polypeptide of mouse Fv with
      carboxy cysteine codon

<400> SEQUENCE: 13

```
ggcgccagct gaaggagtca ggacctggcc tcgtgaagcc ttctcagtct ctgtctctca     60
cctgctctgt cactggcaac tccatcacta gtgtctatta ctggaactgg atccggcagt    120
ttccaggaaa caaactggaa tggttgggct ccataagcca cggtagcaat aactacaatc    180
catctctcaa aaatcgaatc tccatcactc gtgactcatc taagaaccag ttttcctga    240
agttgaattc tgtgactact gaggacacag ctacatatta ctgtgcaaga gcgggaaaat    300
acggctacta tgctctggca tactggggtc aaggaacctc agtcaccgtc tccccagccg    360
gaggttcagg tggatctggt ggctcgagtg atcagcaga cgtccagata acccagactc     420
cagccgccct atctgcatct gtgggagaaa ctgtcaccat cacatgtcga acaagtgaga    480
atatttacag ttatttagca tggtttcagc agaaacaggg aaaatctcct caggtcctgg    540
tctataatgc aaaagcctta ccagaaggtg tgccatcaag gttcagtggc agtggatcag    600
gcacacagtt ttctctgaag atcaacagcc tgcagcctga agattttggg acttattact    660
gtcaaaacca ttatggtact ccattcacgt tcggctcggg gacaatgttg gaaatacaac    720
ggtgctgagg cgcc                                                     734
```

<210> SEQ ID NO 14
<211> LENGTH: 738
<212> TYPE: DNA
<213> ORGANISM: Artificial
<220> FEATURE:
<223> OTHER INFORMATION: Single chain antibody, A10Brs derived from
      mouse hybridoma clone

<400> SEQUENCE: 14

```
atggcccagg tgcagctgca gcagtcagga actgaagtgg taaagcctgg ggcttcagtg     60
aagttgtcct gcaaggcttc tggctacatc ttcacaagtt atgatataga ctgggtgagg    120
cagacgcctg aacagggact tgagtggatt ggatggattt ttcctggaga ggggagtact    180
gaatacaatg agaagttcaa gggcagggcc acactgagtg tagacaagtc ctccagcaca    240
gcctatatgg agctcactag gctgacatct gaggactctg ctgtctattt ctgtgctaga    300
ggggactact ataggcgcta ctttgacttg tggggccaag gaccacggt caccgtctcc     360
tcaggtggag gcggttcagg cggaggtggc tctggcggtg gcggatcgga cattgagctc    420
acccagtctc caacaatcat gtctgcatct ccaggggaga gggtcaccat gacctgcagt    480
gccagctcaa gtatacgtta catatattgg taccaacaga gcctggatc ctcccccaga    540
ctcctgattt atgacacatc caacgtggct tctggagtcc cttctcgctt cagtggcagt    600
gggtctggga cctcttattc tctcacaatc aaccgaatgg aggctgagga tgctgccact    660
tattactgcc aggagtggag tggttatccg tacacgttcg ggggggggac caagctggag    720
ctgaaacagg cggccgca                                                  738
```

<210> SEQ ID NO 15
<211> LENGTH: 246
<212> TYPE: PRT

```
<213> ORGANISM: Artificial
<220> FEATURE:
<223> OTHER INFORMATION: Single chain antibody, A10Brs, derived from
      mouse hybridoma clone.

<400> SEQUENCE: 15

Met Ala Gln Val Gln Leu Gln Gln Ser Gly Thr Glu Val Val Lys Pro
1               5                   10                  15

Gly Ala Ser Val Lys Leu Ser Cys Lys Ala Ser Gly Tyr Ile Phe Thr
            20                  25                  30

Ser Tyr Asp Ile Asp Trp Val Arg Gln Thr Pro Glu Gln Gly Leu Glu
        35                  40                  45

Trp Ile Gly Trp Ile Phe Pro Gly Glu Gly Ser Thr Glu Tyr Asn Glu
    50                  55                  60

Lys Phe Lys Gly Arg Ala Thr Leu Ser Val Asp Lys Ser Ser Ser Thr
65                  70                  75                  80

Ala Tyr Met Glu Leu Thr Arg Leu Thr Ser Glu Asp Ser Ala Val Tyr
                85                  90                  95

Phe Cys Ala Arg Gly Asp Tyr Tyr Arg Arg Tyr Phe Asp Leu Trp Gly
            100                 105                 110

Gln Gly Thr Thr Val Thr Val Ser Ser Gly Gly Gly Ser Ser Gly
        115                 120                 125

Gly Gly Ser Gly Gly Gly Ser Asp Ile Glu Leu Thr Gln Ser Pro
    130                 135                 140

Thr Ile Met Ser Ala Ser Pro Gly Glu Arg Val Thr Met Thr Cys Ser
145                 150                 155                 160

Ala Ser Ser Ser Ile Arg Tyr Ile Tyr Trp Tyr Gln Gln Lys Pro Gly
                165                 170                 175

Ser Ser Pro Arg Leu Leu Ile Tyr Asp Thr Ser Asn Val Ala Ser Gly
            180                 185                 190

Val Pro Ser Arg Phe Ser Gly Ser Gly Ser Gly Thr Ser Tyr Ser Leu
        195                 200                 205

Thr Ile Asn Arg Met Glu Ala Glu Asp Ala Ala Thr Tyr Tyr Cys Gln
    210                 215                 220

Glu Trp Ser Gly Tyr Pro Tyr Thr Phe Gly Gly Gly Thr Lys Leu Glu
225                 230                 235                 240

Leu Lys Gln Ala Ala Ala
                245

<210> SEQ ID NO 16
<211> LENGTH: 738
<212> TYPE: DNA
<213> ORGANISM: Artificial
<220> FEATURE:
<223> OTHER INFORMATION: Modified single chain antibody, A10BC3, derived
      from A10Brs mouse hybridoma clone.

<400> SEQUENCE: 16
atggcccagg tgcagctgca gcagtcagga actgaagtgg taaagcctgg ggcttcagtg      60
aagttgtcct gcaaggcttc tggctacatc ttcacaagtt atgatataga ctgggtgagg     120
cagacgcctg aacagggact tgagtggatt ggatggattt tcctggagag ggggagtact     180
gaatacaatg agaagttcaa gggcagggcc acactgagtg tagacaagtc ctccagcaca     240
gcctatatgg agctcactag gctgacatct gaggactctg ctgtctattt ctgtgctaga     300
ggggactact ataggcgcta ctttgacttg tggggccaag gaccacggt caccgtctcc     360 tcaagtcatg gcggtcacgg cggaggtggc tctggcggtg gcggatcgga cattgagctc     420
```

-continued

```
acccagtctc caacaatcat gtctgcatct ccaggggaga gggtcaccat gacctgcagt      480
gccagctcaa gtatacgtta catatattgg taccaacaga agcctggatc ctcccccaga      540
ctcctgattt atgacacatc caacgtggct tctggagtcc cttctcgctt cagtggcagt      600
gggtctggga cctcttattc tctcacaatc aaccgaatgg aggctgagga tgctgccact      660
tattactgcc aggagtggag tggttatccg tacacgttcg agggggggac caagctggag      720
ctgaaacagg cggccgca                                                    738
```

<210> SEQ ID NO 17
<211> LENGTH: 246
<212> TYPE: PRT
<213> ORGANISM: Artificial
<220> FEATURE:
<223> OTHER INFORMATION: Modified single chain antibody, A10BC3, derived
      from A10Brs mouse hybridoma clone.

<400> SEQUENCE: 17

```
Met Ala Gln Val Gln Leu Gln Gln Ser Gly Thr Glu Val Val Lys Pro
1               5                   10                  15

Gly Ala Ser Val Lys Leu Ser Cys Lys Ala Ser Gly Tyr Ile Phe Thr
            20                  25                  30

Ser Tyr Asp Ile Asp Trp Val Arg Gln Thr Pro Glu Gln Gly Leu Glu
        35                  40                  45

Trp Ile Gly Trp Ile Phe Pro Gly Glu Gly Ser Thr Glu Tyr Asn Glu
    50                  55                  60

Lys Phe Lys Gly Arg Ala Thr Leu Ser Val Asp Lys Ser Ser Ser Thr
65                  70                  75                  80

Ala Tyr Met Glu Leu Thr Arg Leu Thr Ser Glu Asp Ser Ala Val Tyr
                85                  90                  95

Phe Cys Ala Arg Gly Asp Tyr Tyr Arg Arg Tyr Phe Asp Leu Trp Gly
            100                 105                 110

Gln Gly Thr Thr Val Thr Val Ser Ser His Gly Gly His Gly Gly
        115                 120                 125

Gly Gly Ser Gly Gly Gly Gly Ser Asp Ile Glu Leu Thr Gln Ser Pro
    130                 135                 140

Thr Ile Met Ser Ala Ser Pro Gly Glu Arg Val Thr Met Thr Cys Ser
145                 150                 155                 160

Ala Ser Ser Ser Ile Arg Tyr Ile Tyr Trp Tyr Gln Gln Lys Pro Gly
                165                 170                 175

Ser Ser Pro Arg Leu Leu Ile Tyr Asp Thr Ser Asn Val Ala Ser Gly
            180                 185                 190

Val Pro Ser Arg Phe Ser Gly Ser Gly Ser Gly Thr Ser Tyr Ser Leu
        195                 200                 205

Thr Ile Asn Arg Met Glu Ala Glu Asp Ala Ala Thr Tyr Tyr Cys Gln
    210                 215                 220

Glu Trp Ser Gly Tyr Pro Tyr Thr Phe Gly Gly Thr Lys Leu Glu
225                 230                 235                 240

Leu Lys Gln Ala Ala Ala
                245
```

<210> SEQ ID NO 18
<211> LENGTH: 15
<212> TYPE: PRT
<213> ORGANISM: Artificial
<220> FEATURE:
<223> OTHER INFORMATION: ScFv Linker sequence

```
<400> SEQUENCE: 18

Gly Gly Gly Gly Ser Gly Gly Gly Ser Gly Gly Gly Gly Ser
1               5                   10                  15

<210> SEQ ID NO 19
<211> LENGTH: 15
<212> TYPE: PRT
<213> ORGANISM: Artificial
<220> FEATURE:
<223> OTHER INFORMATION: ScFv Linker

<400> SEQUENCE: 19

Ser His Gly Gly His Gly Gly Gly Ser Gly Gly Gly Gly Ser
1               5                   10                  15

<210> SEQ ID NO 20
<211> LENGTH: 15
<212> TYPE: PRT
<213> ORGANISM: Artificial
<220> FEATURE:
<223> OTHER INFORMATION: ScFv Linker

<400> SEQUENCE: 20

Cys Gly Gly Gly Ser Gly Gly Gly Ser Gly Gly Gly Gly Ser
1               5                   10                  15

<210> SEQ ID NO 21
<211> LENGTH: 15
<212> TYPE: PRT
<213> ORGANISM: Artificial
<220> FEATURE:
<223> OTHER INFORMATION: ScFv Linker

<400> SEQUENCE: 21

Cys His Gly Gly His Gly Gly Gly Ser Gly Gly Gly Gly Ser
1               5                   10                  15
```